(12) United States Patent
Kriesel

(10) Patent No.: US 7,220,245 B2
(45) Date of Patent: *May 22, 2007

(54) INFUSION APPARATUS

(76) Inventor: Marshall S. Kriesel, 80 N. Mississippi River Blvd., St. Paul, MN (US) 55104

( * ) Notice: Subject to any disclaimer, the term of this patent is extended or adjusted under 35 U.S.C. 154(b) by 162 days.

This patent is subject to a terminal disclaimer.

(21) Appl. No.: 10/855,425

(22) Filed: May 26, 2004

(65) Prior Publication Data

US 2005/0277882 A1   Dec. 15, 2005

(51) Int. Cl.
*A61M 5/20* (2006.01)
*A61M 5/00* (2006.01)
*A61K 9/22* (2006.01)

(52) U.S. Cl. .................. 604/134; 604/890.1; 604/246; 604/248; 604/207; 604/211; 604/216

(58) Field of Classification Search ............. 604/890.1, 604/891.1, 131, 133–135, 151, 153, 207, 604/211, 216, 236, 246–248

See application file for complete search history.

(56) References Cited

U.S. PATENT DOCUMENTS

| | | | |
|---|---|---|---|
| 3,731,681 A | 5/1973 | Blackshear et al. | |
| 4,381,006 A | 4/1983 | Genese | |
| 4,557,728 A | 12/1985 | Sealfon et al. | |
| 4,608,042 A | 8/1986 | Vanderveen et al. | |
| 4,681,566 A | 7/1987 | Fenton, Jr. et al. | |
| 4,755,172 A | 7/1988 | Baldwin | |
| 4,772,263 A | 9/1988 | Dorman et al. | |
| 4,846,806 A * | 7/1989 | Wigness et al. | 604/175 |
| 4,850,807 A | 7/1989 | Frantz | |
| 4,863,429 A | 9/1989 | Baldwin | |
| 5,014,750 A | 5/1991 | Winchell et al. | |
| 5,098,377 A | 3/1992 | Borsanyi et al. | |
| 5,100,389 A | 3/1992 | Vaillancourt | |
| 5,176,641 A | 1/1993 | Idriss | |
| 5,205,820 A | 4/1993 | Kriesel | |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,336,188 A | 8/1994 | Kriesel | |
| 5,346,476 A * | 9/1994 | Elson | 604/135 |
| 5,380,287 A | 1/1995 | Kikuchi et al. | |
| 5,411,480 A | 5/1995 | Kriesel | |
| 5,419,771 A | 5/1995 | Kriesel | |
| 5,484,410 A | 1/1996 | Kriesel et al. | |
| 5,499,968 A | 3/1996 | Milijasevic et al. | |
| 5,514,090 A | 5/1996 | Kriesel et al. | |
| 5,545,139 A | 8/1996 | Kriesel | |
| 5,620,420 A | 4/1997 | Kriesel | |

(Continued)

*Primary Examiner*—Kevin C. Sirmons
*Assistant Examiner*—Benjamin Huh
(74) *Attorney, Agent, or Firm*—James E. Brunton, Esq.

(57) ABSTRACT

A compact fluid dispenser for use in controllably dispensing fluid medicaments, such as, antibiotics, oncolytics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

17 Claims, 52 Drawing Sheets

U.S. PATENT DOCUMENTS

| | | | |
|---|---|---|---|
| 5,693,018 A | 12/1997 | Kriesel et al. |
| 5,720,729 A | 2/1998 | Kriesel |
| 5,721,382 A | 2/1998 | Kriesel et al. |
| 5,735,818 A | 4/1998 | Kriesel et al. |
| 5,741,242 A | 4/1998 | Kriesel |
| 5,743,879 A | 4/1998 | Kriesel |
| 5,766,149 A | 6/1998 | Kriesel et al. |
| 5,779,676 A | 7/1998 | Kriesel et al. |
| 5,807,323 A | 9/1998 | Kriesel et al. |
| 5,836,484 A | 11/1998 | Gerber |
| 5,858,005 A | 1/1999 | Kriesel |
| 5,885,250 A | 3/1999 | Kriesel et al. |
| 5,897,530 A | 4/1999 | Jackson |
| 5,921,962 A | 7/1999 | Kriesel et al. |
| 5,925,017 A | 7/1999 | Kriesel et al. |
| 5,957,891 A | 9/1999 | Kriesel et al. |
| 5,993,425 A * | 11/1999 | Kriesel | 604/191 |
| 6,010,482 A | 1/2000 | Kriesel et al. |
| 6,027,472 A | 2/2000 | Kriesel et al. |
| 6,030,363 A | 2/2000 | Kriesel |
| 6,045,533 A * | 4/2000 | Kriesel et al. | 604/132 |
| 6,063,059 A | 5/2000 | Kriesel |
| 6,068,613 A | 5/2000 | Kriesel et al. |
| 6,068,614 A | 5/2000 | Kimber et al. |
| 6,086,561 A | 7/2000 | Kriesel et al. |
| 6,090,071 A | 7/2000 | Kriesel |
| 6,095,491 A | 8/2000 | Kriesel |
| 6,126,637 A | 10/2000 | Kriesel et al. |
| 6,126,642 A | 10/2000 | Kriesel et al. |
| 6,152,898 A | 11/2000 | Olsen |
| 6,159,180 A | 12/2000 | Kriesel et al. |
| 6,176,845 B1 | 1/2001 | Kriesel et al. |
| 6,183,441 B1 | 2/2001 | Kriesel et al. |
| 6,190,359 B1 | 2/2001 | Heruth |
| 6,210,368 B1 | 4/2001 | Rogers |
| 6,236,624 B1 | 5/2001 | Kriesel et al. |
| 6,245,041 B1 | 6/2001 | Kriesel |
| 6,258,062 B1 | 7/2001 | Thielen et al. |
| 6,270,481 B1 | 8/2001 | Mason et al. |
| 6,273,133 B1 | 8/2001 | Williamson et al. |
| 6,277,095 B1 | 8/2001 | Kriesel et al. |
| 6,293,159 B1 | 9/2001 | Kriesel et al. |
| 6,319,235 B1 | 11/2001 | Yoshino |
| 6,355,019 B1 | 3/2002 | Kriesel et al. |
| 6,391,006 B1 | 5/2002 | Kriesel et al. |
| 6,394,980 B2 | 5/2002 | Kriesel et al. |
| 6,398,760 B1 | 6/2002 | Danby |
| 6,416,495 B1 * | 7/2002 | Kriesel et al. | 604/132 |
| 6,485,461 B1 | 11/2002 | Mason et al. |
| 6,537,249 B2 | 3/2003 | Kriesel et al. |
| 6,542,350 B1 | 4/2003 | Rogers |
| 6,569,125 B2 | 5/2003 | Jepson et al. |
| 6,645,175 B2 | 11/2003 | Kriesel et al. |
| 6,669,668 B1 | 12/2003 | Kleeman et al. |
| 2005/0033233 A1* | 2/2005 | Kriesel | 604/133 |
| 2005/0143685 A1* | 6/2005 | Peyron et al. | 604/19 |

\* cited by examiner

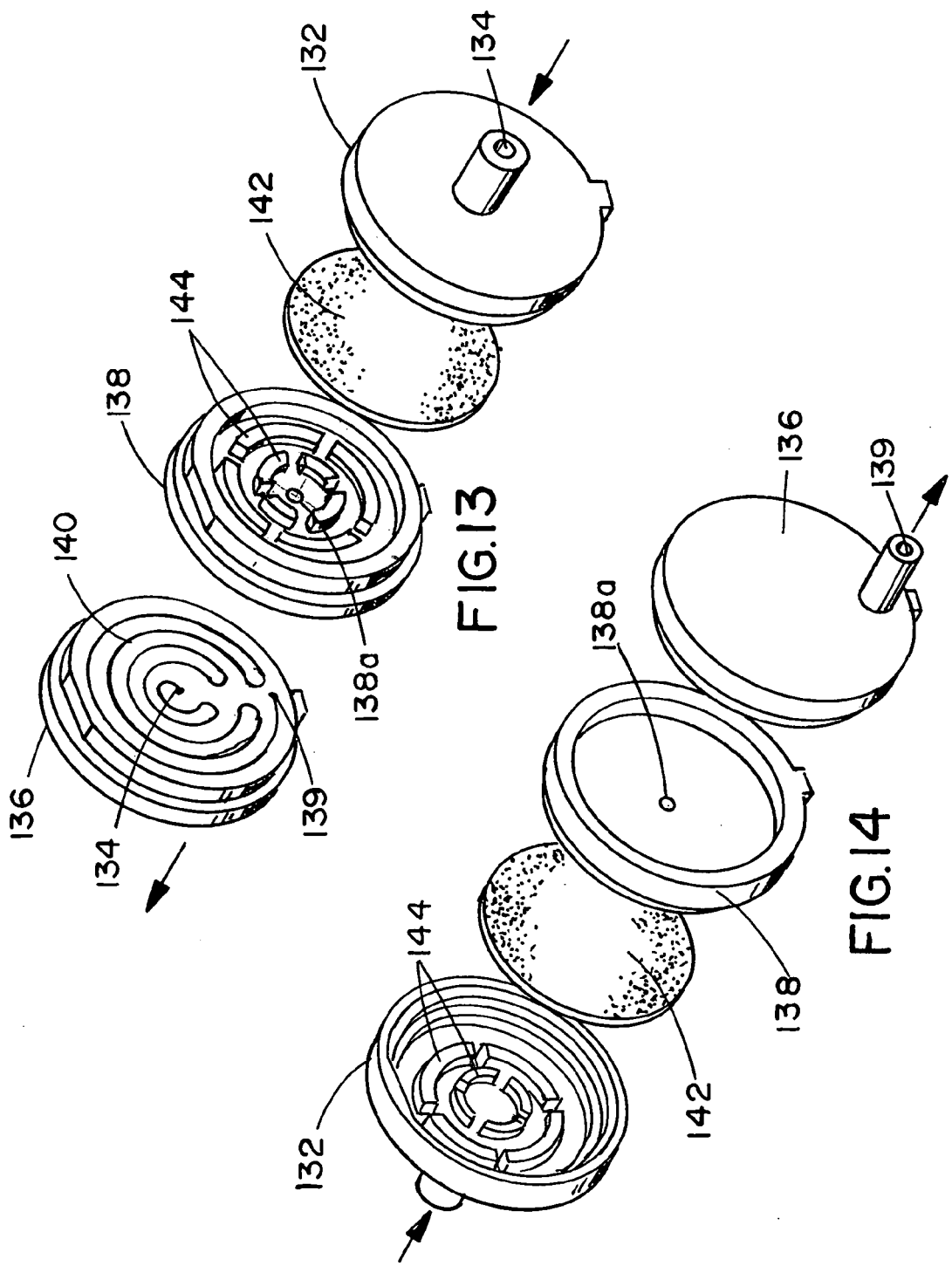

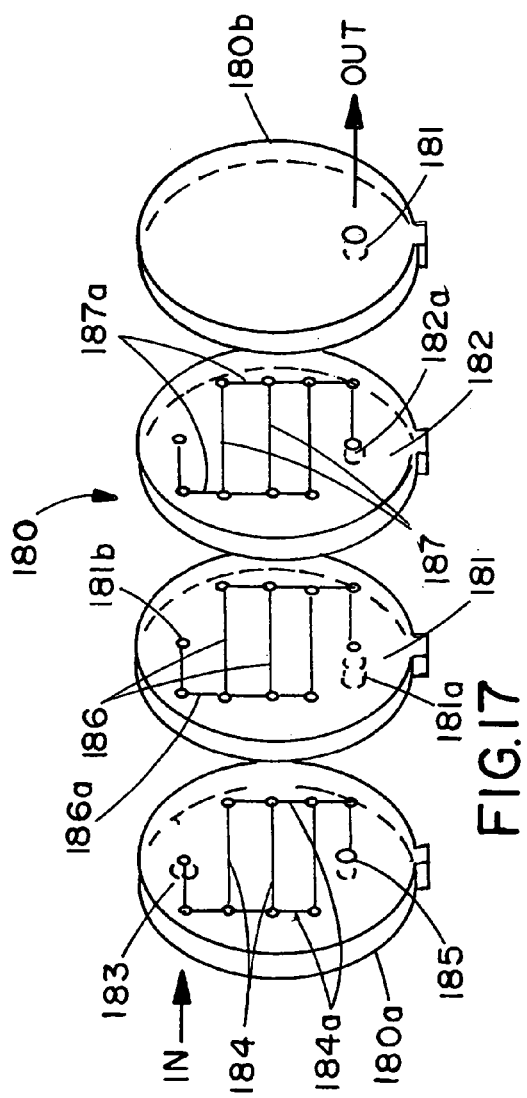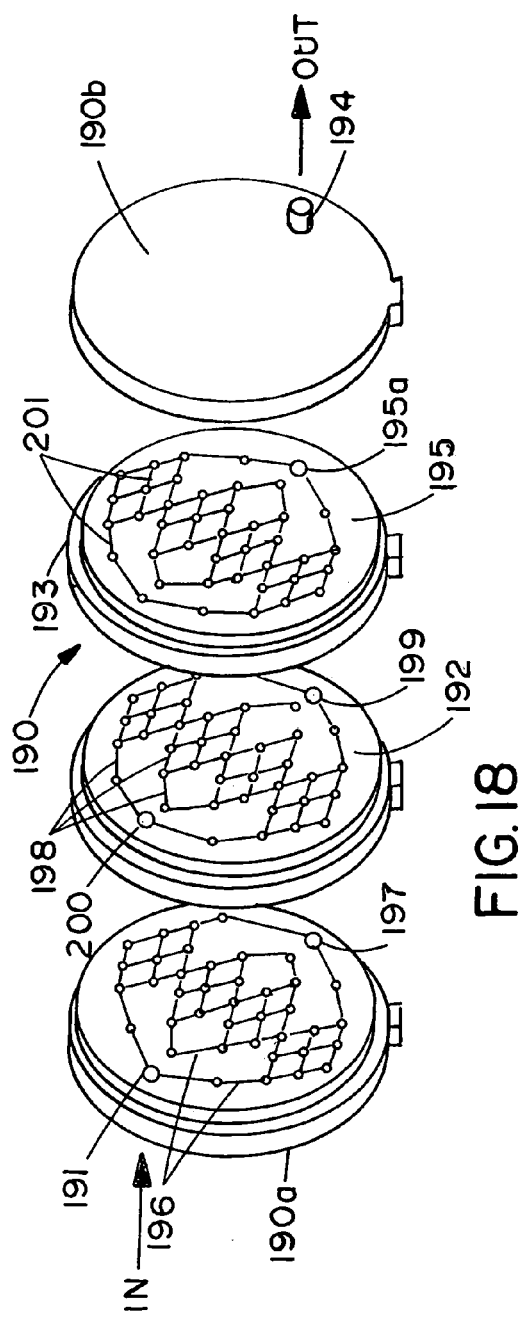

| | | |
|---|---|---|
| F CONFIG. | MULTIWAVE COMP. SPRING | |
| G CONFIG. | BELLEVILLE SPRING WASHER | |
| H CONFIG. | BELLEVILLE WASHER (STACKED) | |
| I CONFIG. | DISC-SPRING (INT. TOOTH) | |
| J CONFIG. | DISC-SPRING (INT. TOOTH) STACKED | |

FIG. 19C (A) DISC SPRING STACK CONSISTING OF DISC SPRINGS OF DIFFERENT THIKNESSES.

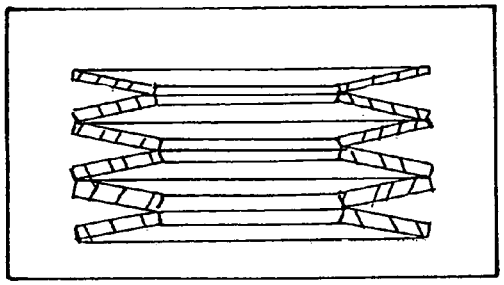

(D) GUIDING BY CYLINDRICAL "SHOULDERS" AT THE INSIDE & OUTSIDE DIA'S.

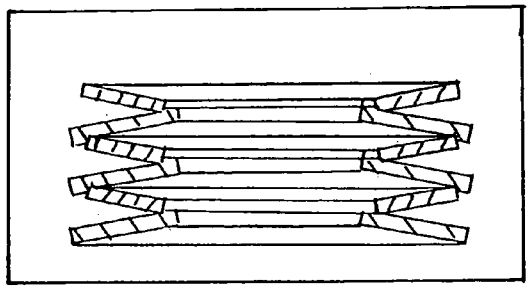

(B) DISC SPRING STACKS OF PARALLEL COMPONENTS OF DIFFERENT NUMBERS OF DISC SPRINGS ARRANGED IN SERIES.

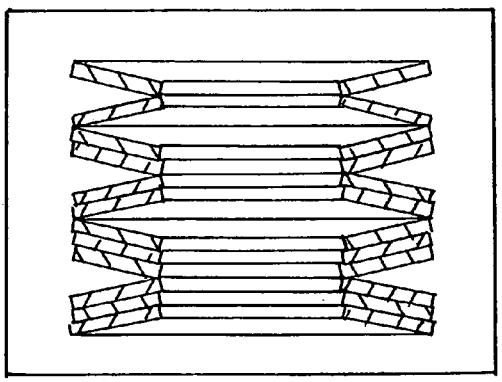

(E) GUIDING BY MEANS OF INTERMEDIATE RINGS.

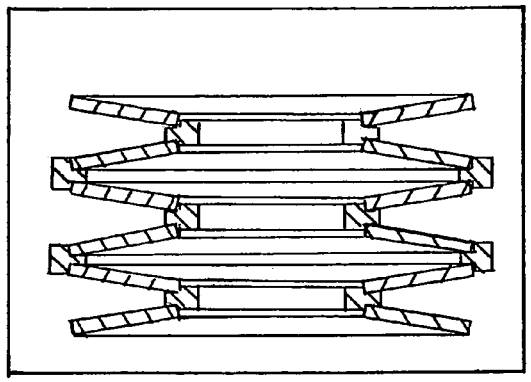

(C) DISC SPRING STACKS WITH DEFLECTION LIMITING RINGS OF DIFFERENT THICKNESSES

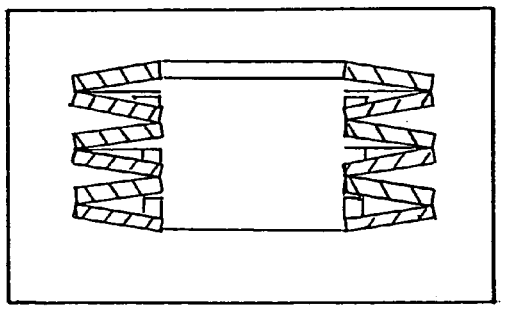

(F) GUIDING BY BALLS OR WIRE RINGS.

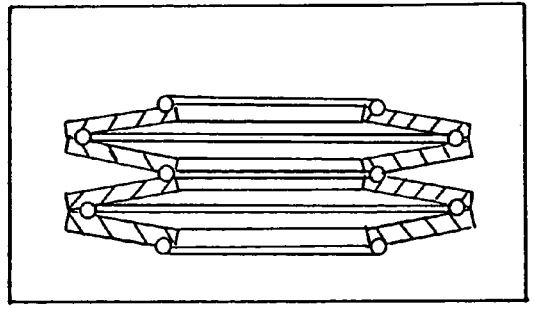

FIG. 19F

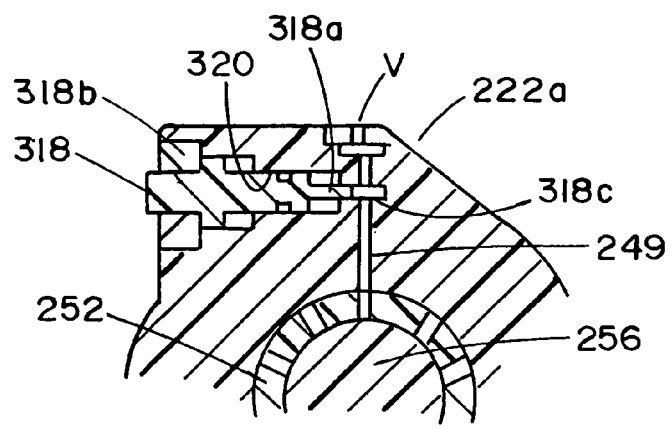
FIG. 22A
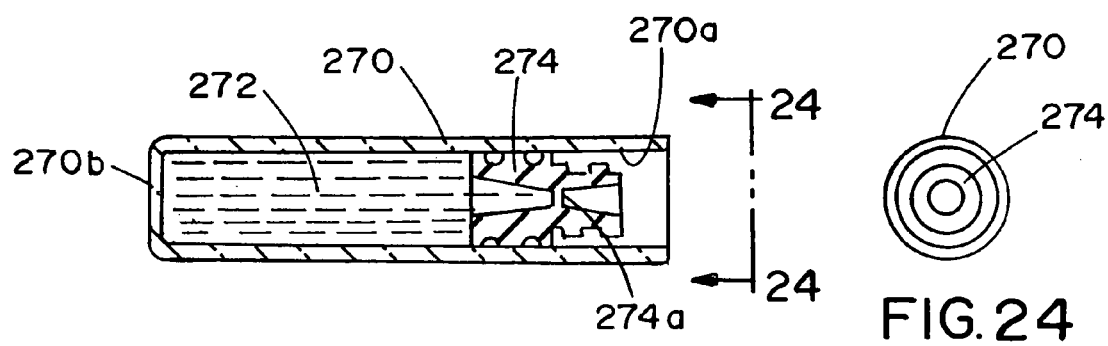
FIG. 23
FIG. 24

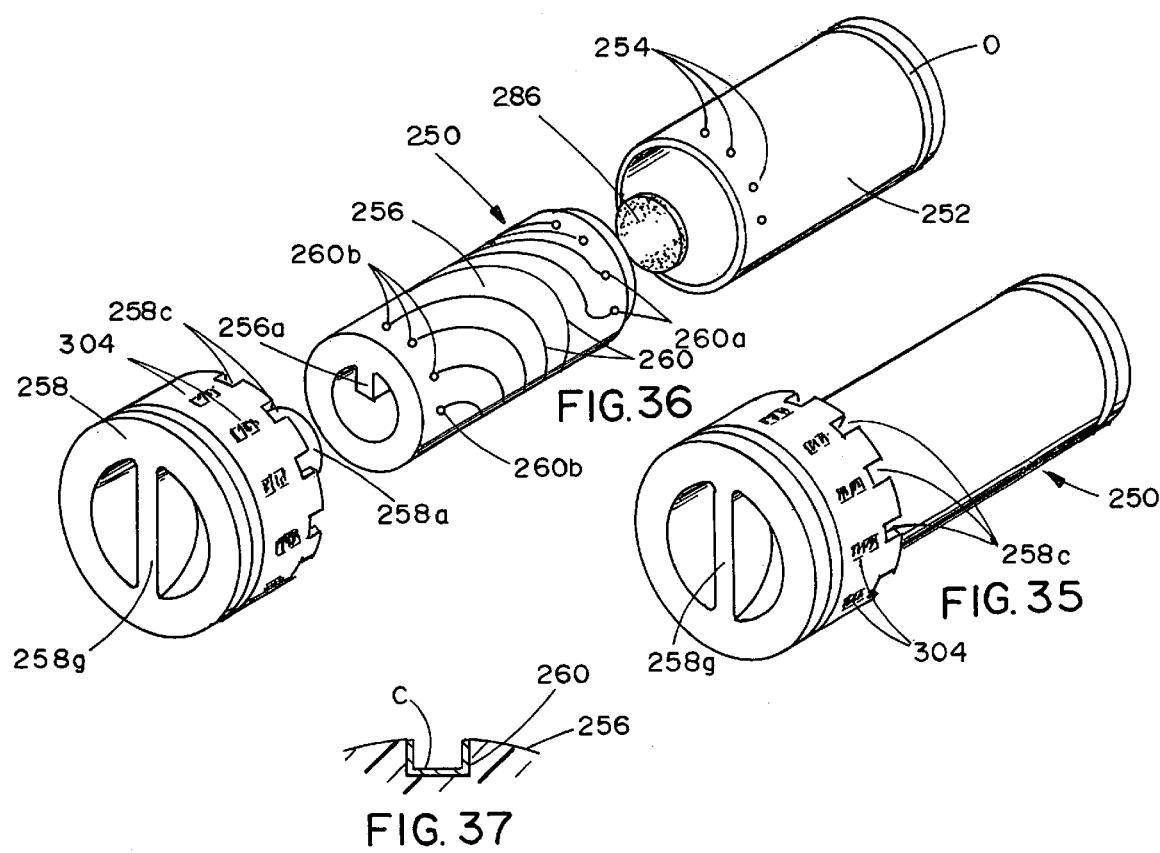

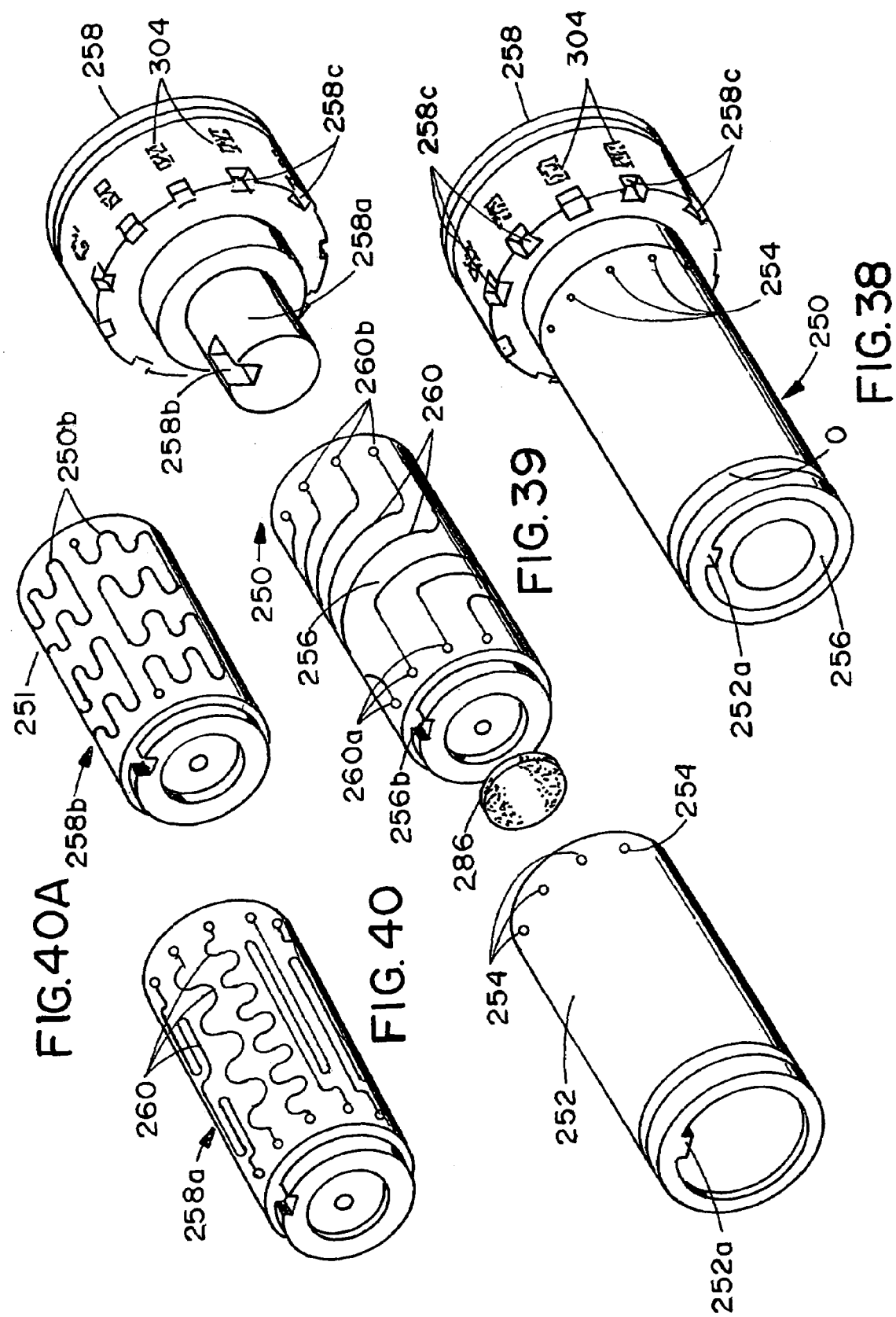

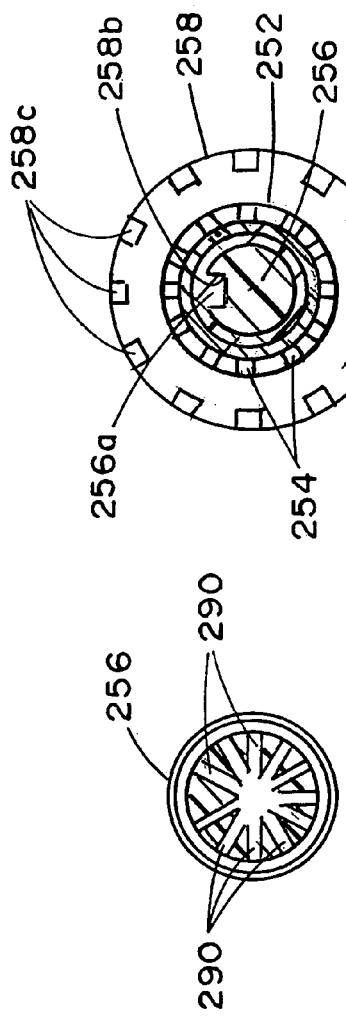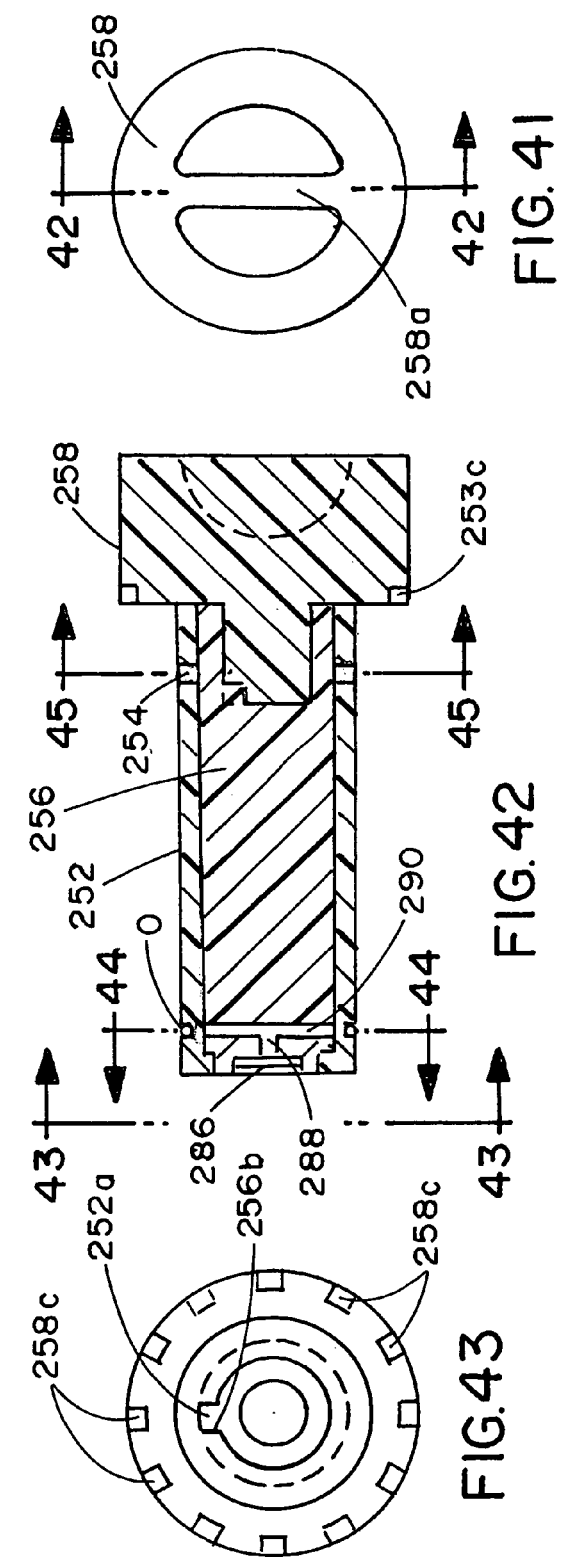

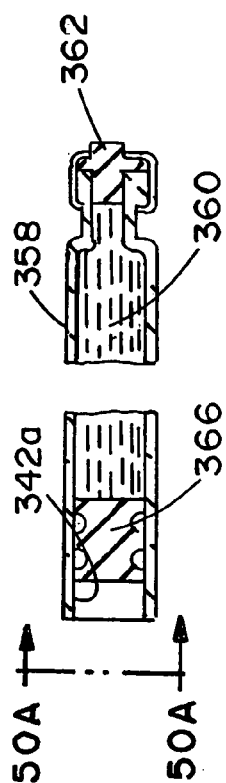
FIG. 50
FIG. 50A
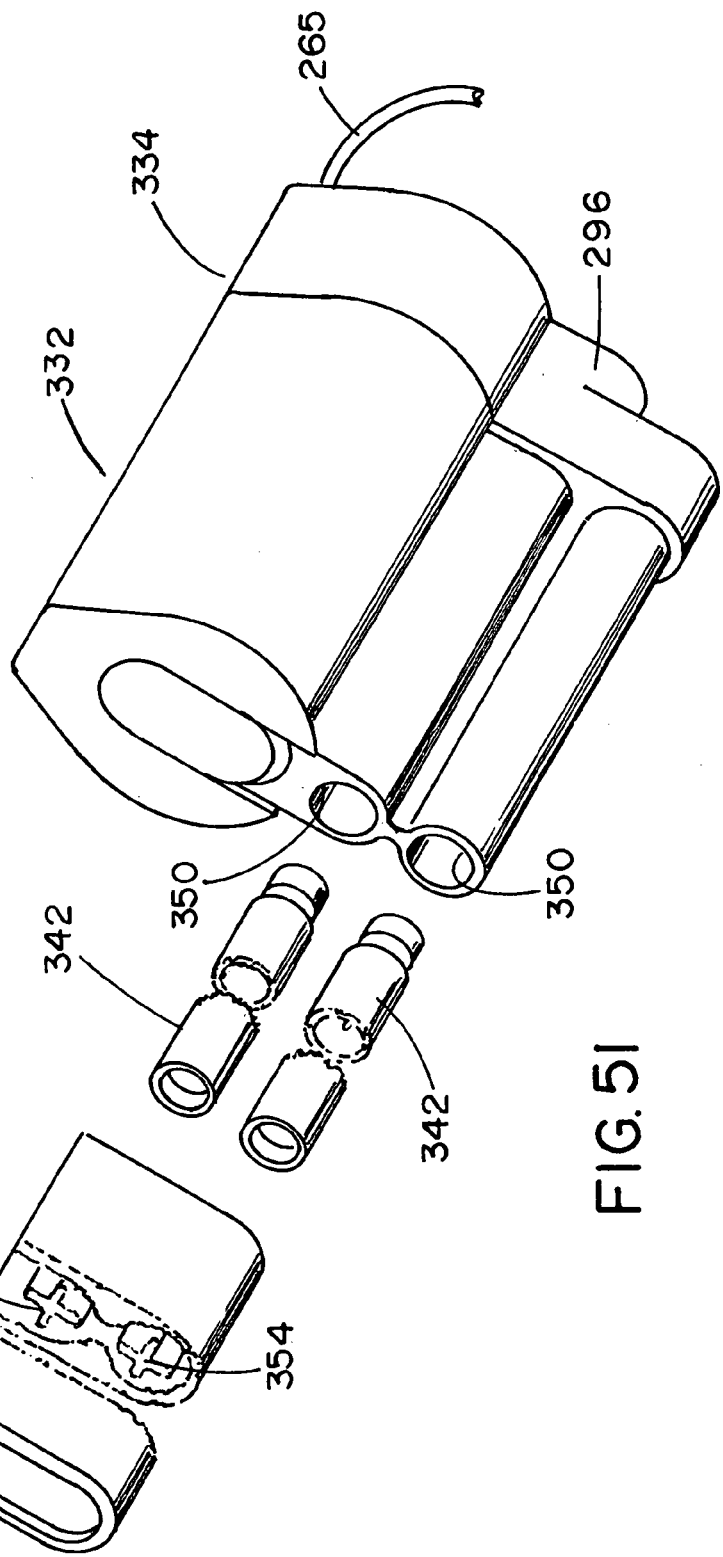
FIG. 51

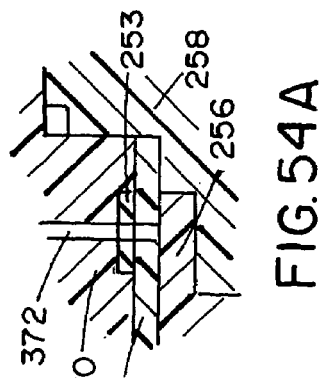
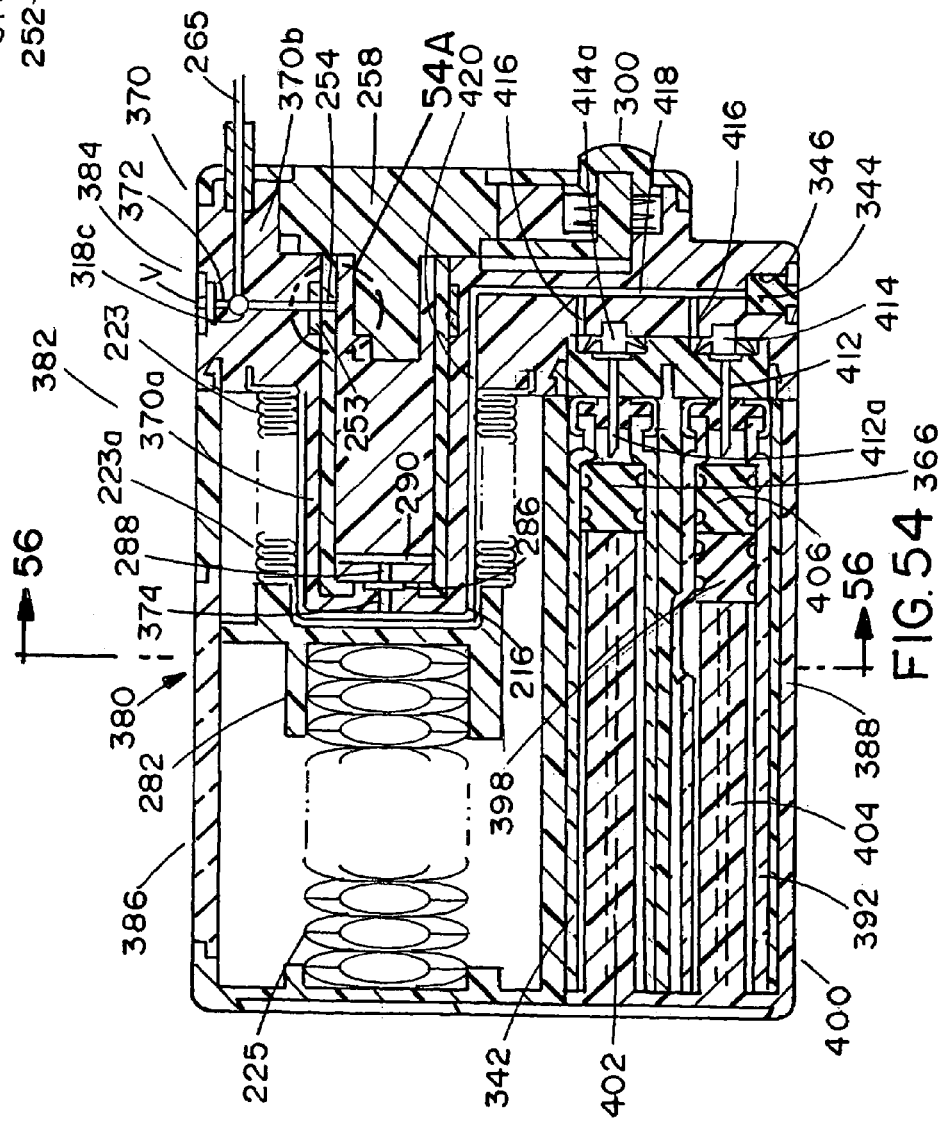

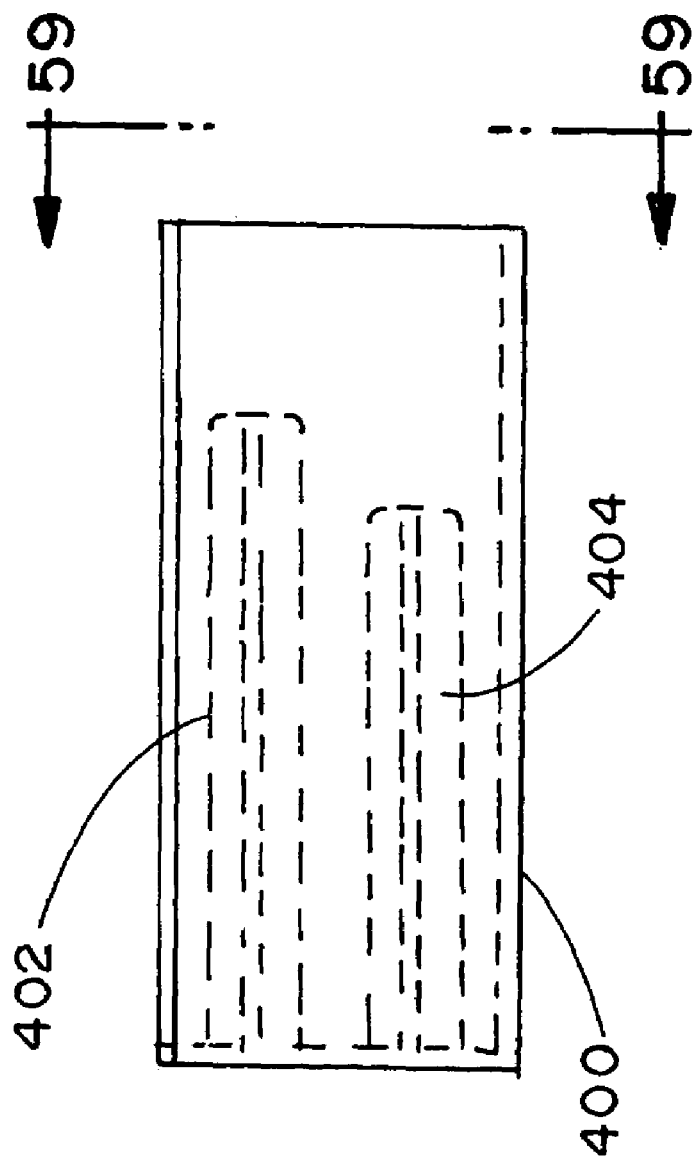

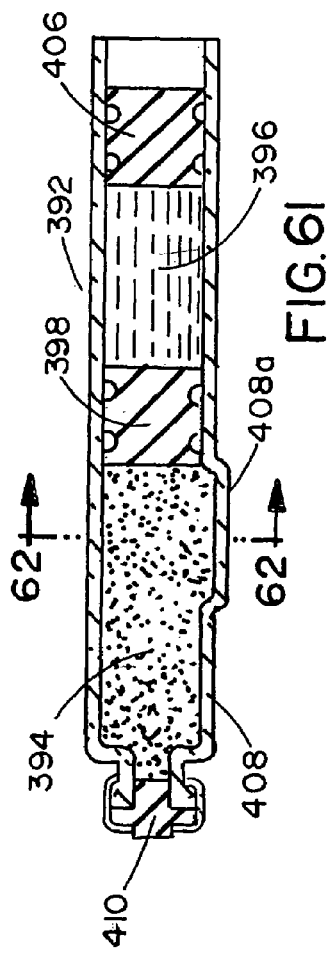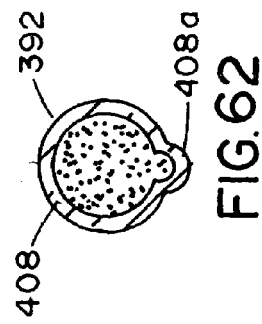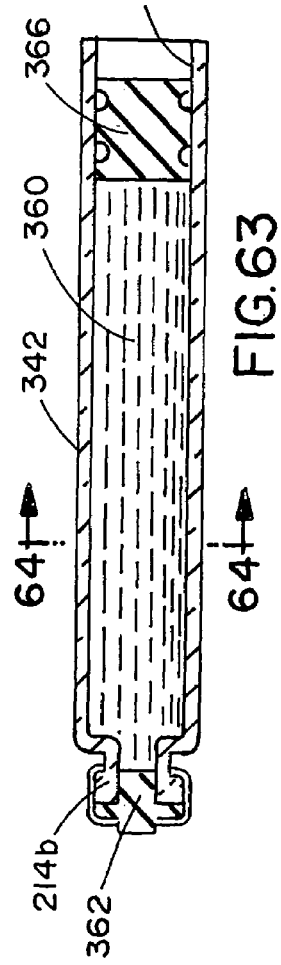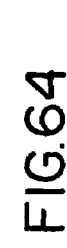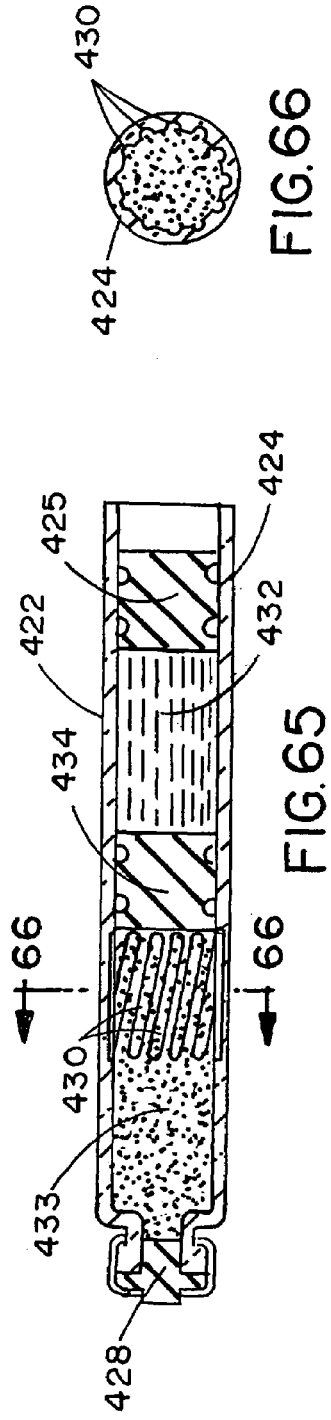

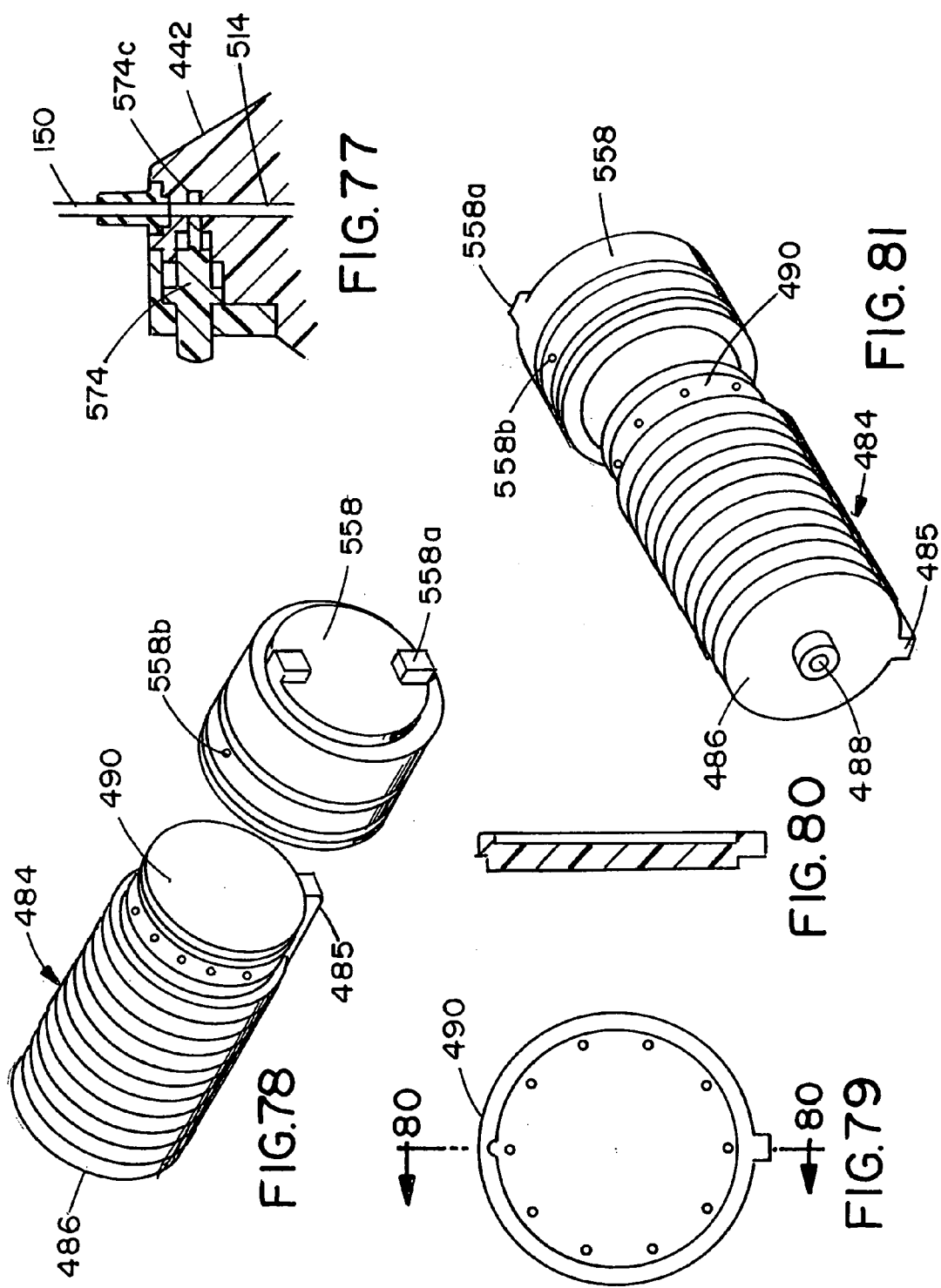

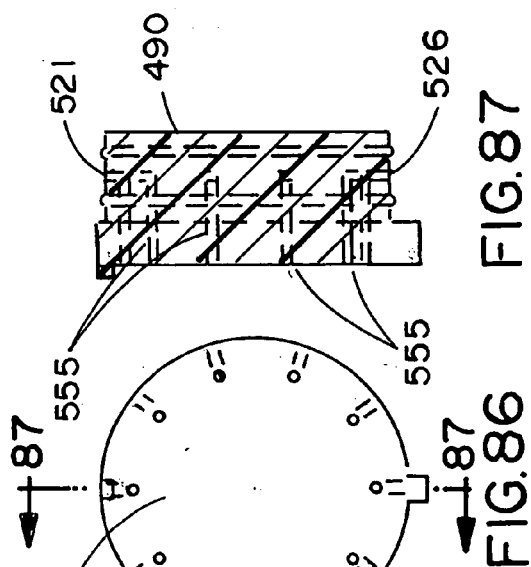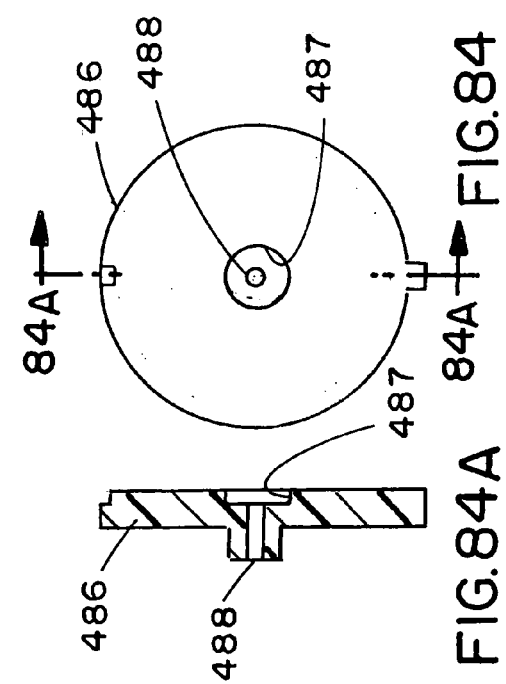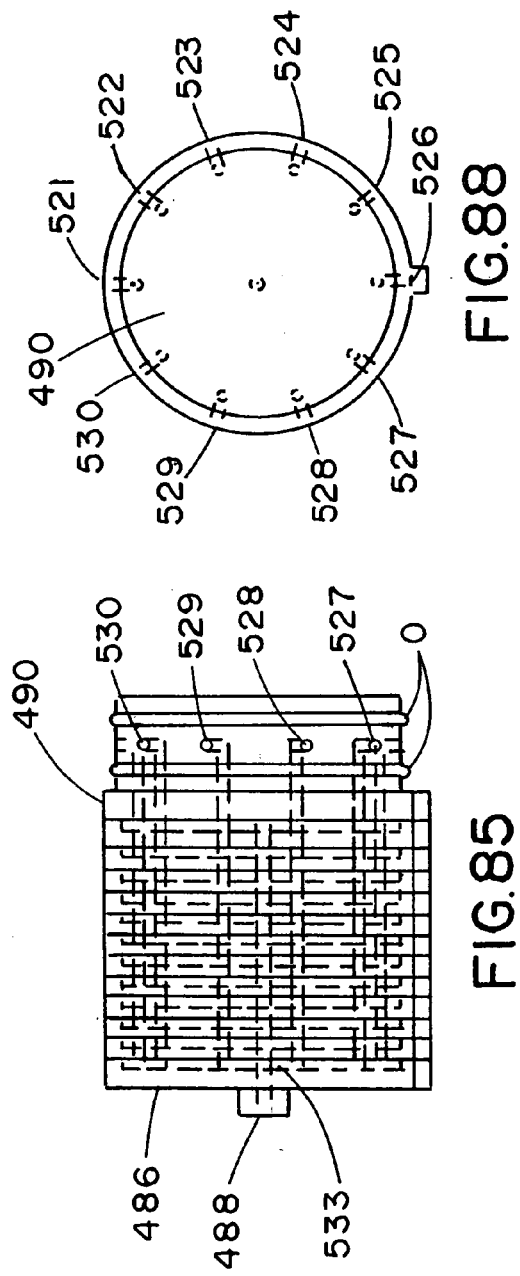

INFUSION APPARATUS

BACKGROUND OF THE INVENTION

1. Field of the Invention

The present invention relates generally to medicament infusion devices. More particularly, the invention concerns an improved apparatus for infusing medicinal agents into an ambulatory patient at specific rates over extended periods of time, which apparatus includes a novel compressible spring energy source, and a novel flow rate control means for precisely controlling the rate of fluid flow from the reservoir of the device.

2. Discussion of the Prior Art

A number of different types of medicament dispensers for dispensing medicaments to ambulatory patients have been suggested. Many of the devices seek either to improve or to replace the traditional gravity flow and hypodermic syringe methods, which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus.

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose can result in a toxic reaction.

For those patients that require frequent injections of the same or different amounts of medicament, the use of the hypodermic syringe method of delivery is common. However for each injection, it is necessary to first draw the injection dose into the syringe, then check the dose and, after making certain that all air has been expelled from the syringe, finally, inject the dose either under bolus or slow push protocol. This cumbersome and tedious procedure creates an unacceptable probability of debilitating complications, particularly for the elderly and the infirm.

As will be appreciated from the discussion, which follows, the apparatus of the present invention is uniquely suited to provide precise, continuous fluid delivery management at a low cost in those cases where a variety of precise dosage schemes are of utmost importance. An important aspect of the apparatus of the present invention is the provision of novel fill means for filling the reservoir of the device using a conventional medicament vials or cartridge containers of various types having a pierceable septum. Another unique feature of the apparatus of the present invention is the provision of various fluid flow rate control means, including an embedded microcapillary multichannel flow rate control means which enables precise control of the rate of fluid flow of the medicament to the patient. More particularly, the apparatus of the present invention includes a unique, adjustable fluid flow rate mechanism which enables the fluid contained within the reservoir of the device to be precisely dispensed at various selected rates.

The apparatus of the present invention can be used with minimal professional assistance in an alternate health care environment, such as the home. By way of example, devices of the invention can be comfortably and conveniently removably affixed to the patient's body or clothing and can be used for the continuous infusion of injectable anti-infectives, hormones, steroids, blood clotting agents, analgesics, and like medicinal agents. Similarly, the devices of the invention can be used for most I-V chemotherapy and can accurately deliver fluids to the patient in precisely the correct quantities and at extended microfusion rates over time.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a compressible-expandable spring member that provides the force necessary to substantially, uniformly dispense various solutions from standard prefilled vial containers that can be conveniently loaded into the apparatus. Because of the simplicity of construction of the apparatus of the invention, and the straightforward nature of the energy source, the apparatus can be manufactured at low cost without in any way sacrificing accuracy and reliability.

With regard to the prior art, one of the most versatile and unique fluid delivery apparatus developed in recent years is that developed by the present inventor and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to the present applicant, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a prefilled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a prefilled container which is housed within the body of the device. After having been deformed, the polymeric, elastomeric member will return to its starting configuration in a highly predictable manner.

Another important prior art fluid delivery device is described in the U.S. Pat. No. 6,063,059 also issued to the present inventor. This device, while being of a completely different construction embodies a compressible-expandable stored energy source somewhat similar to that used in the apparatus of the present invention.

Still another prior art fluid delivery device, in which the present inventor is also named as an inventor, is described in U.S. Pat. No. 6,086,561. This latter patent incorporates a fill system that makes use of conventional vials and cartridge medicament containers.

SUMMARY OF THE INVENTION

It is an object of the present invention to provide a compact fluid dispenser for use in controllably dispensing fluid medicaments, such as, antibiotics, oncolytics, hormones, steroids, blood clotting agents, analgesics, and like medicinal agents from prefilled containers at a uniform rate.

Another object of the invention is to provide a small, compact fluid dispenser that includes a housing to which fill vials can be connected for filling the dispenser reservoir with the fluid.

Another object of the invention is to provide a dispenser of in which a stored energy source is provided in the form of a compressible-expandable spring member that provides the force necessary to continuously and substantially uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser which is adapted to be used with conventional prefilled drug containers to deliver beneficial agents therefrom in a precise and sterile manner.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining in the device reservoir Another object of the invention is to provide a self-contained medicament dispenser which is of very simple construction and yet extremely reliable in use.

Another object of the invention is to provide a fluid dispenser as described in the preceding paragraphs which is easy and inexpensive to manufacture in large quantities.

BRIEF DESCRIPTION OF THE DRAWINGS

FIG. 13 is a generally perspective, exploded front view of the rate control assembly shown in FIG. 11.

FIG. 14 is a generally perspective, exploded rear view of the rate control assembly shown in FIG. 11.

FIG. 17 is a generally perspective, exploded view of an alternate form of flow rate control assembly.

FIG. 18 is a generally perspective, exploded view of yet another alternate form of the fluid flow rate assembly of the invention.

FIG. 19C is a generally diagrammatic, tabular view further illustrating various types of springs that can be used as the stored energy source of the invention.

FIG. 19F is a generally diagrammatic, tabular view further illustrating various types of springs that can be used as the stored energy source of the invention.

FIG. 22A is a cross-sectional view taken along lines 22A—22A of FIG. 22.

FIG. 23 is a cross-sectional view of one of the prefilled medicament shell vials that can be used to fill the fluid reservoir of the apparatus shown in FIG. 21.

FIG. 24 is a view taken along lines 24—24 of FIG. 23.

FIG. 35 is a generally perspective, front view of one form of the fluid flow control assembly of the apparatus of the invention.

FIG. 36 is a generally perspective, exploded front view of the fluid flow control assembly shown in FIG. 35.

FIG. 37 is a greatly enlarged, fragmentary cross-sectional view of one of the flow control channels formed in the flow control member shown in the central portion of FIG. 36.

FIG. 38 is a generally perspective, rear view of the fluid flow control assembly of the apparatus of the invention.

FIG. 39 is a generally perspective, exploded rear view of the fluid flow control assembly shown in FIG. 38.

FIG. 40 is a generally perspective view of an alternate form of the flow control member of the invention.

FIG. 40A is a generally perspective view of yet another form of the flow control member of the invention.

FIG. 41 is a front view of the assembly shown in FIG. 35.

FIG. 42 is a cross-sectional view taken along lines 42—42 of FIG. 41.

FIG. 43 is a view taken along lines 43—43 of FIG. 42.

FIG. 44 is a cross-sectional view taken along lines 44—44 of FIG. 42.

FIG. 45 is a cross-sectional view taken along lines 45—45 of FIG. 42.

FIG. 50 is an enlarged view of one of the fill vial assemblies shown in FIG. 47.

FIG. 50A is a view taken along lines 50A—50A of FIG. 50.

FIG. 51 is a generally perspective, exploded view of fluid delivery apparatus shown in FIG. 47.

FIG. 54 is an enlarged, longitudinal cross-sectional view of the embodiment of the invention shown in FIG. 53.

FIG. 54A is an enlarged, cross-sectional view of the area designated as 54A in FIG. 54.

FIG. 54B is an enlarged, cross-sectional view of the elastomeric sealing band shown in FIG. 54A.

FIG. 58 is a side view of the vial cover component of the apparatus.

FIG. 59 is a view taken along lines 59—59 of FIG. 58.

FIG. 61 is an enlarged, longitudinal, cross-sectional view of one of the fill vial assemblies shown in FIG. 54.

FIG. 62 is a cross-sectional view taken along lines 62—62 of FIG. 61.

FIG. 63 is an enlarged, longitudinal, cross-sectional view of the other fill vial assembly of the apparatus of the invention.

FIG. 64 is a cross-sectional view taken along lines 64—64 of FIG. 63.

FIG. 65 is a cross-sectional view of an alternate form of fill vial assembly of the invention.

FIG. 66 is a cross-sectional view taken along lines 66—66 of FIG. 65.

FIG. 77 is a cross-sectional view taken along lines 77—77 of FIG. 72.

FIG. 78 is a generally perspective, front view of the flow rate control means of this latest form of the apparatus of the present invention.

FIG. 79 is a rear view of the forward most rate control plate of the flow control means shown in FIG. 81.

FIG. 80 is a cross-sectional view taken along lines 80—80 of FIG. 79.

FIG. 81 is a generally perspective, rear view of the flow rate control means shown in FIG. 78.

FIG. 84 is a rear view of the first, or leftmost rate control plate of the rate control plate assembly shown in FIG. 81.

FIG. 84A is a cross-sectional view taken along lines 84A—84A of FIG. 84.

FIG. 85 is a side elevational view of the rate control plate assembly shown in FIG. 81 as it appears in an assembled configuration.

FIG. 86 is a rear view of the outlet manifold component of the assembly shown in FIG. 85.

FIG. 87 is a cross-sectional view taken along lines 87—87 of FIG. 86.

FIG. 88 is a front view of the assembly shown in FIG. 85.

FIG. 95A is an enlarged, fragmentary cross-sectional view of the upper portion of FIG. 95.

FIG. 95B is an enlarged fragmentary cross-sectional view of the lower portion of FIG. 95.

FIG. 96 is a cross-sectional view taken along lines 96—96 of FIG. 95.

FIG. 97 is a cross-sectional view similar to FIG. 96, but showing the rate control knob rotated to a second position.

DESCRIPTION OF THE INVENTION

Figure 1:
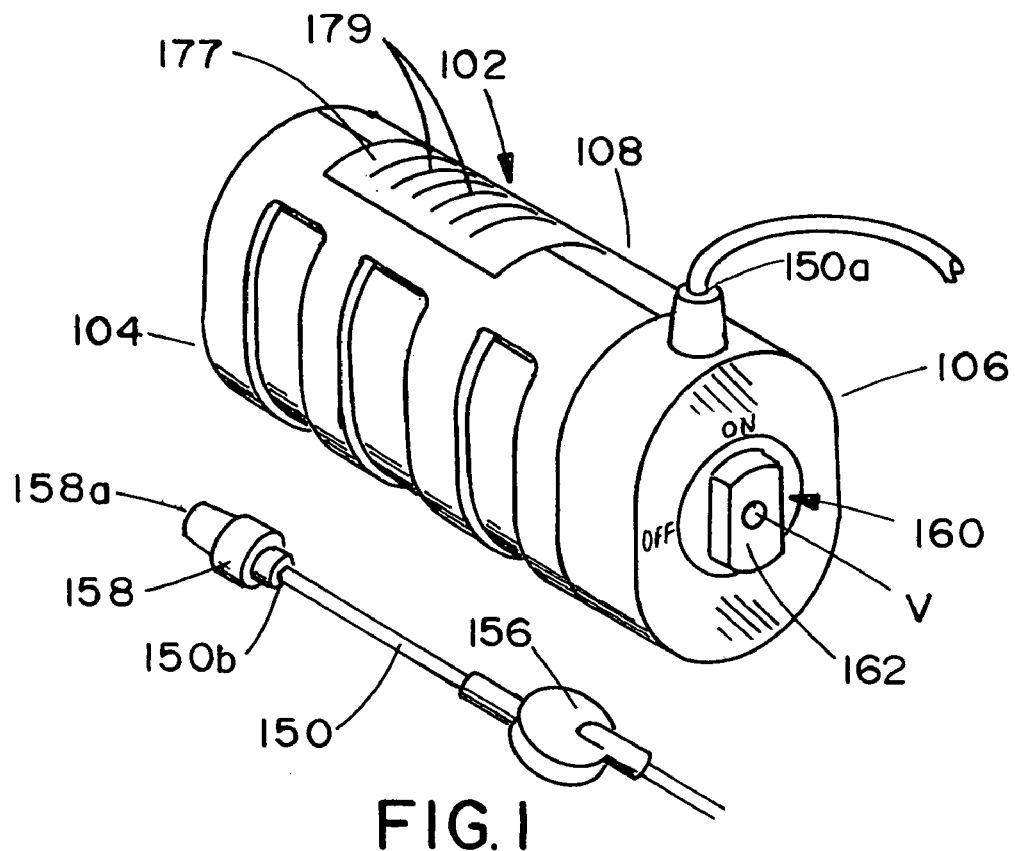
FIG. 1 is a generally perspective left front view of one embodiment of the medicament infusion apparatus of the present invention for dispensing fluids at a uniform rate.
Figure 2:
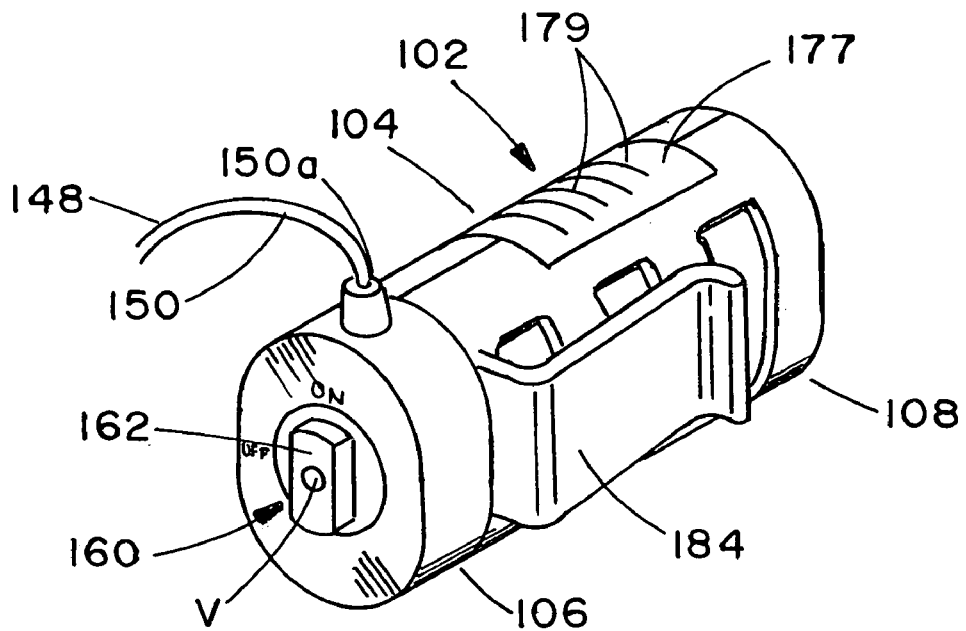
FIG. 2 is a generally perspective right front view of the embodiment of the medicament infusion apparatus shown in FIG. 1.
Figure 3:
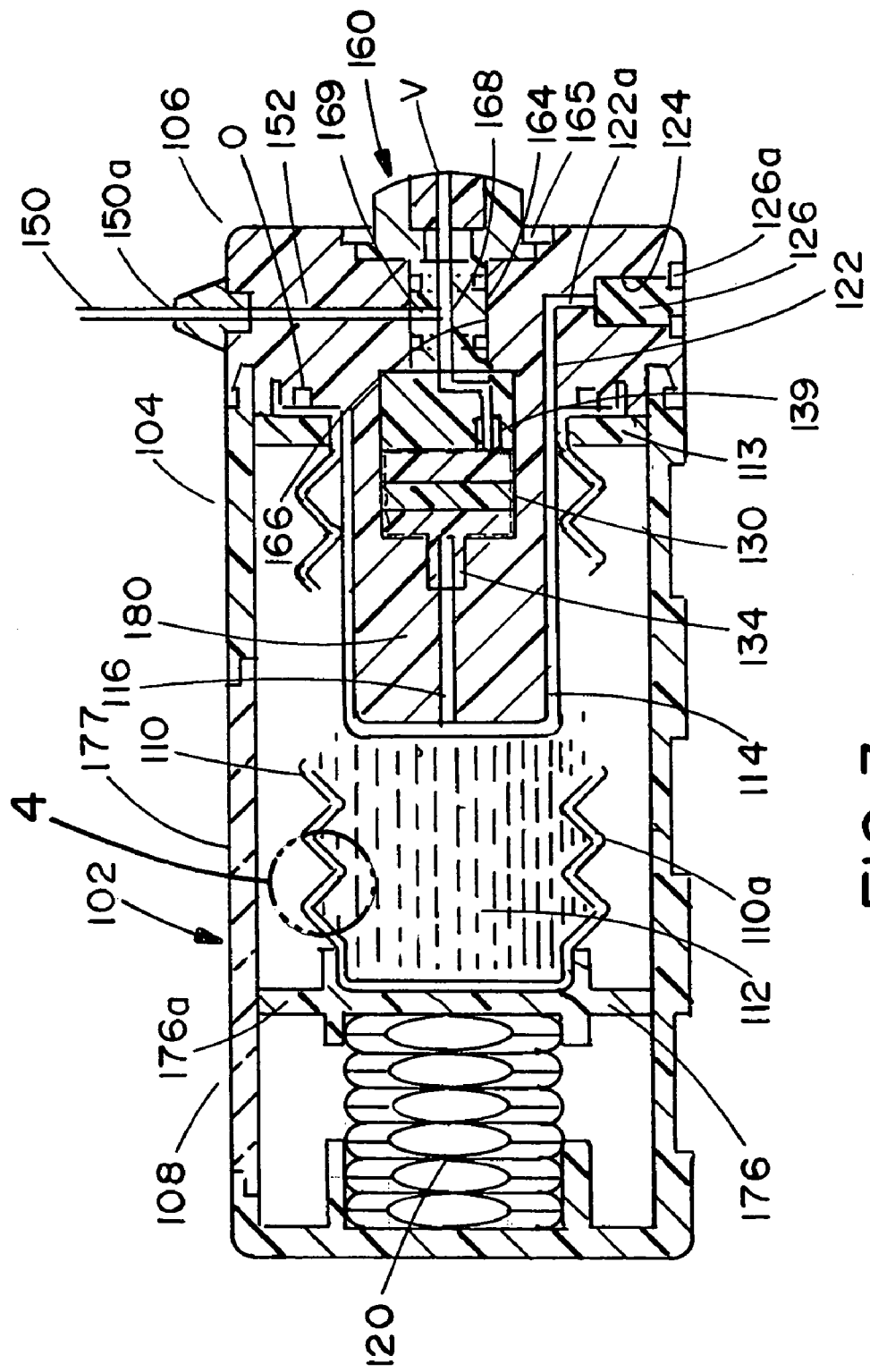
FIG. 3 is an enlarged, longitudinal cross-sectional view of the apparatus shown in FIG. 1.
Figure 4:
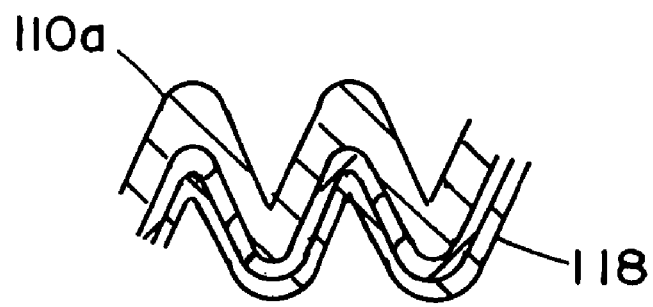
FIG. 4 is an enlarged, cross-sectional view of the area designated as "4" in FIG. 3.

Referring to the drawings and particularly to FIGS. 1 through 10, one embodiment of the dispensing apparatus of the present invention is there illustrated and generally designated by the numeral 102. As best seen in FIGS. 1 and 2, the apparatus here comprises an outer housing 104 having first and second portions 106 and 108 respectively that can be snapped together, adhesively bonded, sonic bonded or otherwise suitably interconnected. Disposed within outer housing 104 is an inner, expandable housing 110 having a fluid reservoir 112 provided with an inlet 114 (FIG. 3) for permitting fluid flow into the fluid reservoir and an outlet 116 for permitting fluid flow from the fluid reservoir. Expandable housing 110, which can be constructed from a metal or plastic material, comprises a bellows structure having an expandable and compressible, accordion-like, annular-shaped sidewall 110a, the configuration of which is best seen in FIGS. 3 and 4. As best seen in FIG. 4, the inner wall of the bellows is provided with a surface modification or protective coating 118 that is compatible with the fluids contained within reservoir 112. This coating 118 can be accomplished by several different processes. One process that is extremely clean, fast and effective is plasma processing. In particular this technique allows for any of the following: plasma activation, plasma induced grafting and plasma polymerization of molecular entities on the surface of the bellows. For cases where an inert hydrophobic interface is desired, plasma using fluorine-containing molecules may be employed. That is, the drug interface bellows surface may be cleaned with an inert gas plasma, and subsequently, a fluorine containing plasma may be used to graft these molecules to the surface. Alternatively, if a hydrophilic surface is desired (e.g. for drug solutions that are highly corrosive or in oil based solvents) an initial plasma cleaning may be done, followed by a plasma polymerization using hydrophilic monomers. Similar drug interface coatings "C" can be provided on other surfaces, such as fluid passageways, that may be encountered by the drugs that are to be delivered (see, for example, FIG. 37).

Disposed within second portion 108 of outer housing 104 is the novel stored energy means of the invention for acting upon inner expandable housing 110 in a manner to cause the fluid contained within fluid reservoir 112 to controllably flow outwardly of the housing. In the present form of the invention, this important stored energy means comprises a resiliently deformable, spring 120 that is carried within the second portion 108 of the outer housing. In a manner presently to be described spring 120 is first more fully compressed by fluid flowing into reservoir 112 and then is controllably expanded to cause fluid flow from the outer housing through the dispensing means of the invention. As depicted in FIGS. 19B through 19F and as will be discussed in greater detail hereinafter, stored energy member 120 can be constructed in various configurations and from a wide variety of materials including metals and plastics. Preferably, spring 120 takes the form of a wave spring of the type illustrated in configuration F of FIG. 19C which is readily commercially available from sources, such as the Smalley Company of Lake Zurich, Ill.

Typically, wave springs operate as load bearing devices. They can also take up play and compensate for dimensional variations within assemblies. A virtually unlimited range of forces can be produced whereby loads build either gradually or abruptly to reach a predetermined working height. This establishes a precise spring rate in which load is proportional to deflection, and can be tuned to a particular load requirement.

Typically, a wave spring will occupy an extremely small area for the amount of work it performs. The use of this product is demanded, but not limited to tight axial and radial space restraints.

Forming an important aspect of the apparatus of the present invention is fill means carried by outer housing 104 for filling the reservoir 112 with the fluid to be dispensed. As best seen in FIG. 3, first portion 106 includes a fluid passageway 122 in communication with inlet 114 of fluid reservoir 112. Proximate its lower end 122a, fluid passageway 122 communicates with a cavity 124 formed within portion 106 of the housing 104. Disposed within cavity 124 is an elastomeric, pierceable septum 126 that comprises a part of one form of the fill means of the invention. Septum 126 is held in position by a bonded retainer 126a and is pierceable by the needle of the syringe which contains the medicinal fluid to be dispensed and which can be used in a conventional manner to fill or partially fill reservoir 112 via passageway 122 and to recover unused medicament. The fill means can also be used to add adjuvant drugs.

Figure 11:
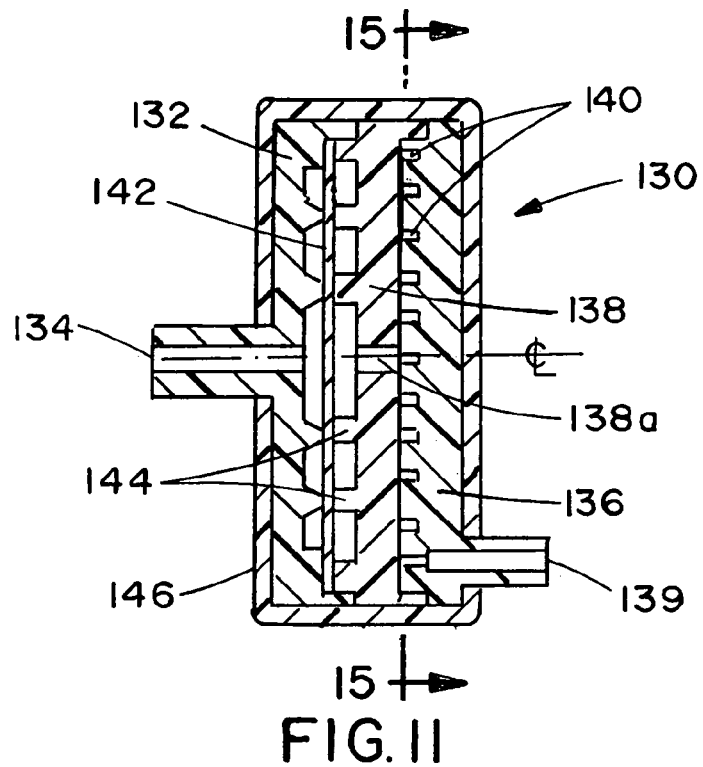
FIG. 11 is a greatly enlarged cross-sectional view of one form of the rate control assembly of the invention.
Figure 12:
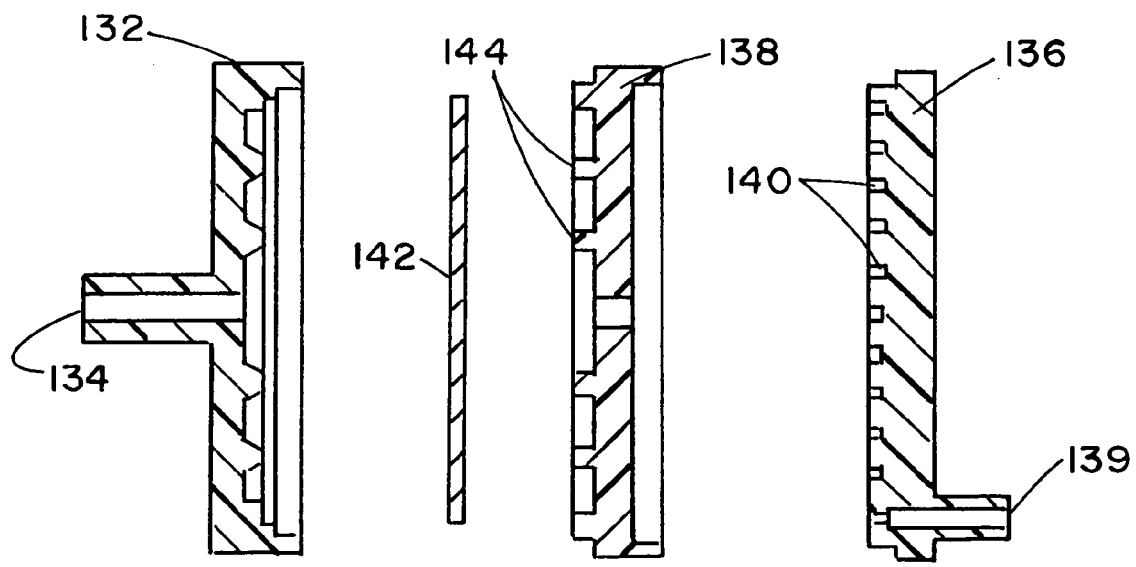
FIG. 12 is an exploded, cross-sectional view of the rate control assembly shown in FIG. 11.
Figure 16:
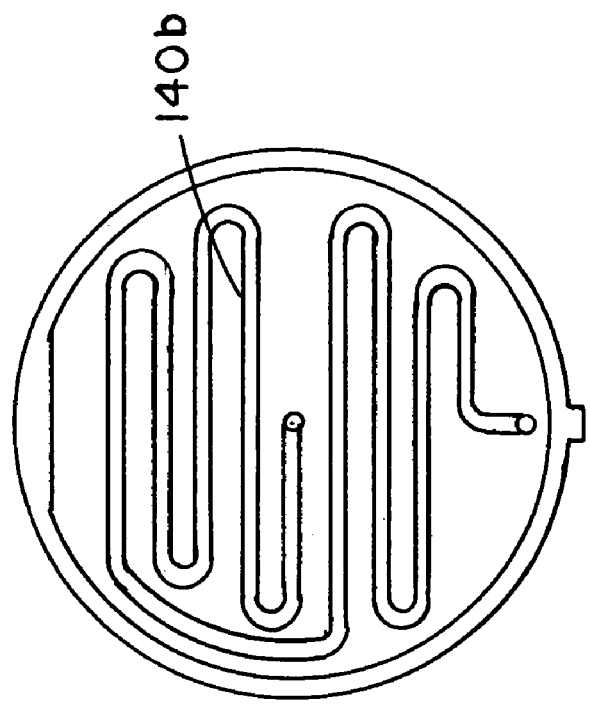
FIG. 16 is a view similar to FIG. 15, but showing an alternate form of flow rate control component.
Figure 15:
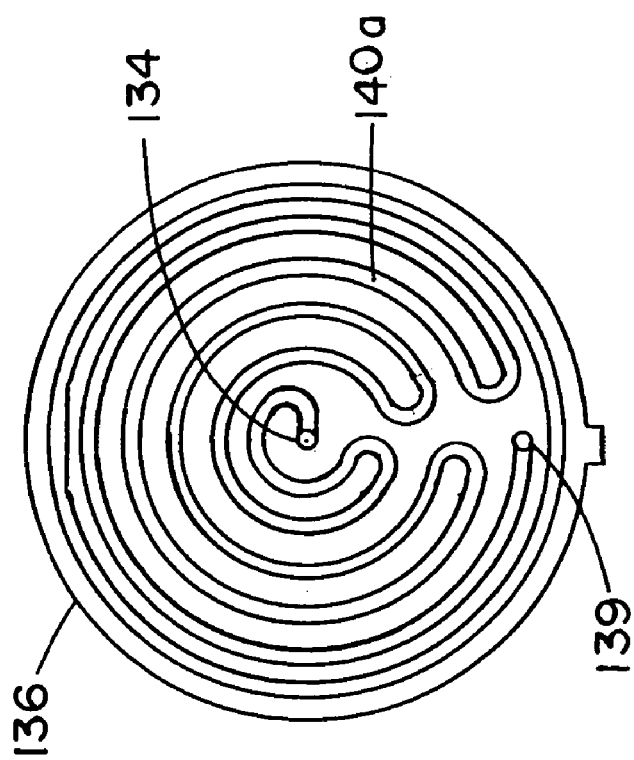
FIG. 15 is a cross-sectional view taken along lines 15—15 of FIG. 11.

Forming another very important aspect of the apparatus of the present invention is a novel fluid flow control means that is disposed interiorly of outer housing 104. This flow control means functions to precisely control the rate of fluid flow outwardly from reservoir 112 and toward the patient. In the form of the invention shown in FIGS. 1 through 19 the flow control means comprises a flow control assembly generally designated in the drawings by the numeral 130. As best seen in FIGS. 11 and 12, this novel flow control assembly here comprises an inlet manifold 132 having an inlet port 134 that is in communication with the outlet 116 of reservoir 112 and an outlet manifold 136 that is interconnected with intake manifold 132 by means of a separator plate 138. As indicated in FIGS. 11 and 12, outlet manifold 136 as an outlet port 139 that is in communication with the outlet of the apparatus and is provided an elongated microchannel 140 that is in communication both with inlet port 134 and with outlet port 139 of the outlet manifold. Disposed intermediate inlet manifold 132 and a generally circular shaped separator plate 138 is filter means here provided as a filter member 142 that functions to filter fluid flowing toward outlet port 139 of the outlet manifold. Generally disk shaped filter member 142 can be formed from various porous materials, including porous poly propolene. Filter number 142 can be bonded or otherwise suitably fixed in place.

As best seen in FIG. 13, separator plate 138 is provided with standoff ribs 144 for supporting filter member 142 in the manner shown in FIG. 11. The assemblage made up of inlet manifold 132, outlet manifold 136, separator plate 138 and filter 142 is preferably encapsulated within an outer metal or plastic casing 146 (see FIG. 11).

As indicated in FIG. 11, the flow rate control means, or assemblage 130, has an axial centerline "CL" with which the inlet port 134 of the inlet manifold 132 is coaxial aligned. However, the outlet port 139 of the outlet manifold is radially spaced from the axial centerline. With this construction, fluid will flow from reservoir 112 into inlet port 134, through filter member 142, through a central opening 138a formed in a separator plate and thence into microchannel 140. By controlling the length, depth and width of the microchannel 140, the rate of fluid flow flowing outwardly of outlet 139 can be precisely controlled. In this regard, the microchannel can take several forms as, for example, those illustrated in FIGS. 15 and 16 of the drawings and generally designated therein by the numerals 140a and 140b.

Turning once again to FIGS. 1, 2 and 3, also forming a part of the infusion apparatus of the present invention is dispensing means for dispensing fluid to the patient. In the present form of the invention this dispensing means comprises an administration set 148 that is connected to the first portion 106 of housing 104 in the manner shown in the drawings. The proximal end 150a of administration line 150 of the administration set 148 is in communication with an outlet fluid passageway 152 which is formed in housing portion 106 in the manner best seen in FIG. 3. Disposed between the proximal end 150a and the distal end 150b of the administration line is a conventional gas vent and particulate filter 156. Provided at the distal end 150b is a luer connector 158 and cap 158a of conventional construction (FIG. 1).

Figure 5:
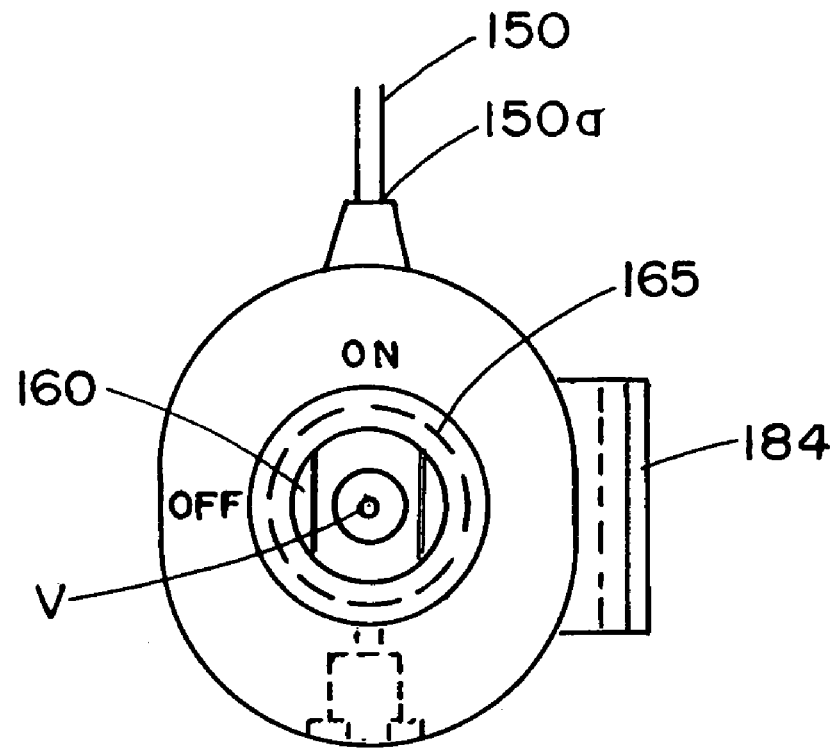
FIG. 5 is a right end view of the apparatus shown in FIG. 3.
Figure 6:
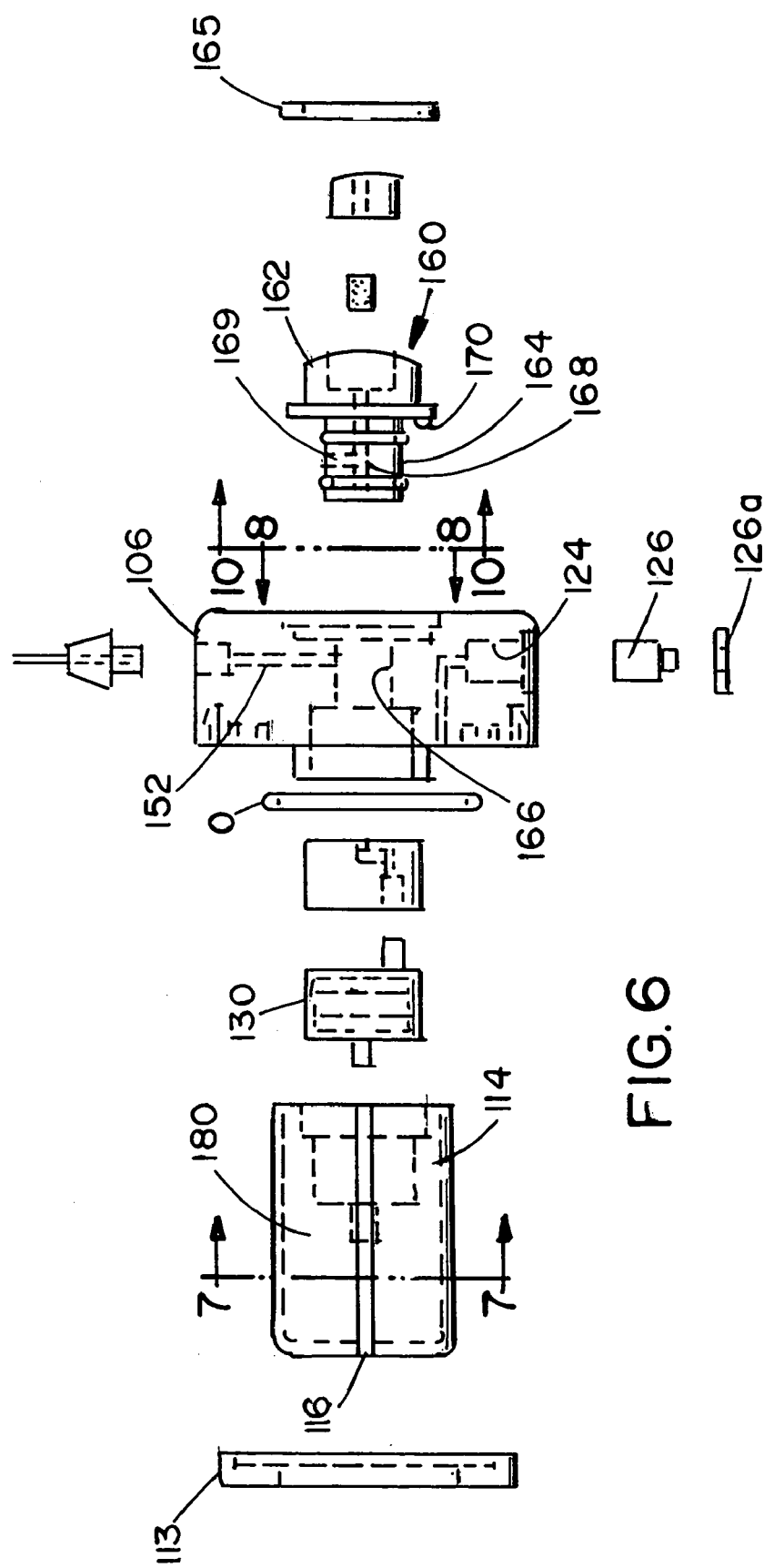
FIG. 6 is an exploded view of the forward portion of the apparatus shown in FIG. 3.
Figure 7:
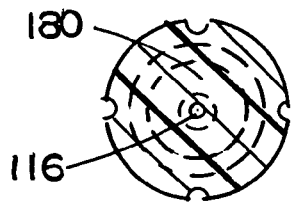
FIG. 7 is a cross-sectional view taken along lines 7—7 of FIG. 6.
Figure 8:
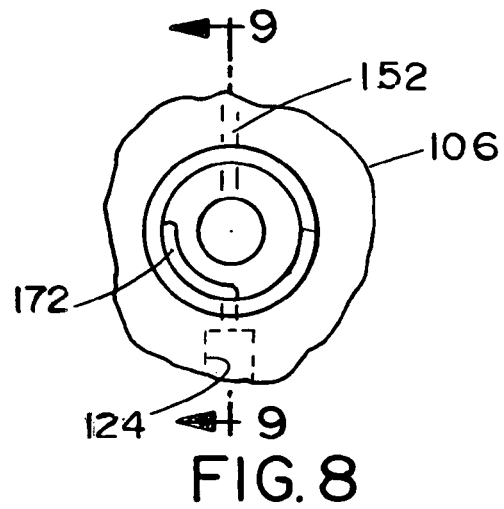
FIG. 8 is a view taken along lines 8—8 of FIG. 6.
Figure 9:
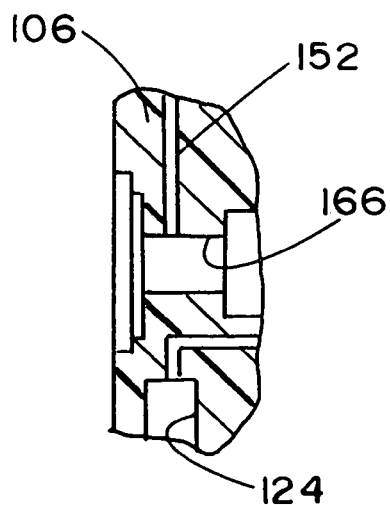
FIG. 9 is a cross-sectional view taken along lines 9—9 of FIG. 8.
Figure 10:
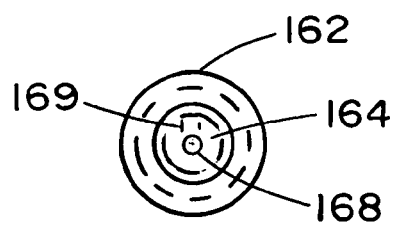
FIG. 10 is a view taken along lines 10—10 of FIG. 6.

To control fluid flow from the outlet 139 of the flow rate control means toward outlet passageway 152, novel operating means are provided. This operating means here comprises a control knob assembly 160 that includes a finger gripping portion of 162 and a generally cylindrically shaped shank portion 164 that is rotatably received within a bore 166 formed in housing portion 106 (FIG. 3). O-rings, generally designated as "O", function to sealably interconnect the various operating components. As indicated in FIG. 5, control knob assembly 160 is rotatable from a first "on", or fluid flow position, to a second "off" position as indicated by indicia provided on the forward face of housing portion 106. The control knob assembly is retained in position within a housing 106 by a retainer ring 165. Shank portion 164 of the control knob assembly includes an axial flow passageway 168 that communicates with the earlier identified outlet flow passageway 152 via a stub passageway 169. The flow passageway 168 also communicates with outlet 139 of flow rate control assembly 130 when the control assembly is in the "on" position shown in FIG. 5. In this position, fluid it can flow from reservoir 112, through outlet 116, through flow rate control assembly 130, into central passageway 168 of the control knob assembly and then toward the administration set via passageway 152. As indicated in FIGS. 6 and 8, to guide the travel of the control knob assembly, the control knob assembly is provided with a protuberance 170 that travels within a groove 172 provided in the housing portion 106.

In using the apparatus of the invention, with the control knob assembly in the "off" position, the reservoir 112 of the bellows component 110 can be filled by filling means which comprises a conventional syringe having a needle adapted to pierce the pierceable septum 126 which is mounted within portion 106 of the apparatus housing. As the fluid flows into the bellows reservoir, the bellows will be expanded from a collapsed into an expanded configuration such as shown in FIG. 3. As the bellows member expands it will urge a telescopically movable volume indicator member 176 that is carried within a second portion 108 of the housing and in engagement with the stored energy source, or spring member 120 causing it to compress. As the reservoir 112 fills with fluid from the filling syringe, any gases trapped within the reservoir will be vented to atmosphere via vent means "V" mounted in control knob assembly 160. A seal ring 113 (FIG. 3), prevents leakage of fluid between bellows 110 and portion 106 of the housing.

With the infusion apparatus interconnected with the patient's clothing by means of a spring clip assembly 184, which is affixed to the side of the device housing in the manner shown in FIGS. 2 and 5, and with the administration set 148 interconnected with the patient, opening the fluid delivery path to the administration set can be accomplished by rotating the control knob from the "off" position to the "on" position. Upon opening the fluid delivery path, the stored energy means, or spring member 120, will tend to return to its precompressed or less compressed starting configuration thereby controllably urging fluid flow outwardly of reservoir 112 via the flow rate control means of the invention, passageway 168 of the control knob assembly and delivery passageway 152 formed in housing portion 106. As the fluid flows outwardly of the apparatus due to the urging of the stored energy means, the bellows structure 110 will be collapsed and at the same time member 176 will travel inwardly of housing portion 108. Coupling member 176, which forms a part of the volume indicator means of the invention, includes a radially outwardly extending indicating finger 176a that is visible through a volume indicator window 177 that is provided in a second portion 108 of the apparatus housing and also comprises a part of the volume indicator means of the invention (FIG. 1 and 2). Indicia 179, which are provided on indicator window 177, function to readily indicate to the caregiver the amount of fluid remaining within bellows fluid reservoir 112. Housing portion 106 includes an inwardly extending ullage portion 180 that functions to ensure that substantially all of the medicinal fluid contained within the bellows reservoir will be expelled therefrom.

As previously discussed, a number of beneficial agents can be introduced into reservoir 112 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Referring next to FIG. 17, an alternate form of flow control means of the invention is there shown. This flow control means can be mounted within housing 104 in place of flow control assembly 130 and functions to precisely control the rate of fluid flow from reservoir 112 toward the patient. In the form of the invention shown in FIG. 17, the flow control means comprises a flow control assembly generally designated in the drawings by the numeral 180. Flow control assembly 180 here comprises a first component or inlet manifold 180a having an inlet port 183 that can be placed in communication with the outlet 116 of the fluid reservoir 112 and an outlet manifold 180b that can be interconnected with first component 180a by means of a pair of separator plates or components 181 and 182. Outlet manifold component 180b has an outlet port 181 that is in communication with the outlet 182a of separator plate 182 and also in communication with the outlet of the apparatus. Intake manifold 180a has an inner surface that is provided with a plurality of interconnected imbedded capillaries 184. Capillaries 184 have input and output channels 184a that are in communication both with inlet port 183 and with an outlet port 185 formed in the inlet manifold. These input and output channels are typically substantially larger than the intermediate rate control channels. Disposed adjacent manifold 180a is separator plate 181. Separator plate 181 has an inner surface that is also provided with a plurality of imbedded capillaries 186 that also have larger input and output channels 186a that are in communication with outlet port 185 formed in the inlet manifold. Fluid flowing from capillaries 184 flows into capillaries 186 via an inlet port 181a and then outwardly of separator plate 181 via an outlet port 181b.

Separator plate 182, which is disposed intermediate separator plate 181 and outlet manifold 180b, has an inner surface that is provided with a plurality of interconnected capillaries 187 that receive the fluid flowing outwardly of outlet port 181b. After the fluid flow through capillaries 187, it will flow toward outlet 181 of outlet manifold 180b via outlet port 182a. Capillaries 187 also have larger input and output channels 187a. The various components that male up the flow control assembly are preferably adhesively bonded together. It is to be noted that the rear surfaces of the plates are planar and cooperate with the capillaries to form fluid flow passageways.

By controlling the length and depth of capillaries 184, 186, and 187, the rate of fluid flow flowing outwardly of outlet 181 can be precisely controlled. In this regard, it is to be understood that the capillaries of the flow control assembly can take several forms and be of various sizes depending upon the end use of the fluid delivery device.

Thermal bonding may be performed by using a channeled plate and an adjacent planar surface plate that are of similar polymeric materials. In this case the two plates are placed in contact with one another confined mechanically and heated 2–5° C. above their glass transition temperatures. Following a holding period sufficient enough for the polymer molecules of the two surface interpenetrate with one another, the temperature is slowly reduced and a stress free bonded interface with imbedded microchannels is yielded. The bonding material or adhesive may be of the thermo-melting variety or of the liquid or light curable variety for thermo-melting adhesives, the adhesive material is melted into the two opposed surfaces, thereby interpenetrating these surfaces and creating a sealed channel structure.

Liquid curable bonding materials or adhesives and light curable bonding materials or adhesives may be applied to one of the surfaces of one of the plates. Subsequently, the other surface is brought into contact with the coated surface and the adhesive is cured by air exposure or via irradiation with a light source. Liquid curable bonding materials or adhesives may be elastomeric (e.g. thermoplastic elastomers, natural or synthetic rubbers, polyurethanes and silicones). Elastomeric bonding materials may or may not require pressure to seal the channel system. They may also provide closure and sealing to small irregularities in the opposed surface of the channel system.

A channel system may be formed and sealed in cases where two surfaces are being joined and one of the surfaces has one or more apertures. In order to promote bonding between these two surfaces, a vacuum may be applied to the apertures. Bonding may then be accomplished by thermal methods or after previously having applied a bonding material or adhesive.

Reference should also be made to U.S. Pat. Nos. 6,182,733; 6,555,067; 6,425,972; 5,882,465; 4,999,069; and 5,376,252 which describe various bonding techniques. Reference should also be made to Publication No. WO99/56954 and WO94/29400. It should also be understood that alternate bonding techniques such as sonic welding and laser thermal bonding techniques can be used.

Turning now to FIG. 18, still another form of flow control means of the invention is there shown. This flow control means can also be mounted within housing 104 in place of flow control assembly 130 and functions to precisely control the rate of fluid flow from reservoir 112 toward the patient. In the form of the invention shown in FIG. 18, the flow control means comprises a bonded-flow, laminate-stack control assembly generally designated in the drawings by the numeral 190. Flow control assembly 190 here comprises a first component or inlet manifold 190a having an inlet port 191 that can be placed in communication with the outlet 116 of the fluid reservoir 112 (FIG. 3) and a second component or outlet manifold 190b that can be interconnected with intake manifold 190a by means of a separator component or plates 192 and 193. Outlet manifold 190b has an outlet port 194 that is in communication with the outlet 195a of separator plate 193 and also in communication with the outlet of the apparatus. Intake manifold 190a has an inner surface that is provided with a plurality of interconnected imbedded capillaries 196. Capillaries 196 are in communication both with inlet port 191 and with an outlet port 197 formed in the inlet manifold. Disposed adjacent manifold 190a is the separator plate 192. Separator plate 192 has an inner surface that is provided with a plurality of imbedded capillaries 198 that are in communication with outlet port 197 formed in the inlet manifold. Fluid flowing from capillaries 196 flows into capillaries 198 via an inlet port 197 and then outwardly of separator plate 192 via an outlet port 200.

Separator plate 195, which is disposed intermediate separator plate 192 and outlet manifold 190b, has an inner surface that is provided with a plurality of interconnected capillaries 201 that receive the fluid flowing outwardly of outlet port 200. After the fluid flows through capillaries 201 it will flow toward outlet 194 of outlet manifold 190b via an outlet port 195a.

As before, by controlling the length, depth and width of capillaries 196, 198 and 201, the rate of fluid flow flowing outwardly of outlet 194 can be precisely controlled. It is to be noted that the rear surfaces of the plates are planar and cooperate with the capillaries to form fluid flow passageways.

Figure 19:
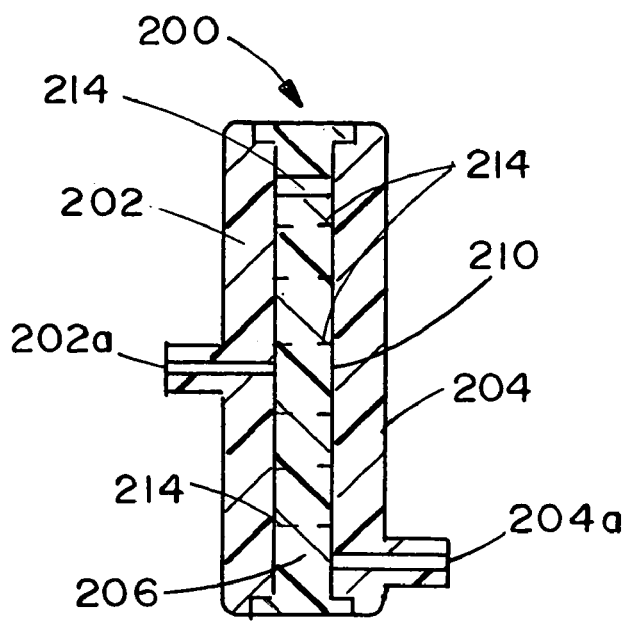
FIG. 19 is a cross sectional view of still another form of the fluid rate control assembly of the invention.
Figure 19A:
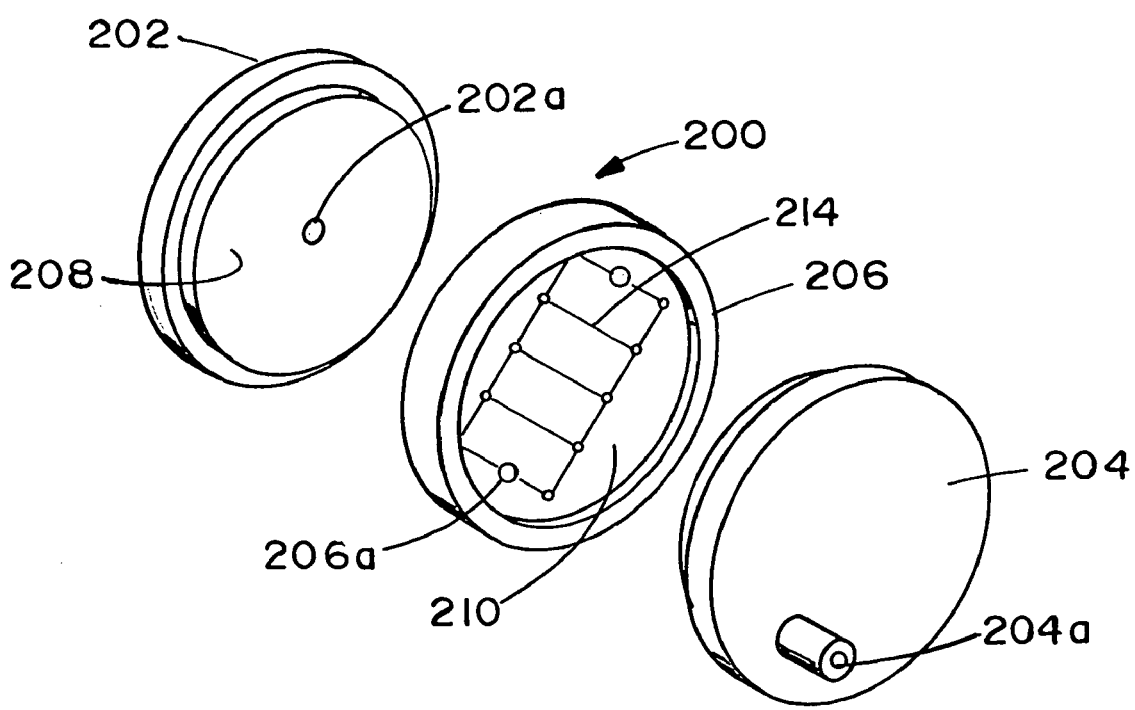
FIG. 19A is an exploded perspective view of the rate control assembly shown in FIG. 19.
Figure 19B:
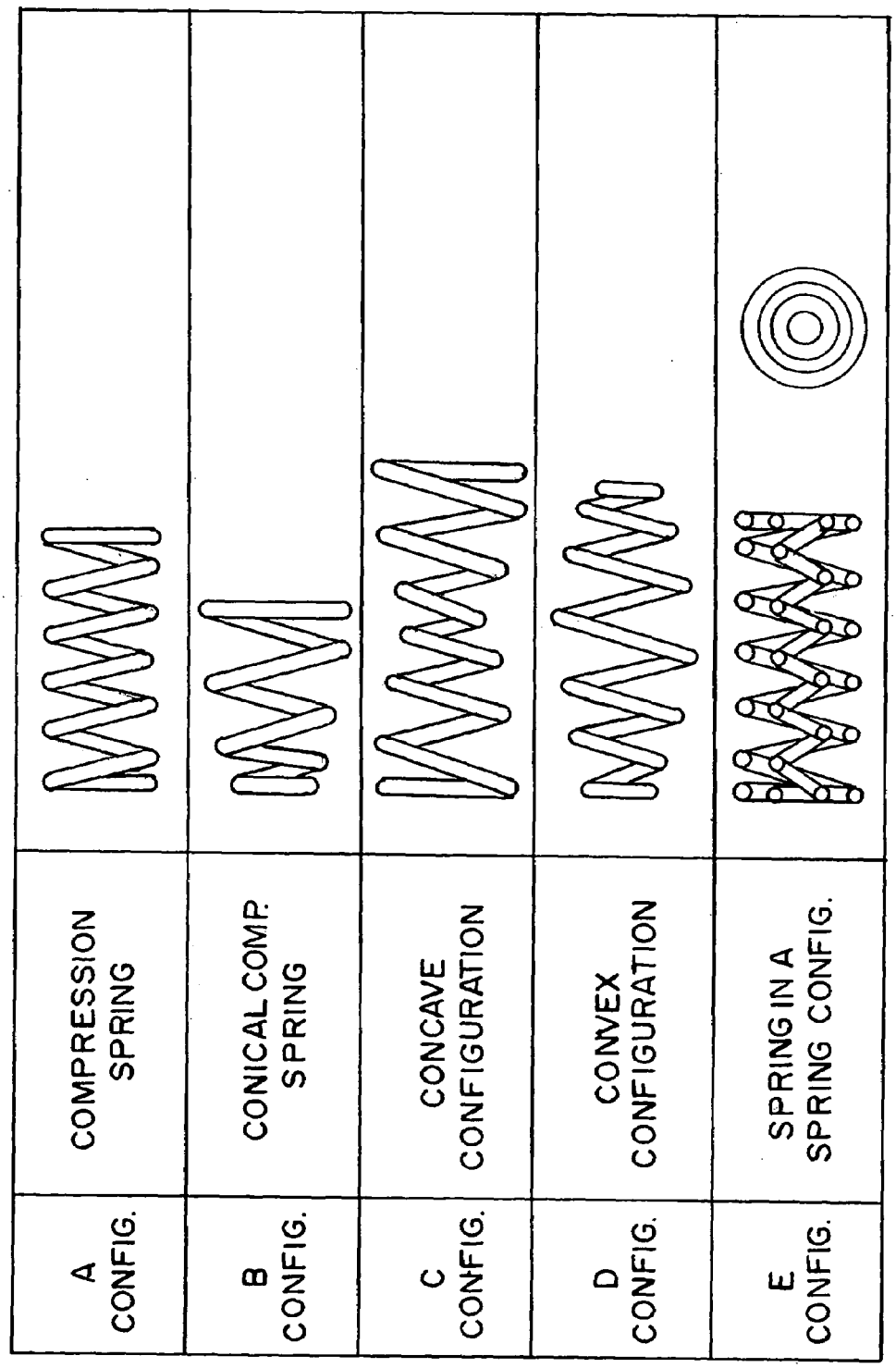
FIG. 19B is a generally diagrammatic, tabular view illustrating various types of springs that can be used as the stored energy source of the invention.

Referring next to FIGS. 19 and 19A, yet another form of flow control means of the invention is there shown. This flow control means can also be mounted within housing 104 in place of flow control assembly 130 and functions to precisely control the rate of fluid flow from reservoir 112 toward the patient. In the form of the invention shown in FIGS. 19 and 19A, the flow control means comprises a flow control assembly generally designated in the drawings by the numeral 200. Flow control assembly 200 here comprises a first component or inlet manifold 202 having an inlet port 202a that can be placed in communication with the outlet 116 of the fluid reservoir 112 and a second component or outlet manifold 204 that can be interconnected with intake manifold 202 by means of a separator component or plate 206. Outlet manifold 204 has an outlet port 204a that is in communication with the outlet 206a of separator plate 206 and also in communication with the outlet of the apparatus. Separator plate 206 has first and second opposing surfaces 208 and 210, each of which is provided with a plurality of interconnected, laser-etched capillaries 214. Capillaries 214 are in communication both with inlet port 202a and with an outlet port 204a formed in the outlet manifold. As illustrated in FIG. 19, the inner surfaces of the inlet and outlet manifold cooperate with the capillaries to form fluid flow channels through which the medicinal fluid flows.

Referring once again to FIGS. 19B and through 19F, the various types of springs suitable for use as the stored energy source of the invention are there illustrated and described. By way of background, springs are unlike other machine/structure components in that they undergo significant deformation when loaded and their compliance enables them to store readily recoverable mechanical energy.

With respect to the specific spring configurations shown in the drawings, the following discussion amplifies the descriptive notations in the drawings.

Compression Springs:

Compression springs are open-wound helical springs that exert a load or force when compressed. They may be conical or taper springs, barrel or convex, concave or standard cylindrical in shape. Further, they may be wound in constant or variable pitch. The ends can be closed and ground, closed but unground, open and unground and supplied in alternate lengths. They also can include a configuration where a second compression spring of similar or different performance characteristics which can be installed inside the inside diameter of their first compression spring, i.e., a spring in a spring.

Many types of materials can be used in the manufacture with compression springs including: Commercial Wire (BS5216 HS3), Music Stainless Steel, Phosphur Bronze, Chrome Vanadium, Monel 400, Inconel 600, Inconel X750, Nimonic 90: Round wire, Square and Rectangular sections are also available. Exotic metals and their alloys with special properties can also be used for special and applications; they include such materials as beryllium copper, beryllium nickel, niobium, tantalum and titanium.

Compression springs can also be made from plastic including all thermoplastic materials used by custom spring winding service providers. Plastic springs may be used in light-to-medium duty applications for quiet and corrosion-resistant qualities.

Wave Spring:

Multiwave compression springs, an example of which is shown as "F" in FIG. 19C are readily commercially available from sources, such as the Smalley Company of Lake Zurich, Ill. As previously discussed, such springs operate as load-bearing devices. They can take up play and compensate for dimensional variations within assemblies. A virtually unlimited range of forces can be produced whereby loads built either gradually or abruptly to reach a predetermined working height. This establishes a precise spring rate in which load is proportional to deflection, and can be turned to a particular load requirement.

Typically, a wave spring will occupy an extremely small area for the amount of work it performs. The use of this product is demanded, but not limited to tight axial and radial space restraints.

Figure 19D:
FIG. 19D is a generally diagrammatic, tabular view further illustrating various types of springs that can be used as the stored energy source of the invention.
Figure 19E:
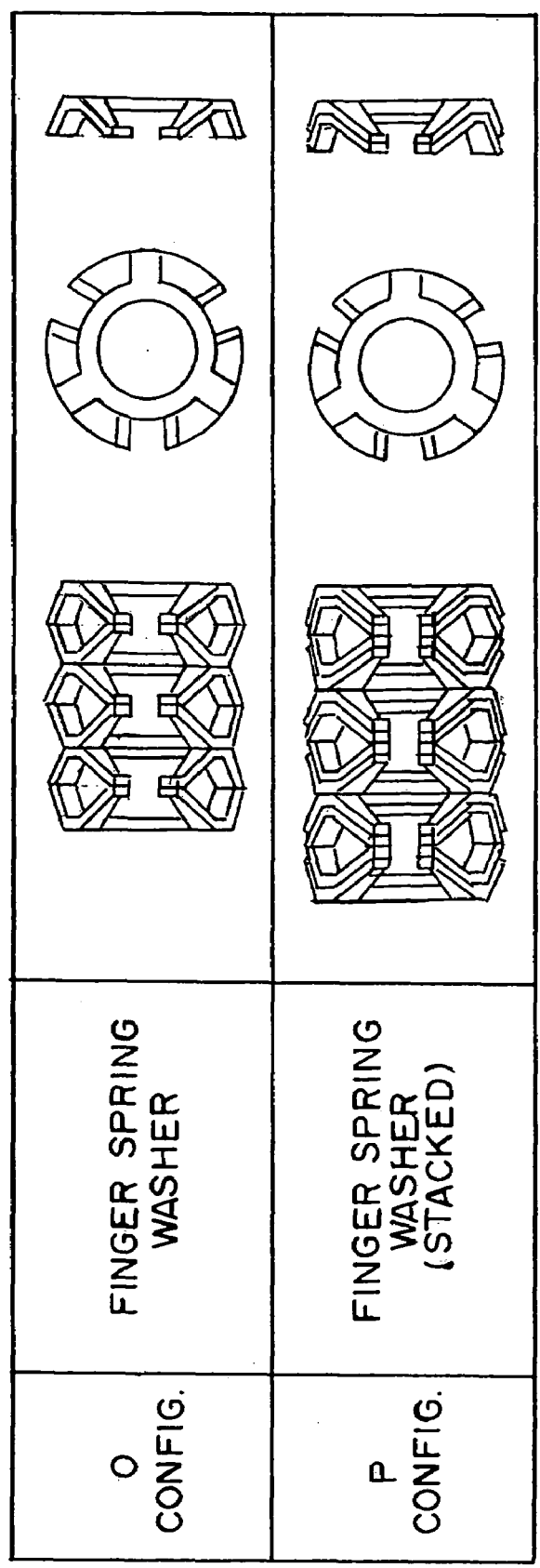
FIG. 19E is a generally diagrammatic, tabular view further illustrating various types of springs that can be used as the stored energy source of the invention.

Disc Springs:

Disc springs I, J, K, and L of FIGS. 19C and 19D compare conically shaped annular discs (some with slotted or fingered configuration) which when loaded in the axial direction, change shape. In comparison to other types of springs, disc springs product small spring deflections under high loads.

Some examples of the disc-shaped compression springs include a single or multiple stacked Belleville washer configuration as shown in G and H of FIG. 19C, and depending on the requirements of the design (flow rate over time including bolus opportunity) one or more disc springs can be used and also of alternate individual thicknesses. Alternate embodiments of the basic disc spring design in a stacked assembly can be also utilized including specialty disc springs similar to the Belleville configuration called K disc springs manufactured by Adolf Schnorr GM8H of Singelfingen, Germany, as well as others manufactured by Christian Bauer GMBH of Welzheim, Germany.

Disc springs combine high energy storage capacity with low space requirement and uniform annular loading. They can provide linear or nonlinear spring loadings with their unique ability to combine high or low forces with either high or low deflection rates. They can be preloaded and under partial compression in the design application.

All these attributes, and more, come from single-component assemblies whose nontangle features (when compared to wirewound, compression springs) make them ideal for automatic assembly procedures.

With respect to the various springs discussed in the preceding paragraphs, it is to be understood that many alternate materials can be used in the design and application of disc springs and include carbon steel, chrome vanadium steel, stainless steel, heat resistant steels, and other special alloys such as nimonic, inconel, and beryllium copper. In some special applications, plastic disc springs designs can be used.

It should be further observed that, in comparison to other types of springs, disc springs produce small spring deflections under high loads. The ability to assemble disc springs into disc spring stacks overcomes this particular limitation. When disc springs are arranged in parallel (or nested), the load increases proportionate to the number of springs in parallel, while when disc springs are arranges in series (alternately) the travel will increase in proportion to the number of springs serially arranged. These assembly methods may be combined in use.

One special feature of the disc spring is, undoubtedly, the fact that the load/deflection characteristic curve can be designed to produce a wide variety of possibilities. In addition to practically linear load/deflection characteristic curves, regressive characteristics can be achieved and even disc springs which exhibit increasing spring deflection while the corresponding disc spring load is decreasing are readily available.

Slotted disc springs present a completely different case. Slotting changes the load/deflection characteristic of the single disc spring, providing larger spring deflections for greatly reduced loads. The slotted part is actually functioning as a series of miniature cantilever arms. In some cases the stacked, slotted disc spring, as shown in the clover dome design, will also produce a non-linear, stress strain curve with a noticed flat region (force/deflection). Application and use of this type of spring operating in this region will provide a near constant force between 15% and 75% of compression.

As before, by controlling the length and depth and width of capillaries 214, the rate of fluid flow flowing outwardly of outlet 204a can be precisely controlled.

Turning next to FIGS. 20 through 45, an alternate embodiment of the infusion device of the present invention is there illustrated and generally designated by the numeral 221. As best seen in FIGS. 21A and 21B, the apparatus here comprises an outer housing 222 having first, second and third portions 222a, 222b and 222c respectively. Disposed within outer housing 222 is an inner, expandable housing 223 having a fluid reservoir 224 (FIG. 22) provided with an inlet 224a (FIG. 22) for permitting fluid flow into the fluid reservoir and an outlet 224b for permitting fluid flow from the fluid reservoir. Expandable housing 223, which can be constructed from a metal or plastic material and can include a coating of the character previously described, comprises a bellows structure having an expandable and compressible, accordion-like, generally annular-shaped sidewall 223a, the configuration of which is best seen in FIGS. 21A and 21B. It is to be understood that the bellows can be constructed in various configurations and, for example, can also be generally rectangular in cross-section.

Disposed within second portion 222b of outer housing 222 is the novel stored energy means of the invention for acting upon inner expandable housing 223 in a manner to cause the fluid contained within fluid reservoir 224 to controllably flow outwardly of the housing. In the present form of the invention, this important stored energy means comprises a compressively deformable, spring member 225 that is carried within the second portion 222b of the outer housing. In a manner presently to be described spring member 225 is further compressed from its initial state by fluid flowing into reservoir 224 and then is controllably expanded to cause fluid flow from the outer housing through the dispensing means of the invention. Stored energy member 225 can be constructed from a wide variety of materials including spring steel and plastic.

Forming an important aspect of the apparatus of this latest form of the invention is fill means carried by the third portion 222c of outer housing 222 for filling the reservoir 224 with the fluid to be dispensed. As best seen in FIG. 21A, third portion 222c includes a fluid passageway 226 in communication with inlet 224a of fluid reservoir 224. Proximate its lower end 226a, fluid passageway 226 communicates with a cavity 227 formed within the third portion 222c of the housing. Disposed within cavity 227 is an elastomeric pierceable septum 228 that comprises a part of one form of the fill means of this latest form of the invention. Septum 228 can be bonded in place and is held in position by a retainer 228a and is pierceable by the needle of the syringe which contains the medicinal fluid to be dispensed and which can be used in a conventional manner to fill or partially fill reservoir 224 via passageway 226. Septum 228 can comprise a conventional or a slip filling septum. Additionally, septum 228 can be replaced with a needleless check valve with luer attachments.

Third portion 222c of housing 222 also includes a first chamber 230 for telescopically receiving a first medicament containing fill vial 232 and a second chamber 234 for telescopically receiving a second medicament containing vial 236. An elongated support 238 is mounted within first chamber 230 and a second elongated support 240 is mounted within second chamber 234. Each of the elongated supports 238 and 240 has an integrally threaded end portion 241 and carries a longitudinally extending, elongated hollow needle 242. Each of the hollow needles 242 has a flow passageway 242a that communicates with fluid passageway 226. First chamber 230, second chamber 234, elongated support 238, elongated support 240 and hollow needles 242 together comprise an alternate form of the fill means of the apparatus of the invention. The method of operation of this alternate form of fill means will presently be described.

Forming another very important aspect of the apparatus of the present invention is a novel flow control means that is connected to first portion 222a of outer housing 222. This flow control means functions to precisely control the rate of fluid flow outwardly from reservoir 224 and toward the patient. In the form of the invention shown in FIGS. 20 through 45 the flow control means comprises a flow control assembly generally designated in the drawings by the numeral 246. This novel flow control assembly here comprises an ullage defining member 248 having a first portion 248a disposed within inner, expandable housing 223 and a second portion 248b that extends outwardly from housing 222 in the manner shown in FIG. 21A. For a purpose presently to be described, member 248b has a fluid passageway 249 that is in communication with an outlet of the flow control subassembly 250, the character of which will next be described.

Referring to FIGS. 35 through 45, it can be seen that flow control subassembly 250, which comprises a part of flow control assembly 256, comprises an outer casing 252 having a plurality of circumferentially spaced-apart fluid outlets 254, a flow control member 256 telescopically receivable within casing 252 and a selector knob 258 that is interconnected with control member 256 in the manner shown in FIGS. 38 and 39. An elastomeric sealing band 253, which has the unique configuration shown in FIGS. 21F and 21E, prevents leakage between casing 252 and member 248. As best seen in FIGS. 36 and 39, flow control member 256 is uniquely provided with a plurality of elongated flow control channels 260, each having an inlet 260a and an outlet 260b. The flow channels 260 may be of different sizes, lengths and widths and in alternate configurations as shown by FIGS. 40 and 40A which depict alternate forms of the flow control member. The flow control member shown in FIG. 40 is identified as 258a, while the flow control member shown in FIG. 40A is identified as 258b. Flow control member 258b is provided with flow channels 250b that are formed in spaced-apart flow segments 251, each of which has a circuitous microfluidic flow path or micro channel of the configuration shown in FIG. 40A. Further, the flow control channels may be rectangular in cross-section as illustrated in FIG. 37, or alternatively, they can be semicircular in cross-section, U-shaped in cross-section, or they may have any other cross-sectional configuration that may be appropriate to achieve the desired fluid flow characteristics. When the flow control member is properly positioned within outer casing 252, the inner surface of the outer casing wall cooperates with channels 260 to form a plurality of generally spiral-shaped fluid flow passageways each being of different overall length and flow capacity. When the flow control member is positioned within the outer casing, a notch 256b formed in member 256 receives a tongue 252a provided on casing 252 so as to precisely align the outlets 260b of the flow channels 260 with fluid outlets 254 formed in casing 252. The various components of the flow control assembly are appropriately bonded, or otherwise sealably interconnected.

The flow control channels 260 can be made by several techniques including (micro) injection molding, injection-compression molding, hot-embossing and casting. The techniques used to make these imbedded fluid channels are now common-place in the field of microfluidics, which gave rise to the lab-on-a-chip, bio-MEMS and micro-total analysis systems (m-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.05 mm. subsequently, electroforming is performed to produce the negative metal form, or mold insert. Alternatively for larger channel systems, precision milling can be used to make the mold insert directly. Typical materials for the mold insert or embossing tool are Nickel, Nickel alloys, steel and brass. Once the mold insert of embossing tool is fabricated, the polymer of choice may be injection molded or embossed to yield the desired part with imprinted channels.

Alternatively, channels can also be made by one of a variety of casting processes. In general, a liquid plastic resin (e.g. a photopolymer) can be applied to the surface of a metal master (made by the techniques described above) and then cured via thermal of UV means. After hardening, the material is then "released" from the mold to yield the desired part. Additionally, there are similar techniques available that utilize CAD data (of the desired channel configuration) and direct laser curing of a liquid monomer to yield a polymerized and solidified part with imbedded channels. This process is available by contract, for example, for MicroTEC MbH of Duisburg, Germany.

A number of materials can be used to fabricate flow control member 256. While medical grade polymers are the most appropriate materials, other materials can be used including: Thermoplastics (embossing & injection molding); Duroplastics (injection molding); Elastomers (injection compression molding and soft lithography); Polyurethanes (castings); and Acrylics and Epoxies (RMPDO from microTEC). Additionally, the flow control members 256 can be constructed from various metals, metal alloys, silicon, silicon dioxide and inorganic oxides.

Selector knob 258, which comprises a part of the selector means of the invention, is rotatably connected to second portion 248b of ullage defining member 248 and, in a manner presently to be described, functions to rotate the assembly made up of outer casing 252 and flow control member 256. In this way, a selected outlet 254 in casing 252 can be selectively aligned with flow passageway 249 provided in the ullage defining member (see FIGS. 21A and 21B).

Turning once again to FIG. 20, also forming a part of the fluid dispensing apparatus of the present invention is dispensing means for dispensing fluid to the patient. In the present form of the invention this dispensing means comprises an administration set 264 that is connected to the first portion 222a of housing 222 in the manner shown in the drawings. The flow channel in the proximal end 265a of administration line 265 of the administration set 264 is in communication with fluid passageway 249 in the manner best seen in FIG. 21A. Disposed between the proximal end 265a and the distal end 265b of the administration line is a conventional gas vent and particulate filter 266. Provided at the distal end 265b is a luer connector 268 and cap 286a of conventional construction.

Turning now to FIGS. 23 and 24, the details of construction of the vial means or shell vial 270 is there shown. As indicated in these figures, each of the glass or plastic vial housings has a fluid chamber 272 for containing an injectable fluid. Chamber 272 is provided with a first open end 270a and second closed end 270b. First open end 270a is sealably closed by closure means here provided in the form of an externally threaded, elastomeric plunger 274 which is telescopically movable within the vial from a first location shown in FIG. 23, where the plunger is disposed proximate first open end 270a, to a second device-fill location where the plunger is disposed proximate second closed end 270b.

After removal of the closure 273, which forms a part of the third portion 222c of housing 222 (FIG. 22), vials 232 and 236 can be inserted into chambers 230 and 234 respectively. As the fill vials are so introduced and the plungers 274 are threadably interconnected with ends 241 of supports 238 and 240, the sharp ends of the elongated needles 242 will pierce the central walls 274a of the elastomeric plungers. Continuous pushing movement of the vials into chambers 230 and 234 will cause the structural supports 238 and 240 to move the elastomeric plungers inwardly of the vial chambers in a direction toward the second closed end 270b of the vials. As the plunger is moved inwardly of the vial, the fluid contained within the vial chamber will be expelled therefrom into the hollow elongated needles 242a. As best seen in FIG. 21A, the fluid will then flow past elastomeric, umbrella type check valves 278 and into passageways 280 formed in third portion 222c of the apparatus housing. Umbrella type check valves 278 function to control fluid flow from the elongated hollow needles 242 toward fluid passageways 280. From passageways 280 the fluid will flow into passageway 226 and then into internal fluid reservoir 224 of the bellows component 223 via ullage filling microchannels 224a. It is to be understood that the vials 232 and 236 can contain the same or different medicinal fluids and can be introduced into their respective chambers one at a time as shown in FIG. 22 or simultaneously as shown in FIG. 21.

Figure 21A:
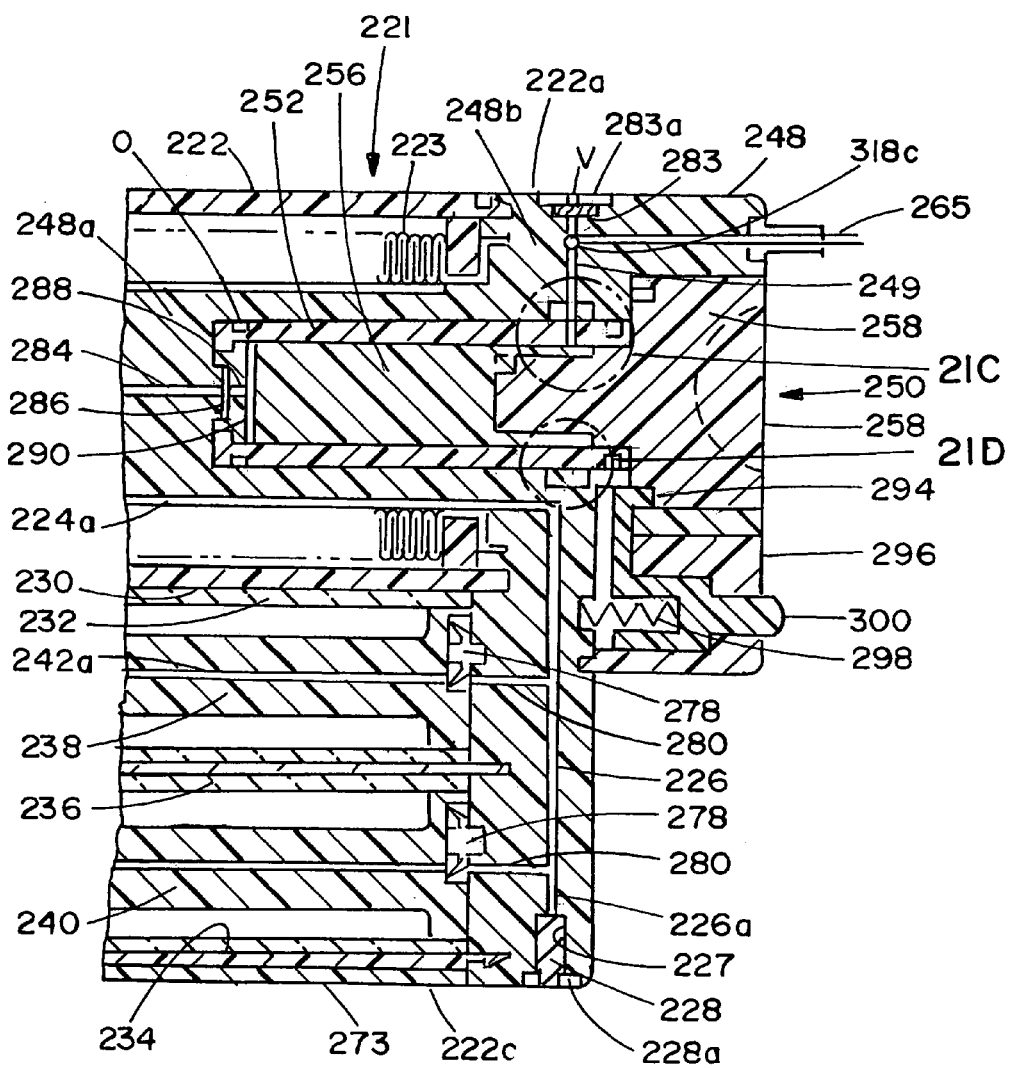
FIG. 21A is an enlarged, longitudinal cross-sectional view of the forward portion of the apparatus shown in FIG. 20.
Figure 21B:
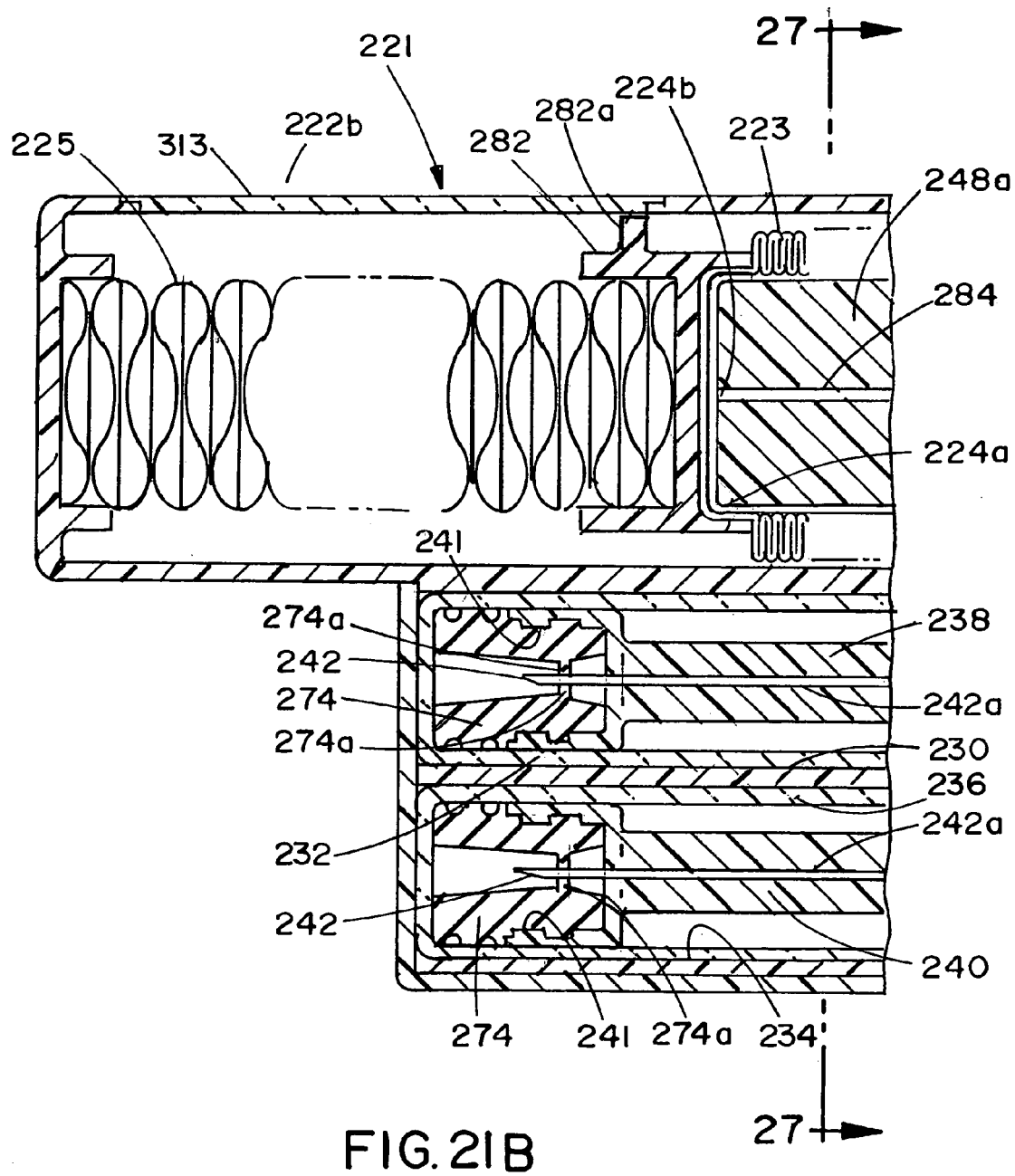
FIG. 21B is an enlarged cross-sectional view of the rear portion of the apparatus.
Figure 21F:
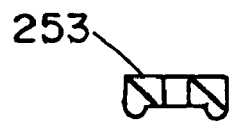
FIG. 21F is an enlarged, cross-sectional view of the elastomeric sealing band shown in FIG. 21C.
Figure 21C:
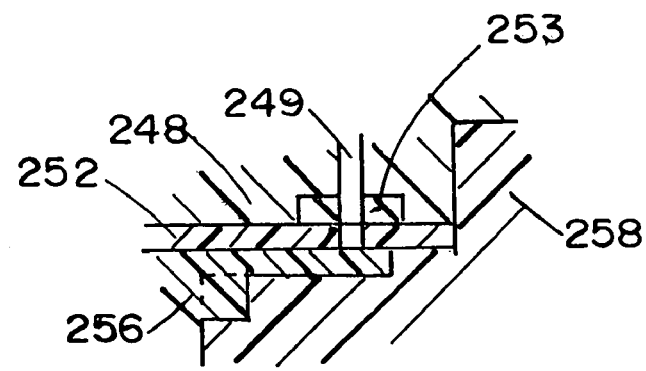
FIG. 21C is an enlarged, cross-sectional view of the area designated as 21C in FIG. 21A.
Figure 21E:
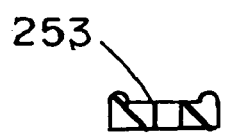
FIG. 21E is an enlarged, cross-sectional view of the elastomeric sealing band shown in 21E in FIG. 21D.
Figure 21D:
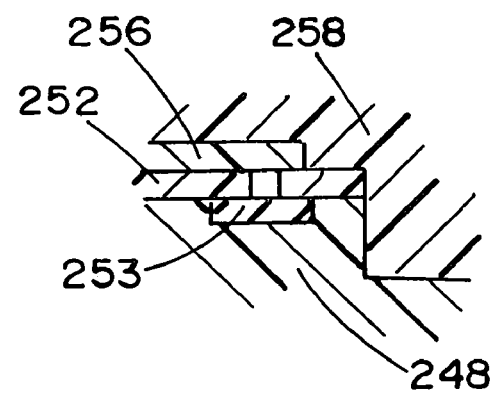
FIG. 21D is an enlarged, cross-sectional view of the area designated as 21D in FIG. 21A.
Figure 22:
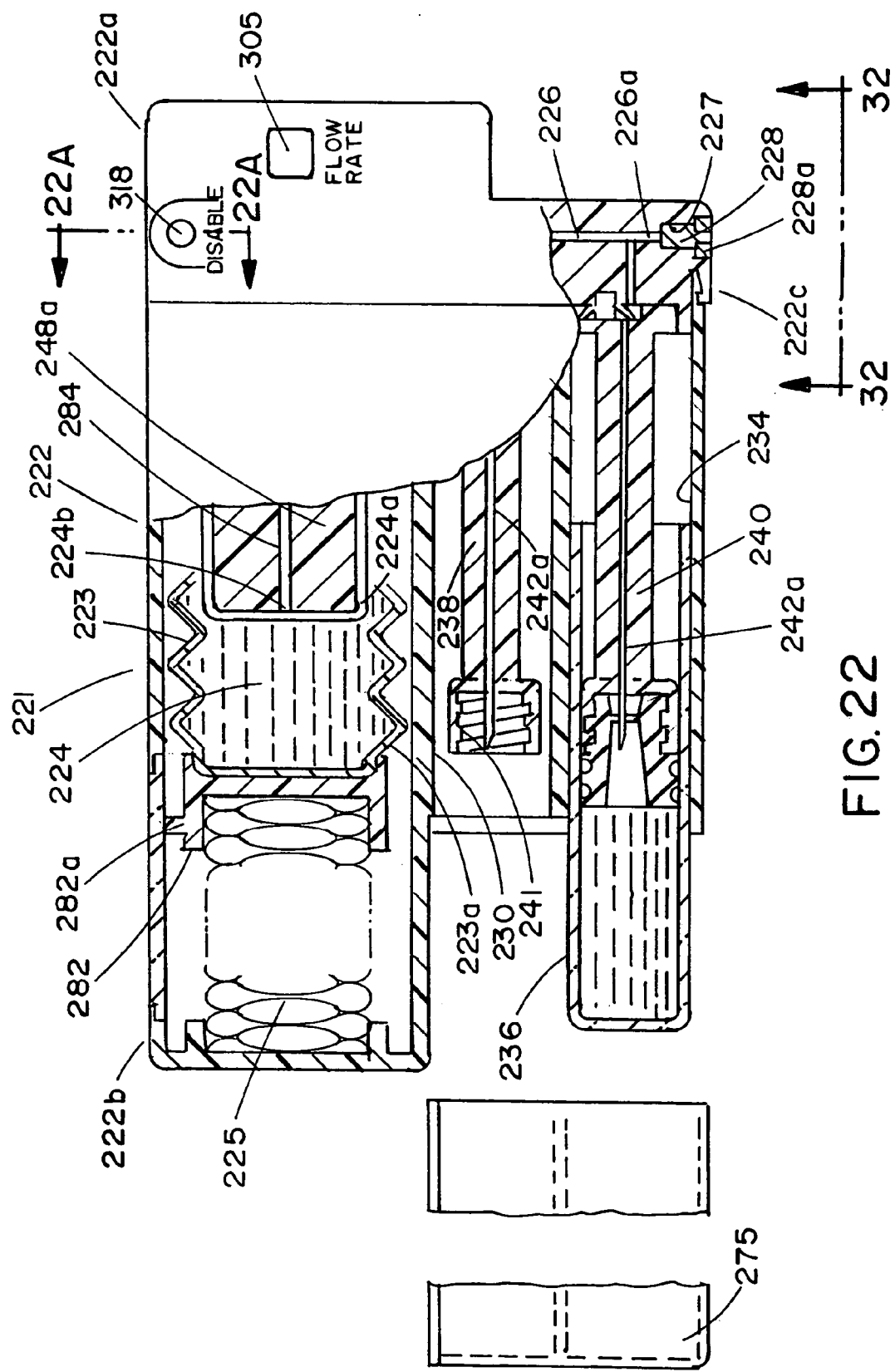
FIG. 22 is a cross-sectional view similar to FIG. 21, but showing the apparatus in a fluid fill mode.
Figure 27:
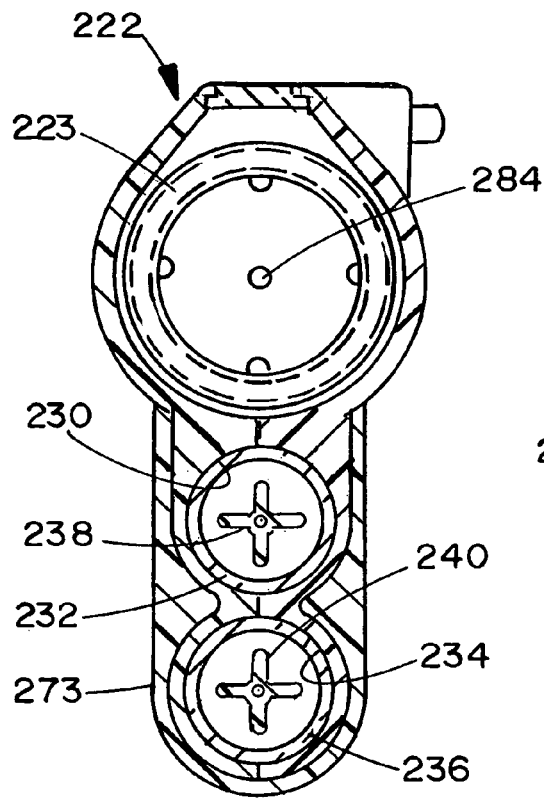
FIG. 27 is a cross-sectional view taken along lines 27—27 of FIG. 21B.
Figure 25:
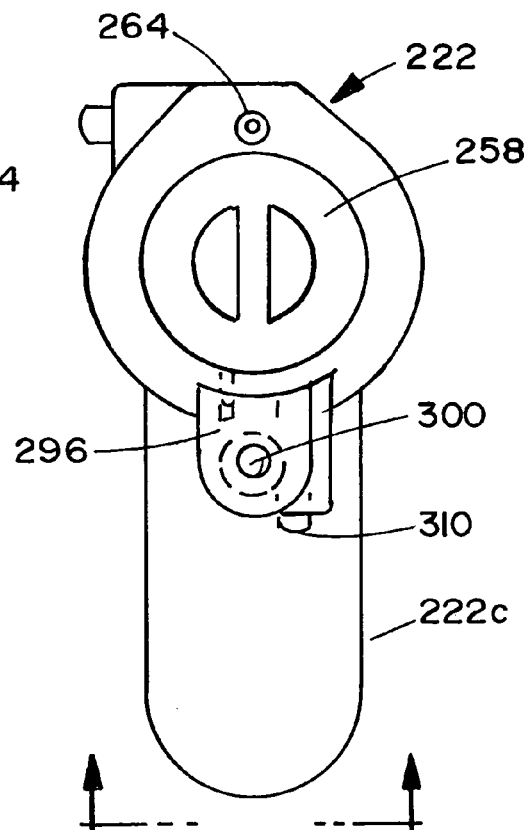
FIG. 25 is an end view of the apparatus shown in FIG. 21.
Figure 26:
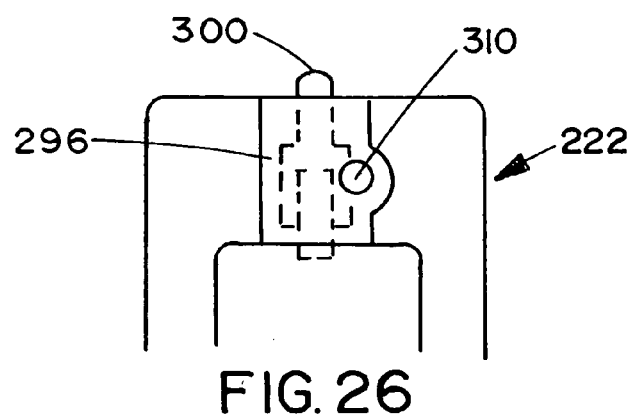
FIG. 26 is a view taken along lines 26—26 of FIG. 25.

As the fluid flows into the bellows reservoir, the bellows will be expanded from the collapsed configuration shown in FIG. 21B into an expanded configuration, such as shown in FIG. 22. As the bellows member expands it will urge a telescopically movable volume indicator or coupling member 282 that is carried within the second portion of the housing in engagement with the stored energy source, or spring member 225 causing it to further compress.

It is also to be understood that, if desired, the reservoir of the bellows component can also be filled by alternate filling means of the character previously described which comprises a syringe having a needle adapted to pierce the pierceable septum 228 which is mounted within third portion 222c of the apparatus housing. As the reservoir 224 fills with fluid either from the fill vials or from the filling syringe, any gases trapped within the reservoir will be vented to atmosphere via vent means "V" mounted in portion 248b of the ullage member. This vent means here comprises a gas vent 283 that can be constructed of a suitable hydrophobic porous material such as a porous plastic. Gas vent 283 is held in position within the housing by a bonded retainer ring 283a (FIG. 21A).

Upon opening the fluid delivery path to the administration set 264 in a manner presently be described, the stored energy means, or member 225, will tend to return to its initial starting, less compressed configuration thereby controllably urging fluid flow outwardly of reservoir 224 via the flow control means of the invention.

As previously discussed a number of beneficial agents can be contained within vials 232 and 236 and can be controllably dispensed to the patient including, by way of example, liquid injectable medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Considering next the operation of the flow rate control means of the invention, as the fluid contained within the bellows reservoir 224 is urged outwardly thereof by the stored energy means, the fluid will flow into a fluid passageway 284 formed in the first portion 248a of ullage member 248. The fluid will then flow under pressure through a filter means shown here as a filter 286 that is peripherally bonded within a cavity provided in the flow control member 256 of the flow control subassembly 250. Filter 286, which functions to filter particulate matter from the fluid flowing outwardly from reservoir 224 is of a character well known to those skilled in the art and can be constructed from various readily available materials such as polysolfone and polypropylene wafers having a desired porosity. After flowing through filter 286, the fluid will flow, via a stub passageway 288 (FIG. 21A) into the distribution means of the invention for distributing fluid from the fluid reservoir to each of the plurality of spiral passageways 260. This distribution means here comprises several radially outwardly extending flow passageways 290 formed in flow control member 256. The filtered fluid will fill passageways 290 and then will flow into the plurality of spiral passageways 260 formed in member 256 via outlets 260b, which communicate with passageways 260 (see FIG. 39). The fluid contained within spiral passageways 260 can flow outwardly of the device via outlets 260b only when one of the fluid outlets 254 formed in casing 252 is aligned with reservoir outlet passageway 249 (FIG. 21A).

Selection of the passageway 260 from which the fluid is to be dispensed is accomplished by rotation of the selector knob 258 which, as best seen in FIG. 39, includes a reduced diameter portion 258a having a slot 258b formed therein. As illustrated in FIG. 36, slot 258b is adapted to receive a spline 256a (FIG. 36) formed anteriorly of member 256. With this construction, rotation of selector member 258 by gripping a transversally extending finger gripping member 258g will impart rotation to member 256. As seen in FIG. 39, casing 252 is also provided with an inwardly extending spline segment 252a that is received within a slot 256b formed in the rearward periphery of member 256 (FIG. 38). Accordingly, rotation of member 256 will also impart concomitant rotation to casing member 252.

Figure 20:
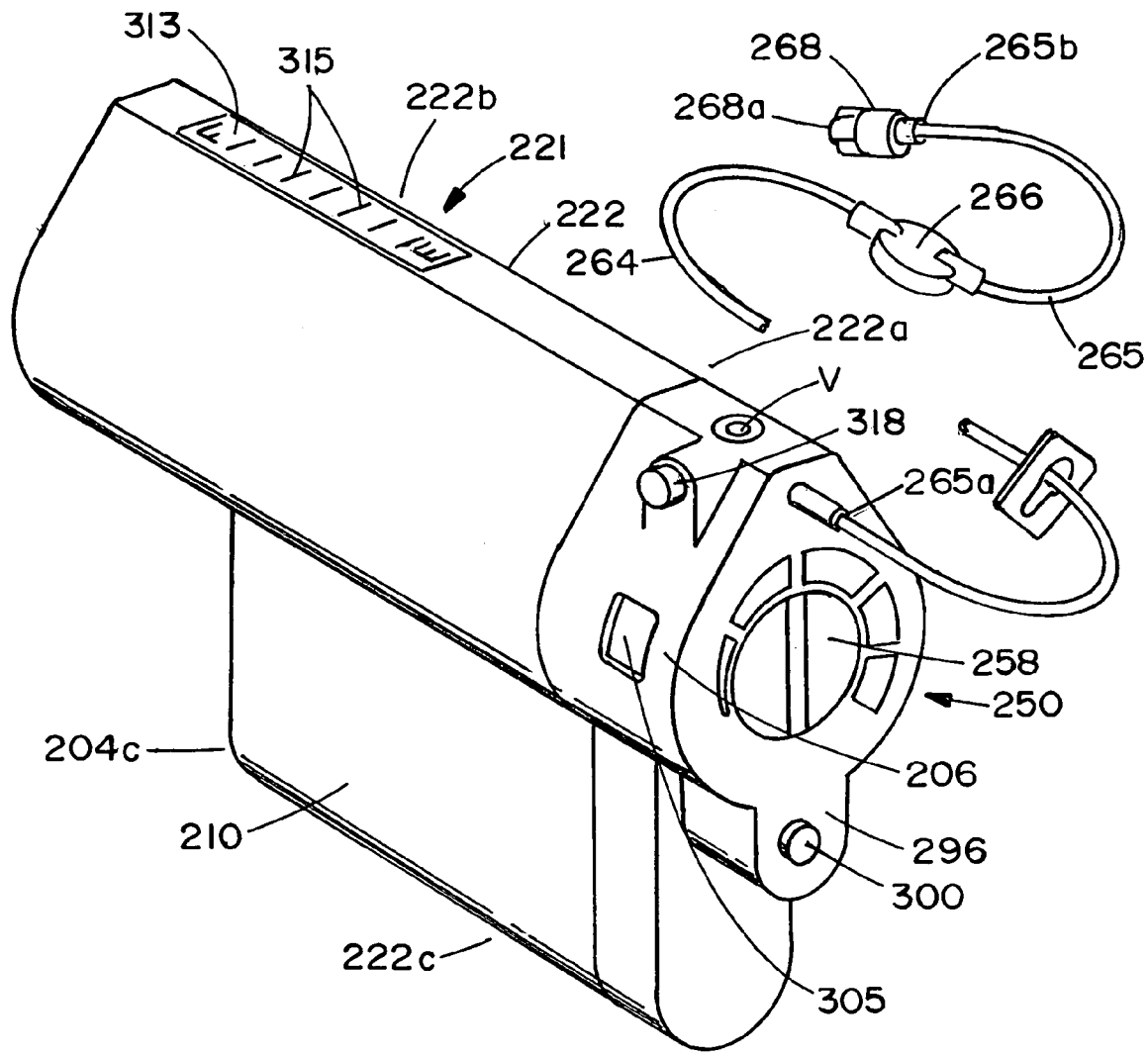
FIG. 20 is a generally perspective view of an alternate embodiment of the infusion apparatus of the present invention for dispensing fluids at a uniform rate.

As illustrated in FIGS. 35 and 39, selector knob 258 is provided with a plurality of circumferentially spaced apart indexing cavities 258c that closely receive an indexing finger 294 which forms a part of the indexing means of the invention, which means comprises a locking shaft cover 296 that is connected to third portion 222c of the apparatus housing (see FIGS. 20 and 21A). Indexing finger 294 is continuously urged into engagement with a selected one of the indexing cavities 258c by a coil spring 298 that also forms a part of the indexing means of the invention. Coil spring 298 can be compressed by an inward force exerted on an indexing shaft 300 that is mounted in locking shaft cover 296 and is movable from the extended position shown in FIG. 21A to an inward, finger release position wherein spring 298 is compressed and finger 294 is retracted from a selected indexing cavity 258c (see also FIGS. 30, 31 and 32). With finger 294 in its retracted position it is apparent that control knob 258 can be freely rotated to a position wherein flow rate indicia 304 formed on the periphery of knob 258 (FIG. 35) can be viewed through a viewing window 305 formed in the first portion 206 of the apparatus housing. Locking means, here provided in the form of a locking member 310 (see FIG. 29), is also carried by the locking shaft cover and, when moved from the release position shown in FIG. 33 into the locking position shown in FIG. 34, prevents inward movement of the indexing shaft 300 against the urging of spring 298. A spring biased retainer pin 311 (FIG. 31) functions to retain the selector knob in position within housing 222a.

When the selector knob is in the desired position and pressure is released on indexing shaft 300, spring 298 will urge finger 294 of the indexing means of the invention into locking engagement with one of the indexing cavities 258c thereby placing a selected one of the spiral shaped flow control channels 260 in communication with the fluid reservoir 224 via passageways 290, 288 and 284. As the fluid flows outwardly of the apparatus due to the urging of the stored energy means or spring member 225, the bellows structure 223 will be collapsed and at the same time member 282 will travel inwardly of housing portion 222b. Coupling member 282, which forms a part of the volume indicator means of the invention, includes a radially outwardly extending indicating finger 282a that is visible through a volume indicator window 313 that is provided in a second portion 222b of the apparatus housing and also comprises a part of the volume indicator means of the invention (FIG. 20). Indicia 315, which are provided on indicator window 313, function to readily indicate to the caregiver the amount of fluid remaining within fluid reservoir 224.

Figure 28:
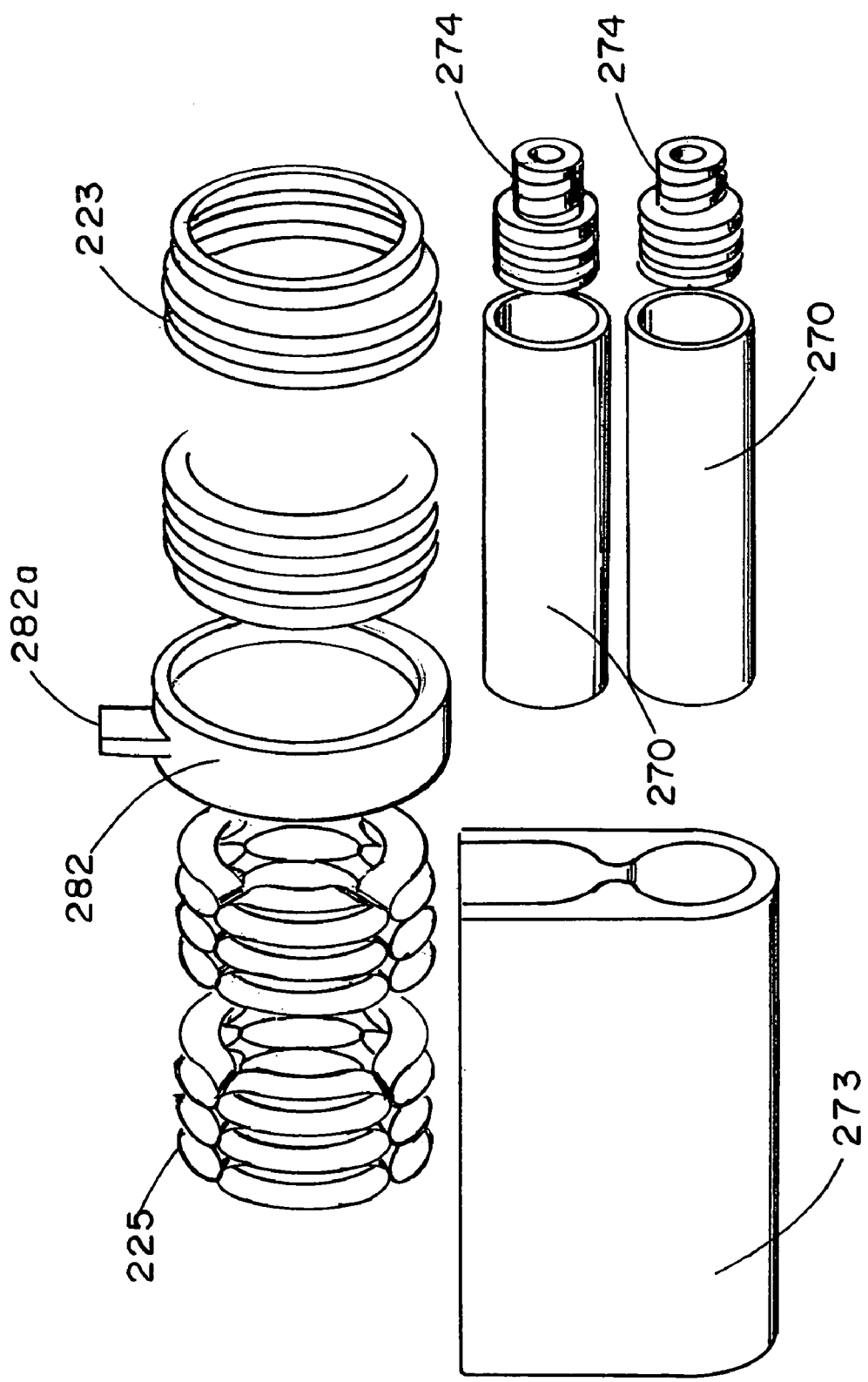
FIGS. 28 and 28A, when considered together comprise a generally perspective, exploded view of the various internal operating components of this latest form of the apparatus of the invention.
Figure 28A:
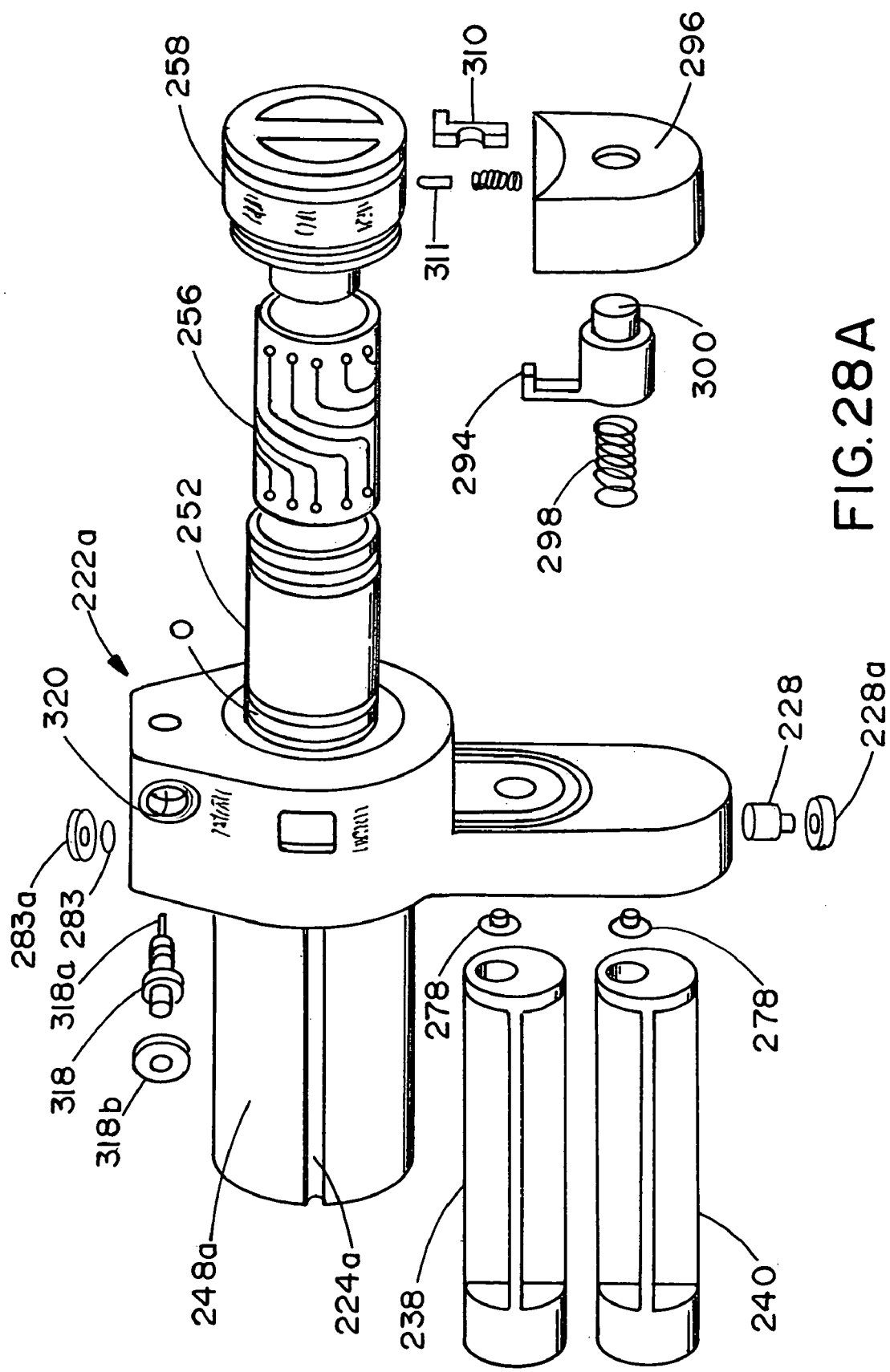
Figure 29:
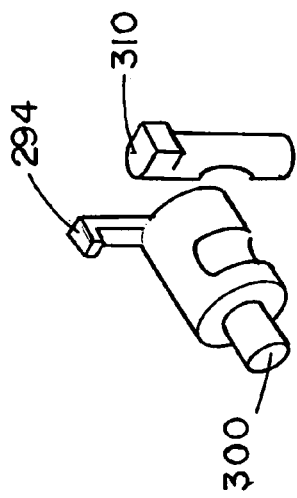
FIG. 29 is a generally perspective, exploded view of one form of the indexing means of the invention shown in FIG. 21A.
Figure 31:
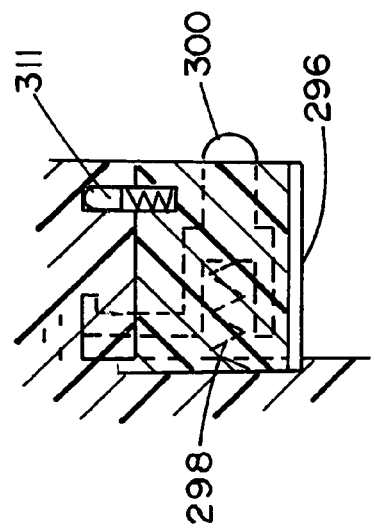
FIG. 31 is a cross-sectional view taken along lines 31—31 of FIG. 30.
Figure 30:
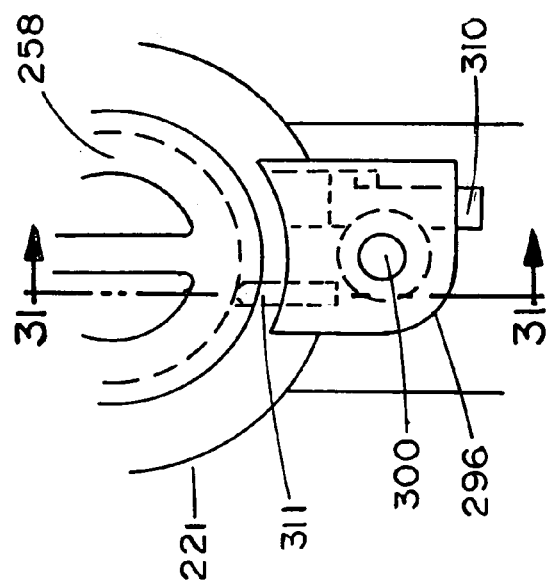
FIG. 30 is a fragmentary, front view similar to the front view shown in FIG. 25, but better showing the configuration of the indexing means of the invention.
Figure 32:
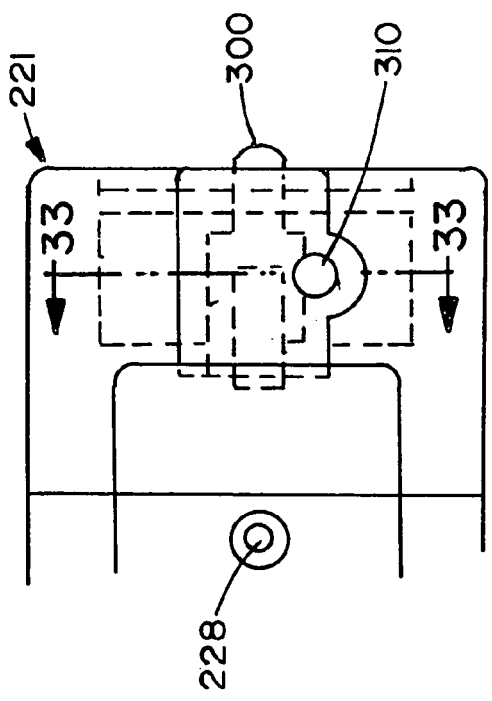
FIG. 32 is an enlarged, fragmentary, bottom view of the forward portion of the apparatus shown in FIG. 22.
Figure 34:
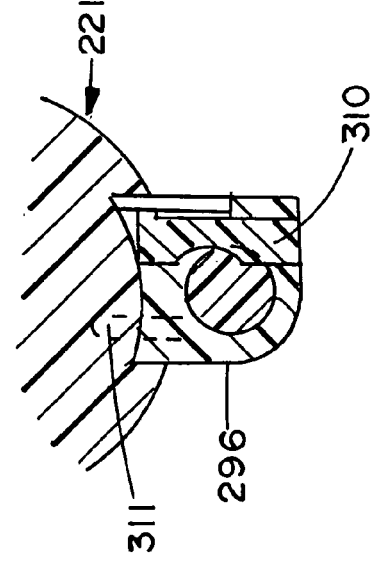
FIG. 34 is a fragmentary, cross-sectional view similar to FIG. 33 but showing the indexing means in a locked position.
Figure 33:
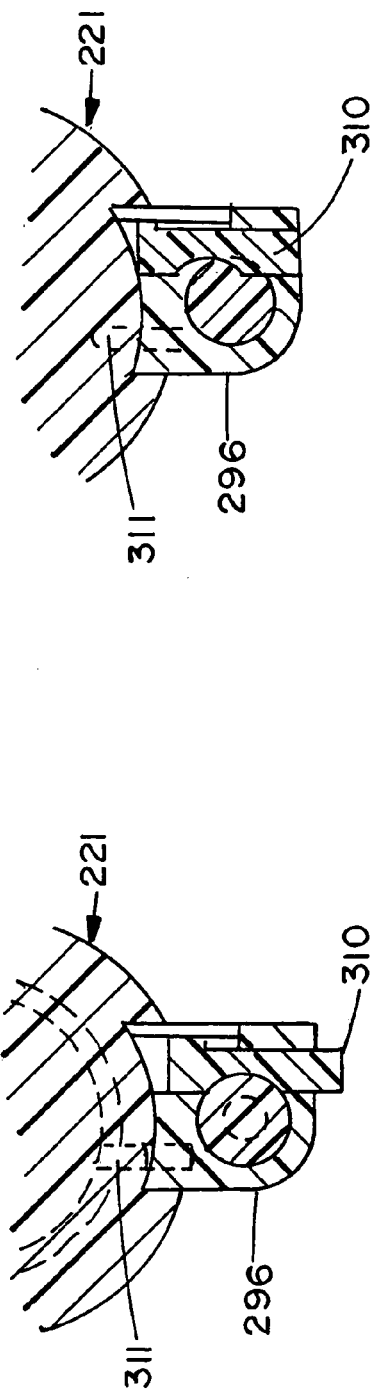
FIG. 33 is a cross-sectional view taken along lines 33—33 of FIG. 32 but rotated 90° counterclockwise.
Figure 46:
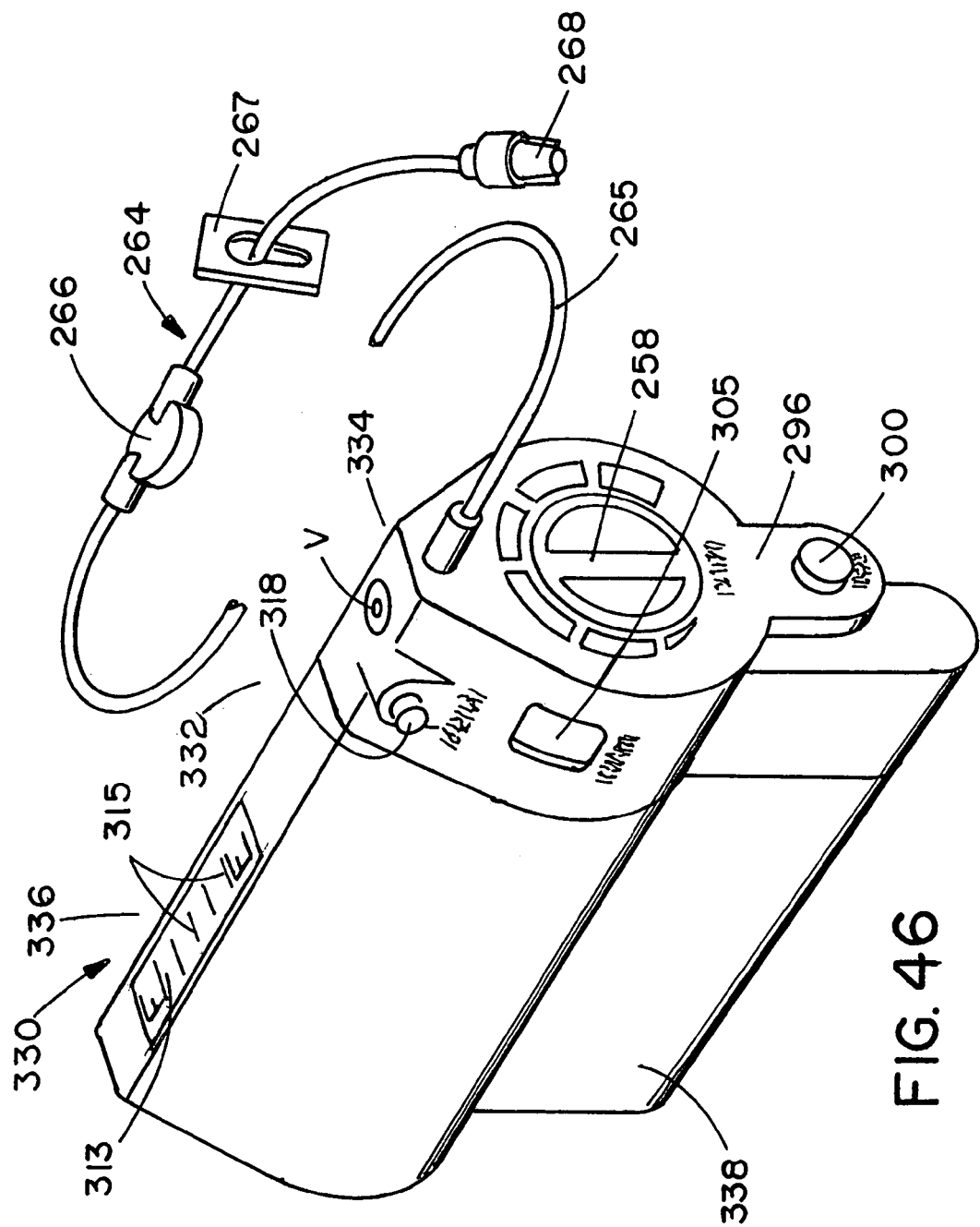
FIG. 46 is a generally perspective view of an alternate embodiment of the fluid delivery apparatus of the present invention for dispensing fluids at a uniform rate.

Safety disabling means, shown here as a disabling shaft 318 that is telescopically movable within a passageway 320 formed within housing portion 222a functions to disable the device (FIG. 22A, 28A), by occluding the output passageway 249. More particularly, shaft 318 has a distal end 318a, which, upon insertion of the shaft, will block fluid flow through passageway 249. A retainer 318b normally holds shaft 318 in the retracted position (see FIG. 22A).

Figure 47:
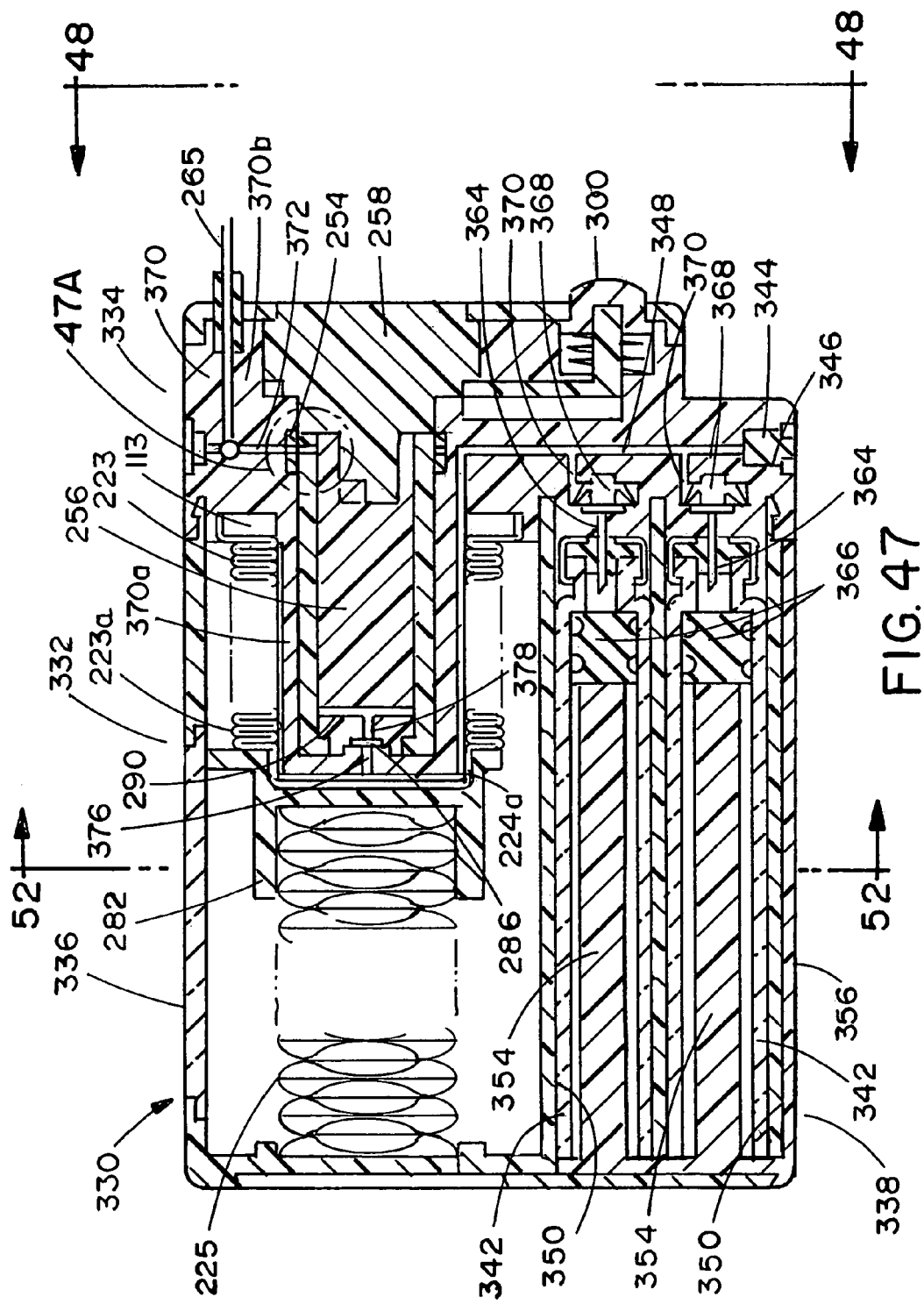
FIG. 47 is an enlarged, longitudinal cross-sectional view of the embodiment of the invention shown in FIG. 46.
Figure 47A:
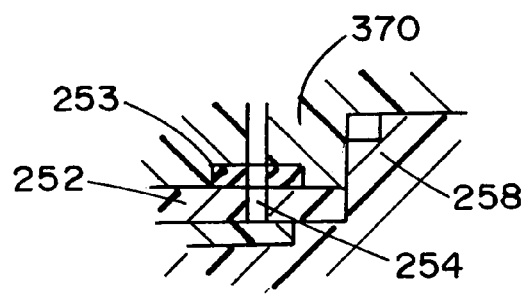
FIG. 47A is an enlarged, cross-sectional view of the area designated as 47A in FIG. 47.
Figure 48:
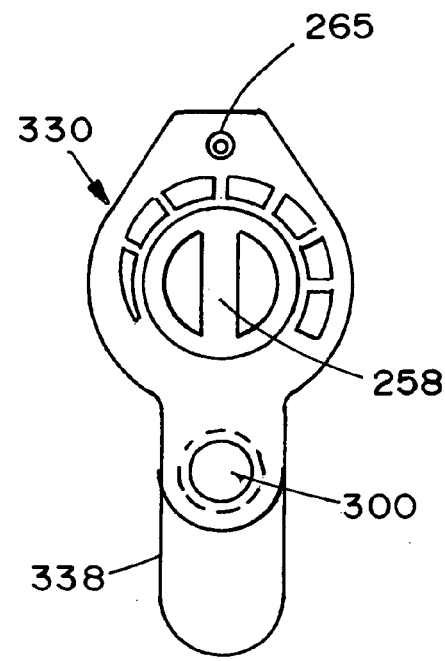
FIG. 48 is view taken along lines 48—48 of FIG. 47.
Figure 47B:
FIG. 47B is an enlarged, cross-sectional view of the elastomeric sealing band shown in FIG. 47A.
Figure 49:
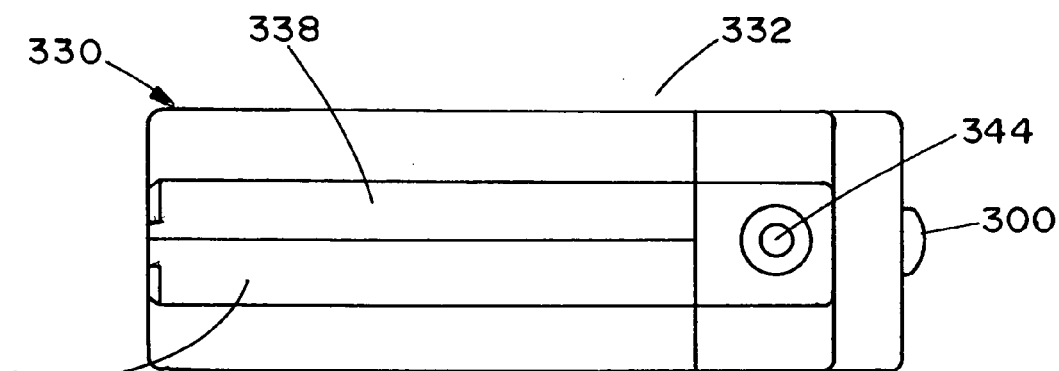
FIG. 49 is a bottom view of the apparatus shown in FIG. 47.
Figure 52:
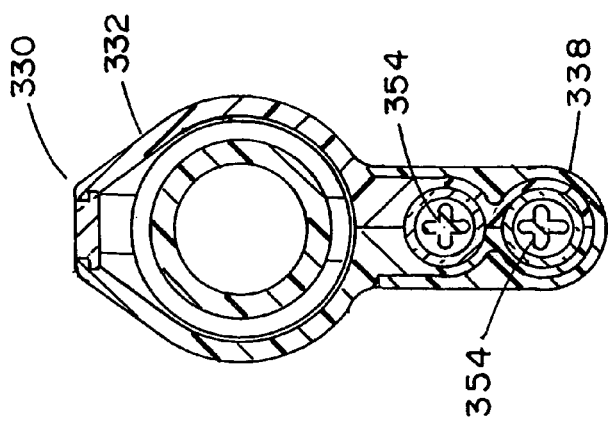
FIG. 52 is a cross-sectional view taken along lines 52—52 of FIG. 47.
Figure 53:
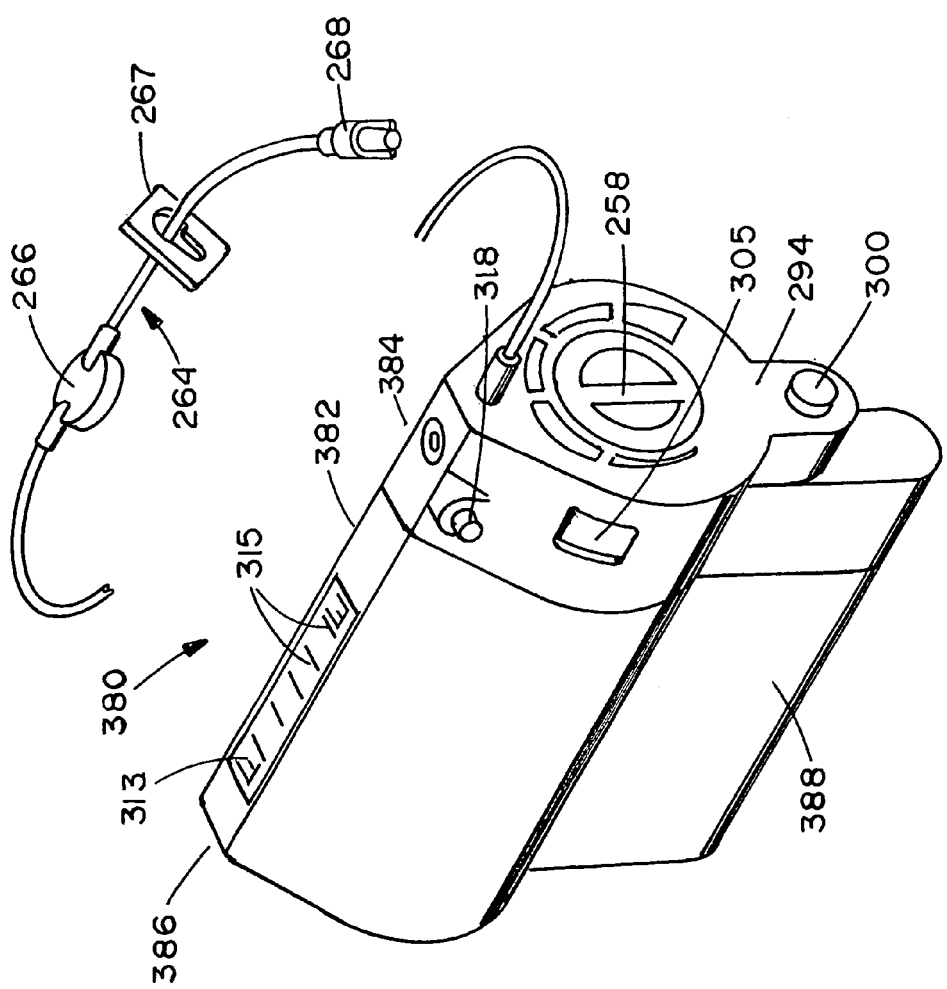
FIG. 53 is a generally perspective view of yet another embodiment of the present invention for dispensing fluids at a uniform rate.
Figure 55:
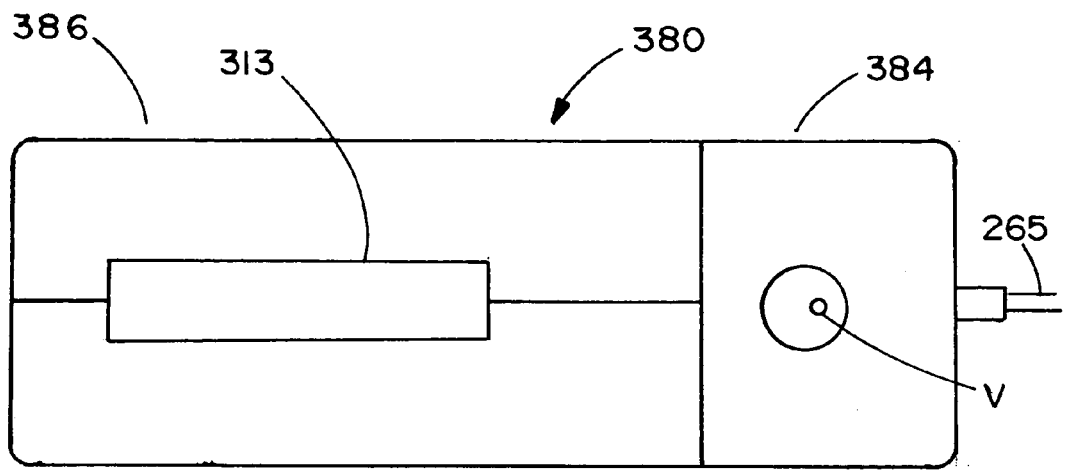
FIG. 55 is a top view of the apparatus shown in FIG. 54.
Figure 56:
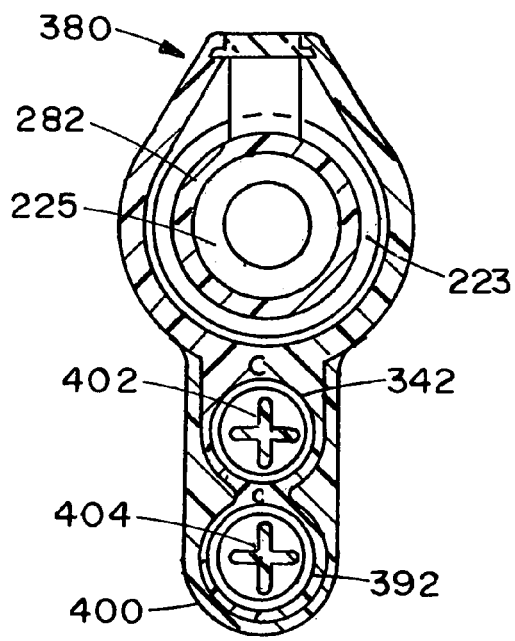
FIG. 56 is cross-sectional view taken along lines 56—56 of FIG. 54.
Figure 57:
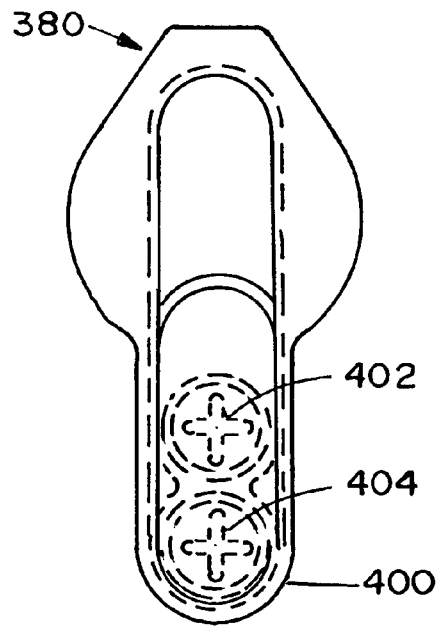
FIG. 57 is a left end view of the apparatus shown in FIG. 54.
Figure 60:
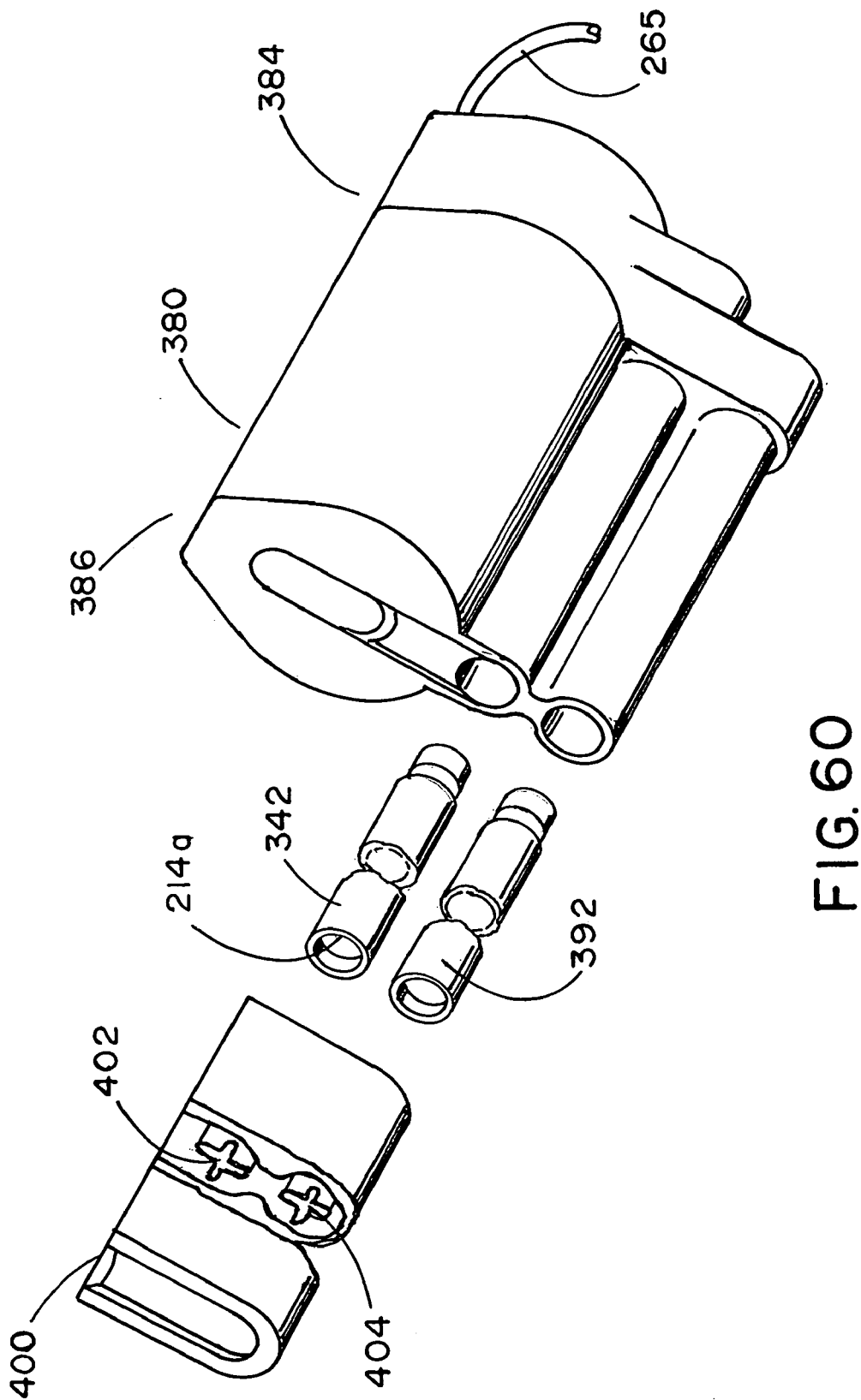
FIG. 60 is a generally perspective exploded view of this latest embodiment of the invention.

Referring now to FIGS. 46 through 52, yet another embodiment of the dispensing apparatus of the present invention is there illustrated and generally designated by the numeral 330. This alternate form of the apparatus of the invention is similar in many respects to that shown in FIGS. 20 through 45 and like numerals are used in FIGS. 46 through 52 to identify like components. The primary difference between this latest form of the invention and the invention shown in FIGS. 20 through 45 resides in the fact that two cartridge fill vials of a different construction are used to fill the fluid reservoir of the apparatus. As before, the apparatus of this alternate form of the invention comprises an outer housing 332 having first, second and third portions 334, 336, and 338 respectively. Disposed within outer housing 332 is an inner, expandable housing 223 that is of identical construction and operation to the expandable housing of the embodiment of the invention shown in FIGS. 21A and 21B. As in the earlier described embodiment, housing 223 includes a fluid reservoir that is provided with an inlet 224a (FIG. 47) for permitting fluid flow into the fluid reservoir. As shown in FIG. 47, expandable housing 223 comprises a bellows structure having an expandable and compressible, accordion-like side wall 223a, which is suitably bonded at its open end 223b to member 370b.

Disposed within second portion 336 of outer housing 332 is the stored energy means of the invention for acting upon inner expandable housing 223 in a manner to cause the fluid contained within the fluid reservoir to controllably flow through outlet 376. In this alternate form of the invention, the important stored energy means is identical in construction and operation to the earlier described stored energy means and here comprises a compressively deformable, wave spring member 225 that is carried within the second portion 336 of the outer housing. As before, in operation member 225 is first more frilly compressed by fluid flowing into the reservoir and then is controllably unloaded or expanded to cause fluid flow from the reservoir.

As in the last described embodiment of the invention, the apparatus of this alternate form of the invention comprises fill means carried by the third portion 338 of outer housing 332 for filling the reservoir with the fluid to be dispensed. This fill means is also similar to the earlier described fill means, save for the fact that the fill means of this latest embodiment comprises a pair of glass or plastic fill vials or cartridges 342 which each are of identical construction. As in the earlier described embodiments, the fill means also includes an alternate fill means that comprises a pierceable septum 344 that is disposed within a cavity 346 formed in the third portion 338 of outer housing 332. Elastomeric septum 344 is pierceable by the needle of the syringe which contains the medicinal fluid to be dispensed and which can be used to fill or partially fill the fluid reservoir via a passageway 348 formed in third portion 338.

As best seen in FIG. 47, third portion 338 of housing 332 includes a pair of spaced-apart chambers 350 for telescopically receiving the medicament containing fill vials 342. As shown in FIGS. 47 and 51 a pair of elongated supports 354 are mounted within a hollow vial cover 356 that forms a part of the third portion 338 of the housing and removably covers the fill vials in the manner shown in FIG. 47. Each of the fill vial cartridges 342, is of the generally conventional pharmaceutical industry construction shown in FIGS. 50 and 50A, and each comprises a hollow glass or plastic body portion 358 that defines a fluid chamber 360. Each fill vial has an open first end 342a and a second end that is closed by a pierceable, elastomeric septum 362 that is held in place by a mechanical clamping ring. Mounted proximate the inboard end of each chamber 350 is a hollow needle 364 which is adapted to pierce septum 362 when the fill vials are inserted into chambers 350 in a manner next to be described.

Disposed within each vial reservoir 360 is a plunger 366 that is moved by a support 354 of vial cover 356 from a first position proximate end 342a of the vial to a second position. More particularly, as the vial cover 356 is mated with the apparatus housing, the inboard end of each of the elongated supports 354 engages a plunger 366 urging the plunger inwardly of the vial chamber 360. As each of the plungers move inwardly of their respective vial reservoirs, the fluid contained in the reservoir will be forced through hollow needle 364, passed an umbrella check valve 368 mounted within third housing portion 338, into a stub passageway 370, into a passageway and finally into fluid reservoir via inlet 224a. As the fluid flows into the reservoir, it will more fully compress the stored energy means in the manner previously described.

The apparatus of this latest form of the invention also includes flow control means that is quite similar in construction and operation to the flow control means described in connection with the embodiment of the invention shown in FIGS. 20 through 45. This flow control means is connected to first portion 334 of outer housing 332 and comprises an ullage defining member 370 having a first portion 370a disposed within inner, expandable housing 223 and a second portion 370b having a fluid passageway 372 that is in communication with outlet 376 of the fluid reservoir.

As before, the flow control means includes a flow control subassembly that is substantially identical in construction and operation to the earlier described flow control subassembly 250 and is of the configuration shown in FIGS. 35 through 45 of the drawings. For this reason, the details of the construction and operation of the flow control means of this latest embodiment of the invention will not be here repeated and reference should be made to the earlier description of the flow control subassembly 250.

Turning once again to FIG. 46 also forming a part of the fluid dispensing apparatus of this latest form of the invention is dispensing means for dispensing fluid to the patient. This dispensing means is identical in construction and operation to the previously identified administration set 264 and is connected to the first portion 334 of housing 332.

Upon opening the fluid delivery path to the administration set 264, the stored energy means, or member 225, will tend to return to its less compressed starting configuration thereby controllably urging fluid flow outwardly of the device reservoir via the flow control means of the invention. As the fluid contained within the bellows reservoir is urged outwardly thereof by the stored energy means, the fluid will flow into a fluid passageway 376 formed in the first portion 370a of ullage member 370. The fluid will then flow under pressure through a filter means shown here as a filter 286 that is identical to that previously described. After flow through filter 286, the fluid will flow, via a stub passageway 378 (FIG. 47) into the several radially outwardly extending flow passageways 290 formed in flow control member 256. The filtered fluid will fill passageways 290 and then will flow into the plurality of spiral passageways 260 formed in member 256 via outlets 254, which communicate with passageways 260 (see FIG. 36). The fluid contained within spiral passageways 260 can flow outwardly to the patient via the administration line only when one of the fluid outlets 254 formed in casing 252 is aligned with passageway 372 (FIG. 47).

Selection of the passageway 260 from which the fluid is to be dispensed is accomplished by rotation of the selector knob 258 in the manner previously described in connection with the embodiment shown in FIGS. 20 through 45. The construction and operation of the selector knob, the indexing means and the locking means is identical to that previously described and will not be redescribed at this time.

As in the earlier described embodiment of the invention, as the fluid flows outwardly of the apparatus due to the urging of the stored energy means or spring member 225, the bellows structure 223 will be collapsed and at the same time coupler member 282 will travel inwardly of housing portion 336 and will provide an indication of the volume of fluid remaining in the fluid reservoir in the same manner as earlier described.

This latest embodiment also includes safety disabling means 318, which is substantially identical in construction and operation to that previously described.

Turning now to FIGS. 53 through 66, still another form of the dispensing apparatus of the present invention is there illustrated and generally designated by the numeral 380. This alternate form of the apparatus of the invention is similar in some respects to that shown in FIGS. 46 through 52 and like numerals are used in. FIGS. 53 through 66 to identify like components. The primary difference between this latest form of the invention and the invention shown in FIGS. 46 through 52 resides in the fact that one of the two fill vials used to fill the fluid reservoir of the apparatus is of totally different construction. More particularly, one of the fill vials is specially designed to enable the reconstitution and intermixing of a contained lypholized drug with a suitable reconstitution agent prior to the delivery of the mixture to the fluid reservoir of the device. The second cartridge will typically carry a diluent to add to the first now injectable drug in residence in the reservoir.

As in the earlier described embodiments, the apparatus of this latest form of the invention comprises an outer housing 382 having first, second and third portions 384, 386 and 388 respectively. Disposed within outer housing 382 is an inner, expandable housing 223 that is of identical construction and operation to the expandable housing of the embodiment of the invention shown in FIGS. 46 through 52. As in the earlier described embodiment, housing 382 includes a fluid reservoir that is provided with an inlet 216 (FIG. 54) for permitting fluid flow into the fluid reservoir. As shown in FIG. 54, expandable housing 223 comprises a bellows structure having an expandable and compressible, accordion like sidewall 223a.

Disposed within second portion 386 of outer housing 382 is the stored energy means of the invention for acting upon inner expandable housing 223a in a manner to cause the fluid contained within the fluid reservoir of the device to controllably flow through outlet 374. In this latest form of the invention, the important stored energy means is identical in construction and operation to the earlier described stored energy means and here comprises a compressively deformable, spring member 225 that is carried within the second portion 386 of the outer housing. As before, in operation member 225 is first more fully compressed by fluid flowing into the device reservoir and then is controllably unloaded or expanded to cause fluid flow from the reservoir.

As previously mentioned, the apparatus of this latest form of the invention comprises fill means of a somewhat different construction, that is, carried by the third portion 388 of outer housing 382 for filling the device reservoir with the fluid to be dispensed. This fill means, like the last described fill means, comprises a pair of fill vials or cartridges, one of which, namely fill vial 342, is of identical construction and operation to the earlier described fill vial 342. The second fill vial or cartridge designated by the numeral 392 comprises a container of special design that uniquely contains a lyophilized drug 394 that is separated from a reconstituting fluid 396 by a barrier stopper 398 (FIG. 61). Lyophilized drug 394 can, by way of example, comprise an anti-infective, an oncolytics agent, a cardiac drug or various other types of beneficial agents. Cartridge 392 is telescopically receivable within a vial housing 400 that is of the configuration shown in FIGS. 54, 58 and 60. As before, vial housing 400 includes a pair of spaced apart pusher members 402 and 404 which engage plungers 366 (FIG. 63) and 406 (FIG. 61) respectively to push the plungers forwardly of their respective container reservoirs.

Considering in more detail the novel cartridge assembly 392, as best seen in FIG. 61, this cartridge assembly includes a vial 408 that is sealed at one end by a plunger 406 and at the other end by a pierceable septum 410 (FIG. 61) that is held in place by a suitable crimp ring. Formed intermediate the ends of vial 408 is a raised outer wall portion 408a which permits fluid 396 to bypass elastomeric barrier stopper 398 as the barrier stopper is urged inwardly of the container by pressure exerted thereon by the fluid 396. Fluid 396 exerts pressure on barrier member 398 as a result of pusher member 404 exerting inward pressure on plunger 406, which pressure is, in turn, caused by the inward movement of plunger 406 as the vial housing is mated with and advanced within the apparatus housing 382.

A continued inward pressure exerted on plunger 406 will cause fluid 396 to flow past barrier member 398 via wall portion 408a so as to reconstitute lyophilized drug 394 with an internally contained reconstitution agent 396. Further pressure exerted on plunger 406 will cause the reconstituted drug formed by the fluid 396 which has been intermixed with drug 394 to flow through a hollow cannula 412, past check valve 414, into a stub passageway 416 and then into a passageway 418 and finally into the device reservoir via ullage microchannels 420.

As previously mentioned, plunger 406 is disposed within vial 392 and is moved by a support 404 of vial closure 400 as the vial cover is mated with the apparatus housing. As plunger 366 is moved inwardly of vial reservoir 360, the fluid contained in the reservoir will be forced through hollow needle 412a, passed an umbrella check valve 414a mounted within third housing portion 388, into a stub passageway 416, into a passageway 418 and finally into the device reservoir via ullage reservoir filling channel 420. As the fluid flows into the device reservoir, it will more fully compress the stored energy means in the manner previously described.

As in the earlier described embodiments, the fill means also includes an alternate fill means that comprises a mechanical check valve (not shown) or an elastomeric pierceable septum 344 that is disposed within a cavity 346 formed in the third portion 388 of outer housing 382. Septum 344 is pierceable by the needle of the syringe which contains the medicinal fluid to be dispensed and which can be used to fill or partially fill the device reservoir via passageway 418 formed in third portion 388.

The apparatus of this latest form of the invention also includes flow control means that is identical in construction and operation to the flow control means described in connection with the embodiment of the invention shown in FIGS. 36 through 45. This flow control means is connected to first portion 384 of outer housing 382 and comprises an ullage defining member 370 having a first portion 370a disposed within inner, expandable housing 223 with which the bellows slidably cooperates and a second portion 370b having a fluid passageway 372 that is in communication with outlet 374 of the device reservoir. Once again, the ullage defining member functions to ensure that substantially all of the medicament is dispensed from the fluid reservoir.

As before, the flow control means includes a flow control subassembly that is substantially identical in construction and operation to the earlier described flow control subassembly 250 and is of the configuration shown in FIGS. 36 and 38 of the drawings. For this reason, the details of the construction and operation of the control means of this latest embodiment of the invention will not be here repeated and reference should be made to the earlier description of the flow control subassembly 250.

Turning once again to FIG. 53, also forming a part of the fluid dispensing apparatus of this latest form of the invention is dispensing means for dispensing fluid to the patient. This dispensing means is identical in construction and operation to the previously identified administration set 264 and is connected to the first portion 384 of housing 382.

Upon opening the fluid delivery path to the administration set 264 in the manner previously described, the stored energy means, or member 225, will tend to return to its less compressed starting configuration thereby controllably urging fluid flow outwardly of the device reservoir via the flow control means of the invention. As the fluid contained within the reservoir is urged outwardly thereof by the stored energy means, the fluid will flow into a fluid passageway 374 formed in the first portion 370*a* of ullage member 370 (FIG. 54). The fluid will then flow under pressure through a filter means shown here as a filter 286 that is identical to that previously described. After flowing through filter 286, the fluid will flow, via a stub passageway 288 (FIG. 54) into the several radially outwardly extending flow passageways 290 formed in flow control member 256 (FIG. 44). The filtered fluid will fill passageways 290 and then will flow into the plurality of spiral passageways 260 formed in member 256 via outlets 260*b*, which communicate with passageways 260 (see FIG. 36). The fluid contained within spiral passageways 260 can flow outwardly of the device only when one of the fluid outlets 254 formed in casing 252 is aligned with passageway 372 (FIG. 54).

Selection of the passageway 260 from which the fluid is to be dispensed is accomplished by rotation of the selector knob 258 in the manner previously discussed in connection with the earlier described embodiments. The construction and operation of the selector knob, the indexing means and the locking means is identical to that previously described and will not be redescribed at this time.

As in the earlier described embodiments of the invention, as the fluid flows outwardly toward the patient via the administration set 264 due to the urging of the stored energy means or spring member 225, the bellows structure 223 will be generally collapsed and at the same time member 282 will travel inwardly of housing portion 386 and will provide an indication of the volume of fluid remaining in the fluid reservoir in the same manner as earlier described.

This latest embodiment also includes safety defeat disabling means 318, which is substantially identical in construction and operation to that previously described.

Considering next the alternate form of fill cartridge assembly 422, shown in FIG. 65. This fill cartridge is similar in some respects to fill cartridge 392 and includes a vial 424 that is sealed at one end by a plunger 425 and at the other end by an elastomeric pierceable septum 428. Formed intermediate the ends of vial 424 is a plurality of internal fluid flow passageways 430 which permit fluid 432 to bypass a strategically position barrier stopper 434 as the barrier stopper is urged inwardly of the container by pressure exerted thereon by fluid 432. Fluid 432 exerts pressure on barrier member 434 as a result of pusher member 404 of the vial housing 400 exerting inward pressure on plunger 425, which pressure is, in turn, caused by the inward movement of plunger 434 as vial housing 400 is mated with the housing 382 as is advanced therewithin.

A continued inward pressure exerted on plunger 425 will cause fluid 432 to flow past elastomeric barrier member 434 via internal bypass flow channels 430 so as to reconstitute lyophilized drug 433 (FIG. 65). Further pressure exerted on plunger 425 will advance plunger 434 to a more and subsequently fully distal location which will cause the reconstituted drug formed by the fluid 432 which has been intermixed with drug 433 to flow through a hollow cannula 412 past elastomeric check valve 414, into a stub passageway 416 and then into a passageway 418 and finally into the device reservoir via filing channel 420 (FIG. 54).

Referring now to FIGS. 67 through 97, yet another embodiment of the dispensing apparatus of the present invention is there illustrated and generally designated by the numeral 442. This alternate form of the apparatus of the invention is similar in some respects to the previously described embodiments of the invention and like numerals are used in FIGS. 67 through 97 to identify like components. The primary difference between this latest form of the invention and those previously discussed concerns the provision of a differently configured stored energy means and of a differently configured flow rate control means. Further, the reservoir fill means of this latest form of the invention includes only a single, cartridge type fill vial.

Figure 67:
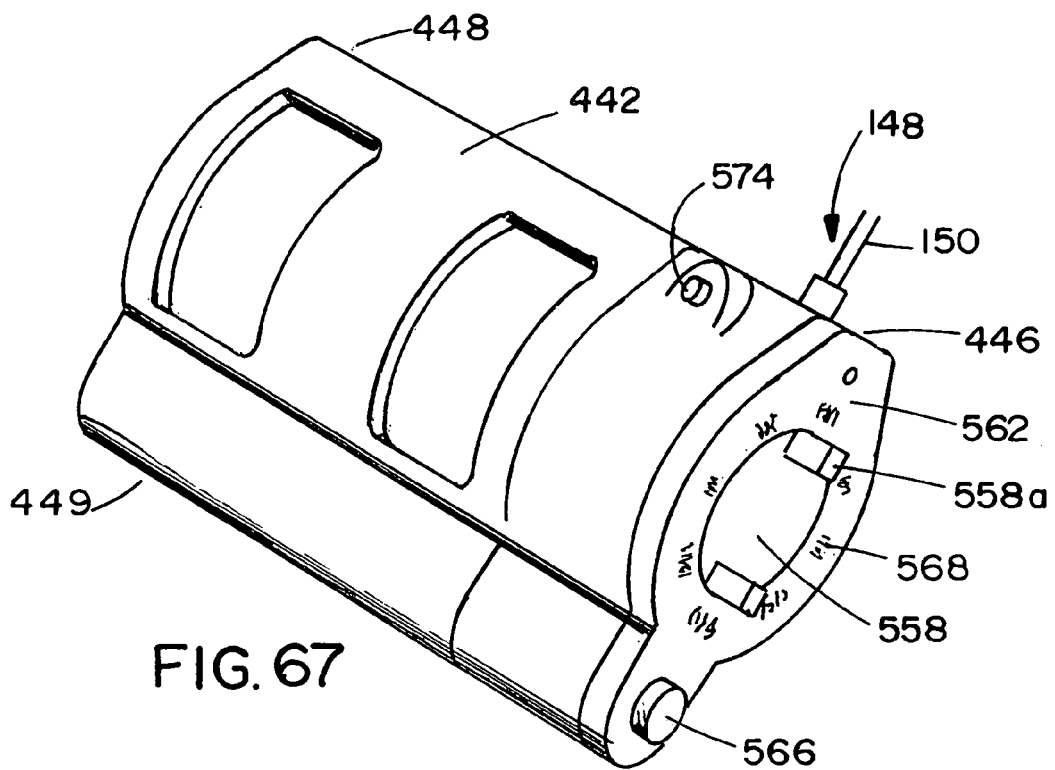
FIG. 67 is a generally perspective view of still another embodiment of the medicament infusion apparatus of the present invention for dispensing fluids at a uniform rate.

As best seen in FIG. 67, the apparatus here comprises an outer housing 442 having first, second and third portions 446, 448 and 449 respectively. Disposed within outer housing 442 is an inner, expandable housing 450, which is generally similar in construction and operation to expandable housing 223, which housing was described in connection with the embodiment of FIG. 21.

Figure 72:
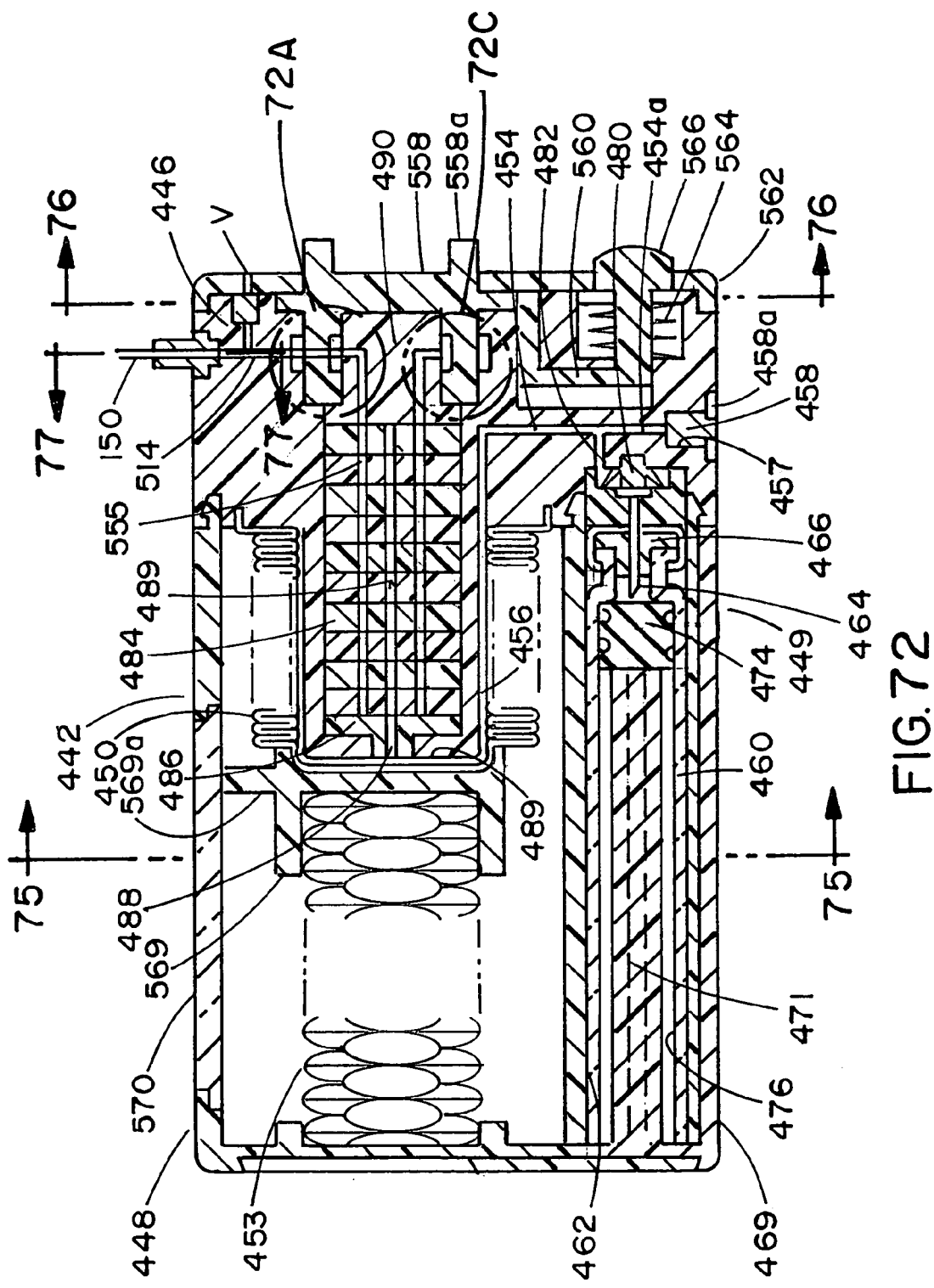
FIG. 72 is a cross-sectional view taken along lines 72—72 of FIG. 69.
Figure 72A:
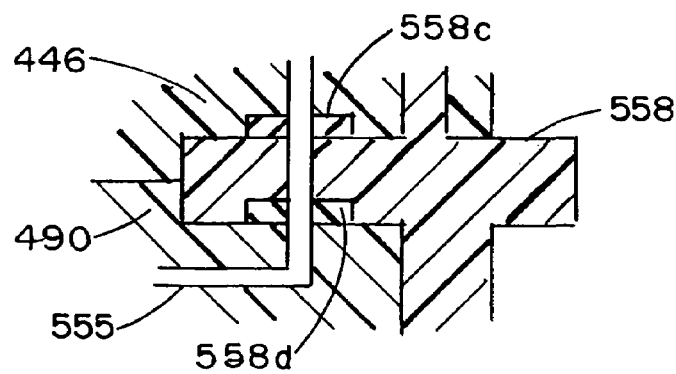
FIG. 72A is an enlarged, cross-sectional view of the area designated as 72A in FIG. 72.

Also disposed within outer housing 442 is the novel stored energy means of the invention for acting upon inner expandable housing 450 in a manner to cause the fluid contained within the fluid reservoir thereof to controllably flow outwardly of the housing (FIG. 72). In this latest form of the invention, this stored energy means comprises a plurality of cooperatively associated disk springs 453. These disk springs, exhibit superior load/deflection curves and are ideally suited for use in the present application. Springs 453 are readily commercially available from a number of sources including the Schnorr Co. of Sindelfingen, Germany.

Figure 68:
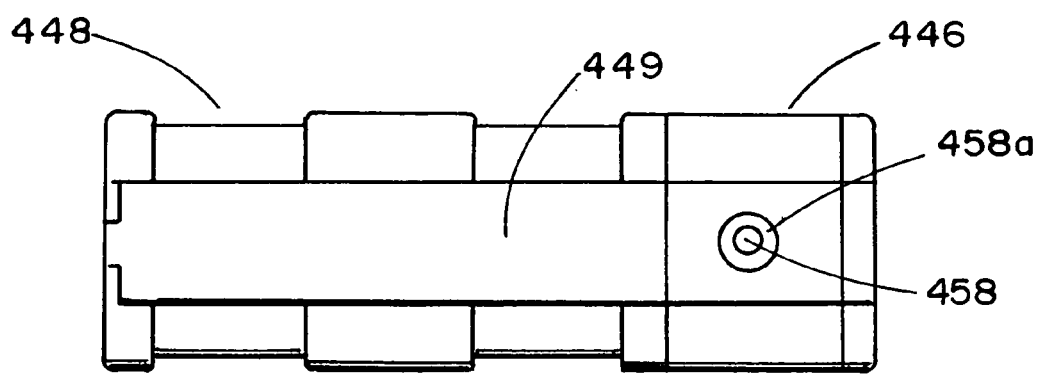
FIG. 68 is a bottom plan view of the embodiment of the apparatus shown in FIG. 67.
Figure 69:
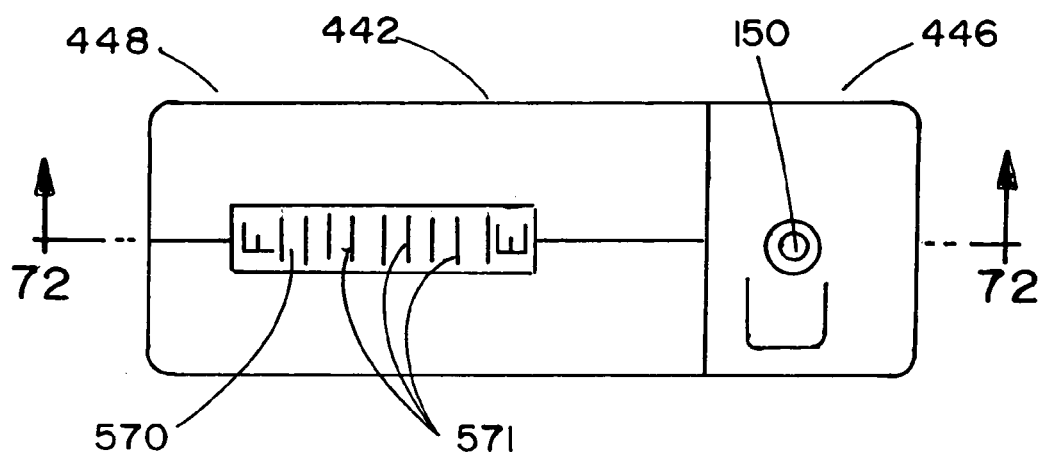
FIG. 69 is a top plan view of the embodiment of the apparatus shown in FIG. 67.

As in the earlier described embodiments of the invention, the present invention includes fill means, which are here carried by the third portion 449 of the outer housing. As before, the fill means functions to fill the device reservoir that is defined by bellows member 450 with the fluid to be dispensed. As best seen in FIGS. 67, 68 and 72 third housing portion 449 includes a fluid passageway 454 that is in communication with the inlet or passageway 456 of fluid reservoir. Proximate its lower end 454*a* fluid passageway 454 communicates with a cavity 457 formed within the third portion of the housing. Disposed within cavity 457 is a pierceable septum 458 that comprises a part of the fill means of this latest form of the invention. Septum 458 is held in position by a retainer 458*a* and is pierceable by the needle of the syringe which contains the medicinal fluid to be dispensed and which can be used in a conventional manner to fill or partially fill the device reservoir via passageway 454. As the reservoir fills, and gases trapped within the reservoir will be vented via vents "V".

The fill means also here comprises a cartridge type fill vial 460 which is of the construction shown in FIG. 72. As shown in FIG. 72, the third portion 449 of the housing includes a clamber 462 for telescopically receiving cartridge fill vial 460. A hollow needle 464 is mounted within third portion 449 of the device housing and is located proximate the inboard end of chamber 462. When the cartridge fill vial 460 is inserted into chamber 462 and pushed forwardly into the position shown in FIG. 72, hollow needle 464 will pierce a septum 466 that sealably closes the open end of the cartridge fill vial.

Figures 70, 71:
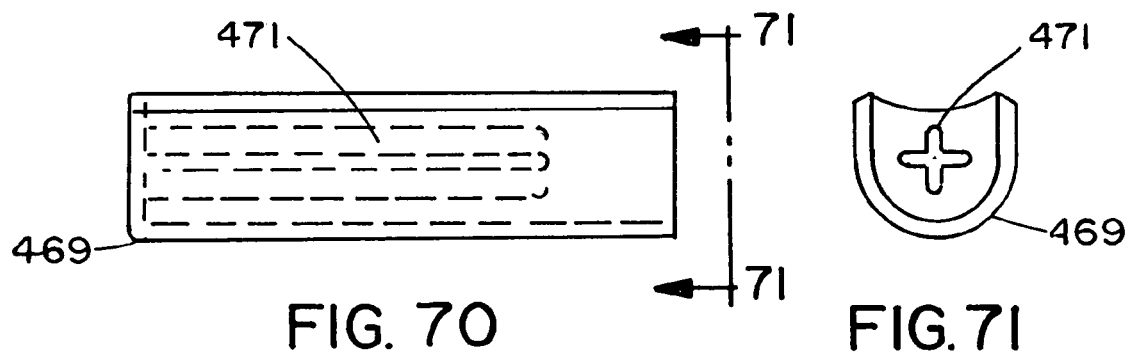
FIG. 70 is a side elevational view of the vial cover portion of the apparatus shown in FIG. 67.
FIG. 71 is a view taken along lines 71—71 of FIG. 70.

As illustrated in FIGS. 70, 71 and 72, the vial cover 469 of portion 449 of the device housing includes a pusher member 471 which engages a plunger 474 of vial 460 when the vial cover is mated with the device housing. Pusher member 471 functions to push the plunger forwardly of container reservoir 476 as the vial cover 469 is moved into the fully mated position shown in FIG. 72. As plunger 474 is moved forwardly of reservoir 476, the fluid contained in the vial reservoir will be forced through hollow needle 464, passed a conventional umbrella check valve 480 that is mounted within third housing portion 449, into a stub passageway 482, into passageways 454 and 456 and finally into the device reservoir. As the fluid flows into the device reservoir, it will controllably compress the stored energy means, or disc springs 453.

Turning particularly to FIGS. 78 through 97, the novel flow control means of the apparatus of this latest form of the invention is there shown. This important flow control means functions to precisely control the outwardly rate of fluid flow from the device reservoir toward the patient. In this latest form of the invention, the flow control means comprises a flow rate control assembly generally designated in the drawings by the numeral 484. This flow rate control assembly is non-rotatably mounted within housing portion 446 and includes an elongated spline 485 that functions to align the assembly within the outer housing. As best seen in FIGS. 72 and 81, this novel flow rate control assembly here comprises an inlet manifold 486 having an inlet port 488 (FIG. 72) that is in communication with the outlet 489 of the fluid reservoir and an outlet manifold 490 that is interconnected with inlet manifold 486 by means of a plurality of interconnected flow rate control plates 492, 494, 496, 498, 500, 502, 504, 506, 508 and 510 (see also FIGS. 82A and 82B).

As indicated in FIGS. 79, 80 and 85, outlet manifold 490 has a plurality of circumferentially spaced outlet ports, each of which is in communication with an outlet port of a selected one of the rate control plates. In a manner presently to be described, by using the selector means of the apparatus these circumferentially spaced outlet ports can be selectively brought into communication with outlet passageway 514 of the apparatus and with the administration line 150 of the administration set 148 (FIG. 72).

Figure 82A:
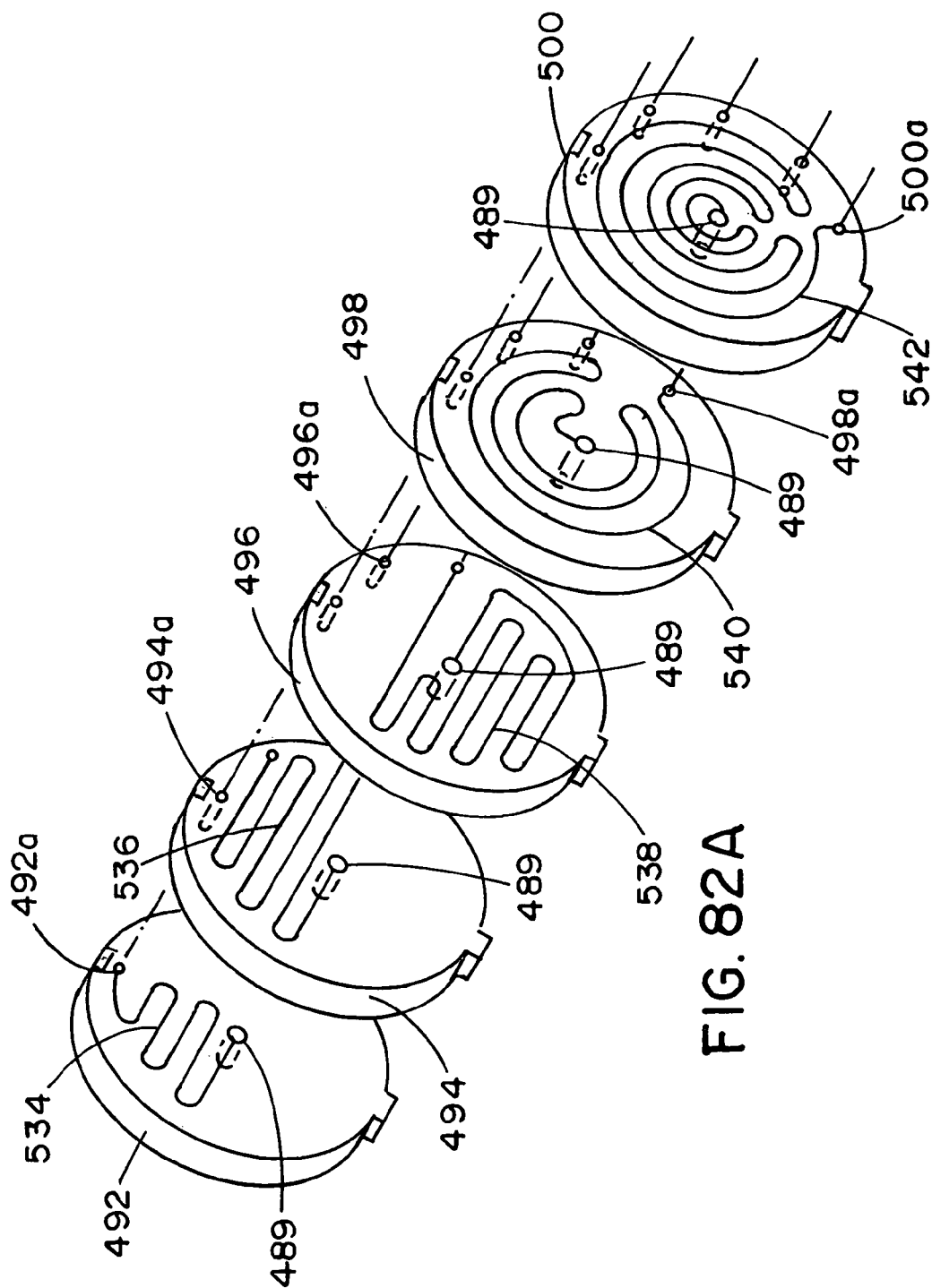
FIG. 82A is a generally perspective exploded view of the rear half of various flow rate control plates that make up the flow rate control plate assembly of the invention.
Figure 82B:
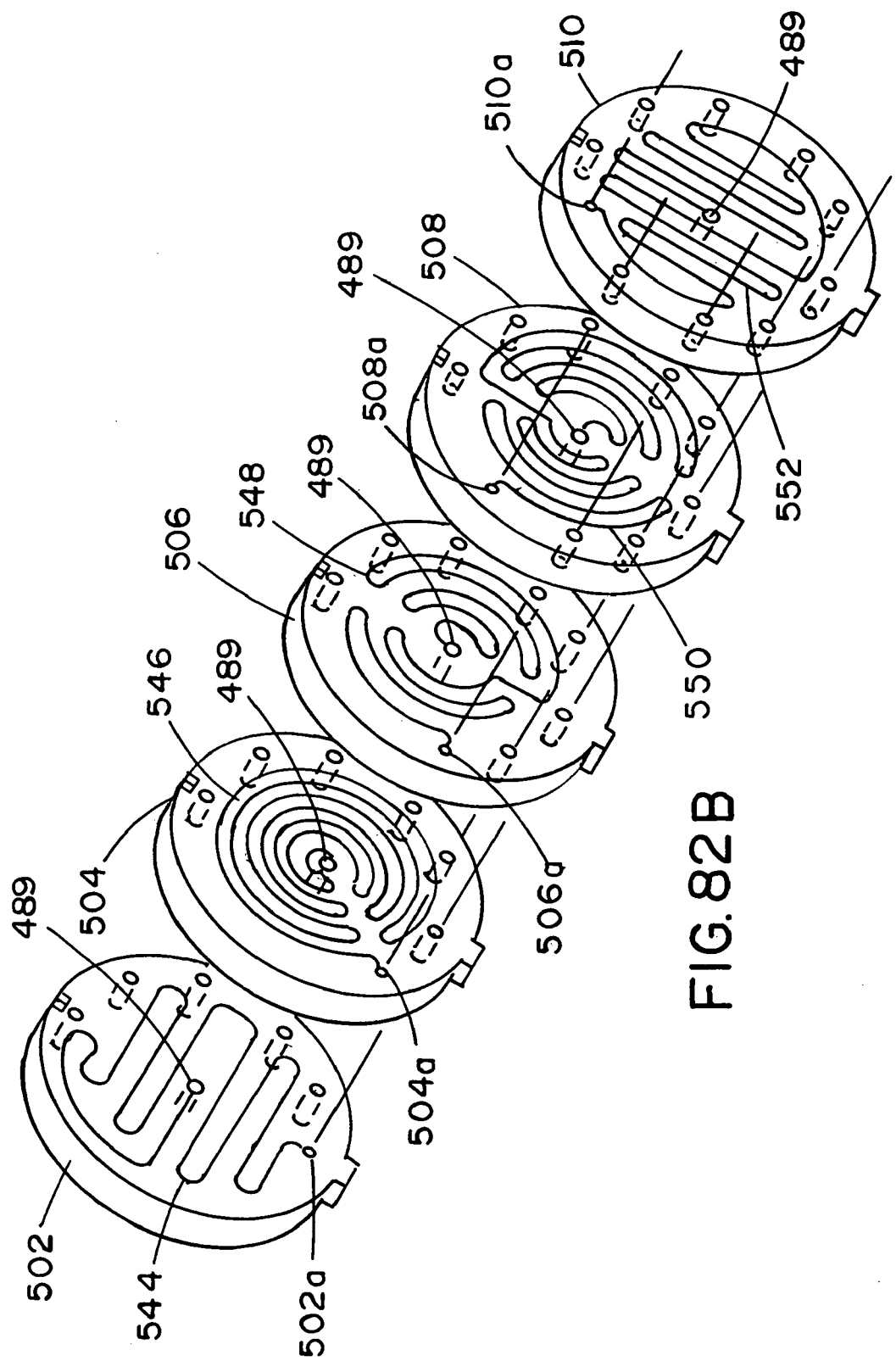
FIG. 82B is a generally perspective exploded view of the front half of various flow rate control plates that make up the flow rate control plate assembly of the invention.
Figure 83:
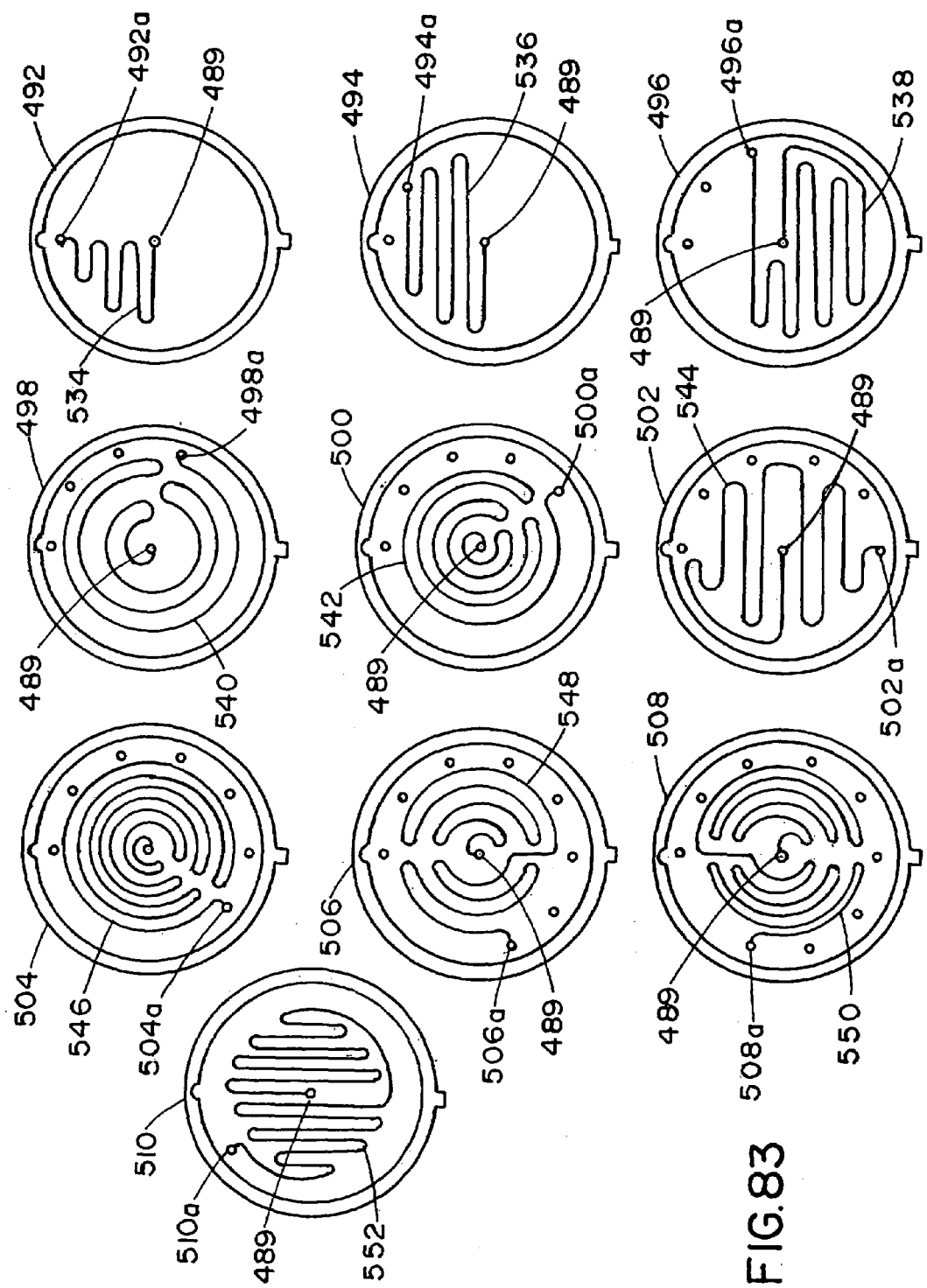
FIG. 83, when considered in its entirety, comprises a front view of each of the rate control plates of the invention shown in FIGS. 82A and 82B.
Figure 90:
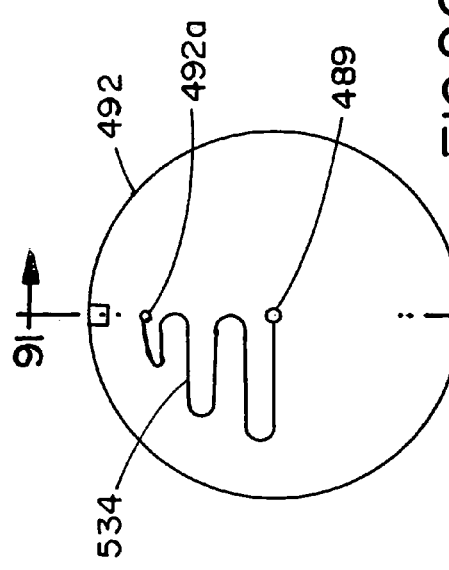
FIG. 90 is a front view of the rate control plate shown in FIG. 82.
Figure 93:
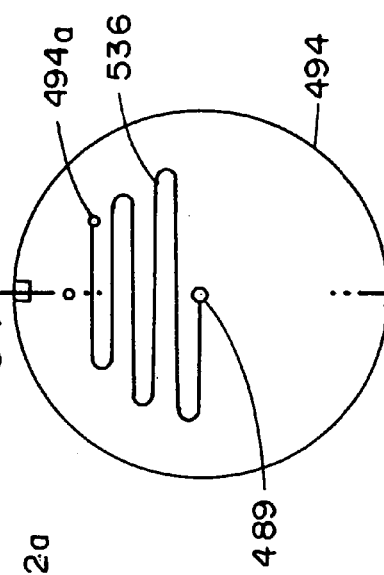
FIG. 93 is a rear view of the rate control plate shown in FIG. 92.
Figure 91:
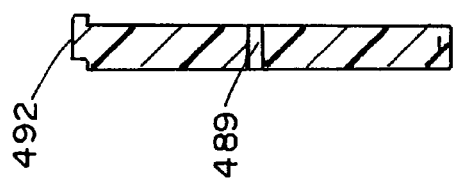
FIG. 91 is a cross-sectional view taken along lines 91—91 of FIG. 90.
Figure 94:
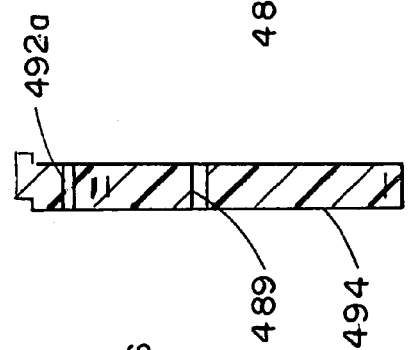
FIG. 94 is a cross-sectional view taken along lines 94—94 of FIG. 93.
Figure 89:
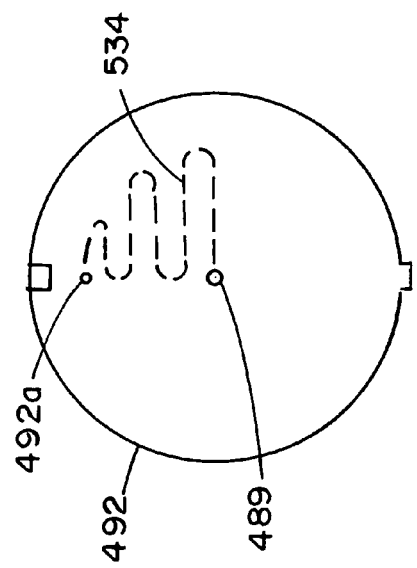
FIG. 89 is a front view of the first from the left, rate control plate or inlet manifold shown in FIG. 82.
Figure 92:
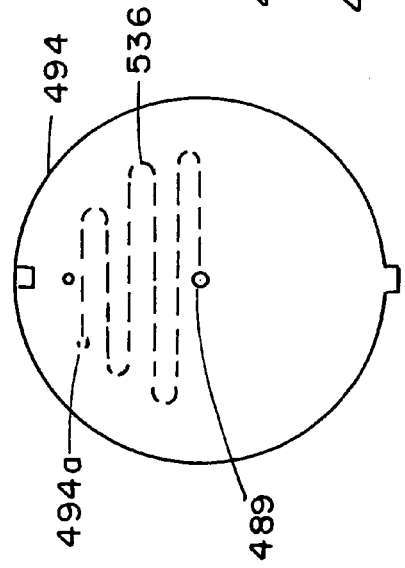
FIG. 92 is a front view of the second from the left, rate control plate shown in FIG. 82.

As best seen by referring to FIGS. 82A and 82B, each of the flow rate control plates is provided with an elongated micro channel of a particular configuration. These microflow channels can be formed in various ways known to those skilled in the art. For example, U.S. Pat. No. 6,176,962 issued to Soane et al. describes methods for constructing micro channel structures for use in micro fluidic manipulations. Similarly, International Publication WO 99/5694A1 describes such methods. When the rate control plates are assembled in the manner shown in FIGS. 82A and 82B, it is apparent that the micro channel formed in each of the rate control plates will cooperate with the adjacent planar surface of the next adjacent rate control plate to form a fluid flow control channel through which the fluid flowing into inlet 488 can controllably flow. As indicated in the drawings, one end of each of the micro channels is in communication with the inlet port 488 of the inlet manifold 486 via a center port 489 and the other end of each of the micro channels is in communication with a selected one of the circumferentially spaced outlet ports provided in the outlet manifold 490. More particularly, as can be seen by referring to FIGS. 82A, 82B, 83 and 88 of the drawings, outlet 492a of rate control plate 492 is in communication with outlet 521 of outlet manifold 490; outlet 494a of rate control plate 494 is in communication with outlet 522 of outlet manifold 490; outlet 496a of control plate 496 is in communication with outlet 523 of manifold 490; outlet 498a of control plate 498 is in communication with outlet 524 of outlet manifold 490 and outlet 500a of rate control 500 is in communication with outlet 525 of outlet manifold 490, and outlet 502a of rate control plate 502 is in communication with outlet 526 of outlet manifold 490. In similar fashion, outlet 504a of rate control plate 504 is in communication with outlet 527 of outlet manifold 490; outlet 506a of rate control plate 506 is in communication with outlet 528 of manifold 490; outlet 508a of control plate 508 is in communication with outlet 529 of outlet manifold 490 and outlet 510a of rate control plate 510 is in communication with outlet 530 of outlet manifold 490.

With the construction of the flow control means shown in the drawings, fluid will flow from the device reservoir into inlet port 488 of inlet manifold 486, through a filter member 533 (FIG. 85) and thence into micro channel 534 formed in plate 492. By controlling the length, width and depth of the micro channel 534, the rate of fluid flow flowing outwardly of outlet 492a can be precisely controlled. In a manner presently to be described, the fluid will then flow onwardly toward the administration set via the flow regulation means of the invention. It is to be understood that micro channel 534 can take various forms and can be of varying length, width and depth to precisely control the rate of fluid flow their through.

Fluid flowing through inlet port 488 will also flow into micro channel 536 formed in rate control plate 494. Once again, depending upon the length, width and depth of micro channel 536, the rate of fluid flowing outwardly of outlet 494a can be precisely controlled. In similar manner, fluid flowing through inlet port 488 will fill micro channel 538 formed in rate control plate 496, will fill micro channel 540 formed in plate 498, will fill micro channel 542 formed in rate control plate 500, will fill rate control micro channel 544 formed in rate control plate 502, will fill rate control micro channel 546 formed in rate control plate 504, will fill rate control micro channel 548 formed in rate control plate 506, will fill flow control micro channel 550 formed in rate control plate 508 and will fill rate control micro channel 552 formed in rate control plate 510. After flowing through the rate control micro channels formed in the various indexedly aligned rate control plates, the fluid will flow onwardly toward outlet manifold 490 and will fill each of the stub passageways 555 formed therein (FIG. 87). The rate of flow of fluid flowing outwardly of each of the outlet ports of the various rate control plates will, of course depend upon the configuration of the individual rate control micro channels formed in the rate control plates.

Figure 72B:
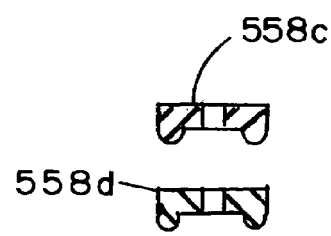
FIG. 72B is an enlarged, cross-sectional view of the elastomeric sealing band shown in FIG. 72A.
Figure 72C:
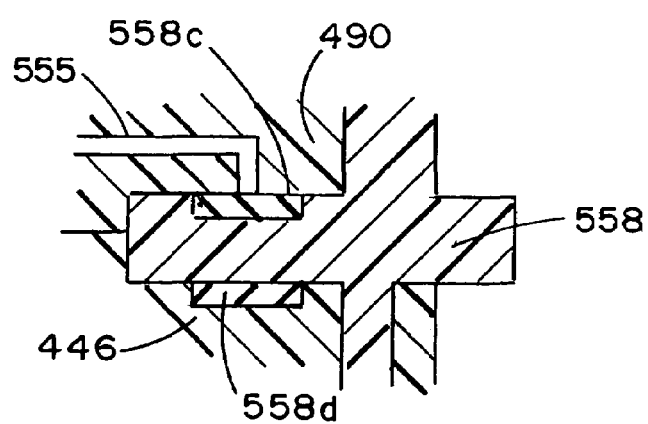
FIG. 72C is an enlarged, cross-sectional view of the area designated as 72C in FIG. 72.
Figure 72D:
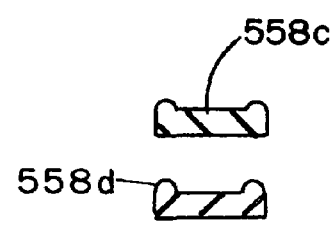
FIG. 72D is an enlarged, cross-sectional view of the elastomeric sealing band shown in FIG. 72C.
Figure 73:
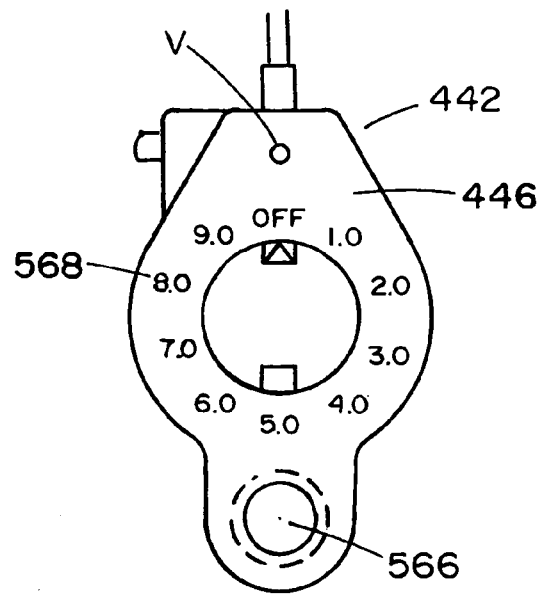
FIG. 73 is a right end view of the apparatus shown in FIG. 67.
Figure 74:
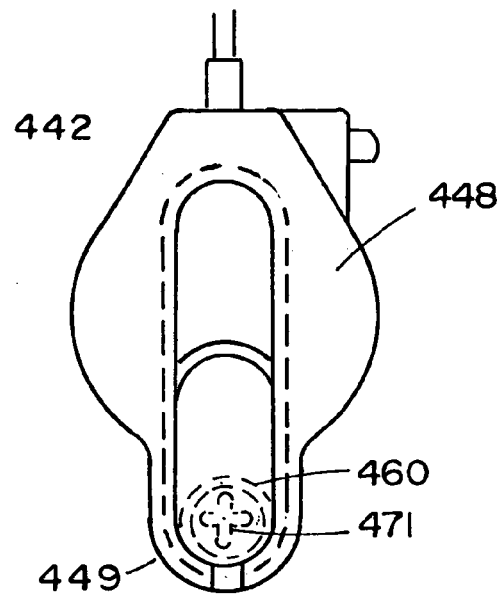
FIG. 74 is a left end view of the apparatus shown in FIG. 67.
Figure 75:
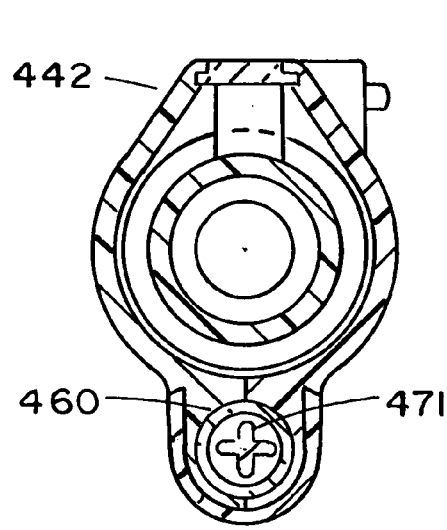
FIG. 75 is a cross-sectional view taken along lines 75—75 of FIG. 72.
Figure 76:
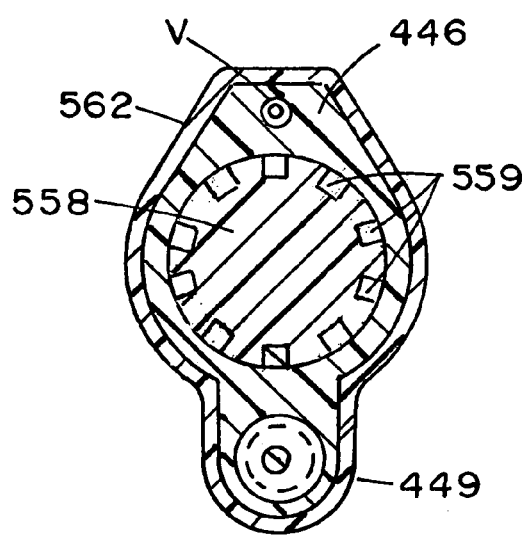
FIG. 76 is a cross-sectional view taken along lines 76—76 of FIG. 72.

As shown in FIGS. 72 and 76, a selector knob 558 which is sealably rotatably connected to first portion 446 of the outer housing, is provided with a plurality of circumferentially spaced apart indexing cavities 559. Elastomeric sealing bands 558c and 558d, which are of the unique configuration shown in FIGS. 72B and 72D, prevent leakage between the cooperatively mated components. These indexing cavities closely receive an indexing finger 560, which forms a part of the indexing means of the invention, which means comprises a front bezel 562 that is connected to the apparatus housing (see FIG. 67). Indexing finger 560 is continuously urged into engagement with a selected one of the indexing cavities 559 by a coil spring 564 that also forms a part of the indexing means of the invention. Coil spring 564 can be compressed by an inward force exerted on an indexing shaft 566 that is movable from an extended position to an inward, finger release position wherein spring 564 is compressed and finger 560 is retracted from a selected indexing cavity 559. With finger 560 in its retracted position, it is apparent that control knob 558 can be freely rotated to a position wherein a gripping member 558a can be aligned with selected flow rate indicia 568 formed on the front bezel 562 of the apparatus housing.

When the selector knob is in the desired position and pressure is released on indexing shaft 566, spring 564 will urge finger 560 of the indexing means of the invention into locking engagement with one of the indexing cavities 559 thereby placing a selected one of flow control channels of a flow rate control plate in communication with flow passageway 558b of the flow control knob (FIG. 81). As the fluid flows outwardly of the apparatus due to the urging of the stored energy means or spring members 453, the bellows structure 450 will be collapsed and at the same time and indicator member 569 will travel inwardly of the housing. Member 569, which forms a part of the volume indicator means of the invention, includes a radially outwardly extending indicating finger 569a that is visible through a volume indicator window 570 that is provided in a second portion 448 of the apparatus housing and also comprises a part of the volume indicator means of the invention. Indicia 571, which are provided on indicator window 570 (FIG. 69), function to readily indicate to the caregiver the amount of fluid remaining within fluid reservoir of the device at any point in time.

Referring to FIGS. 67 and 77, disabling means, shown here as a disabling shaft 574 that is telescopically movable within a passageway formed within housing portion, functions in the manner previously described to disable the device (see discussion concerning FIG. 22A).

Figure 95A:
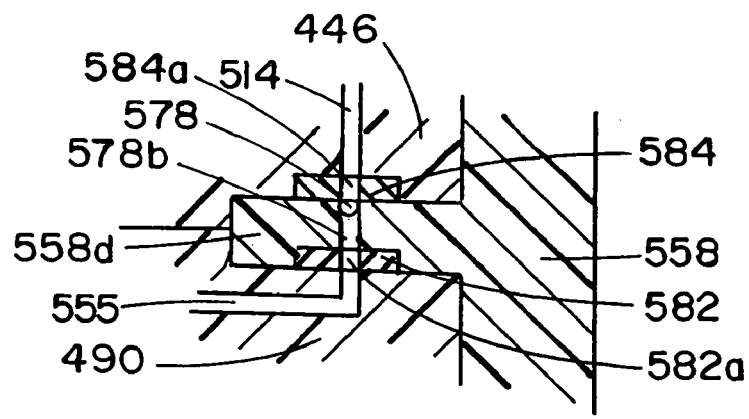
FIG. 95 is a fragmentary cross-sectional view of the forward portion of the outlet manifold of the flow control means shown sealably mated with the rate control knob of the apparatus of the invention.
Figure 95:
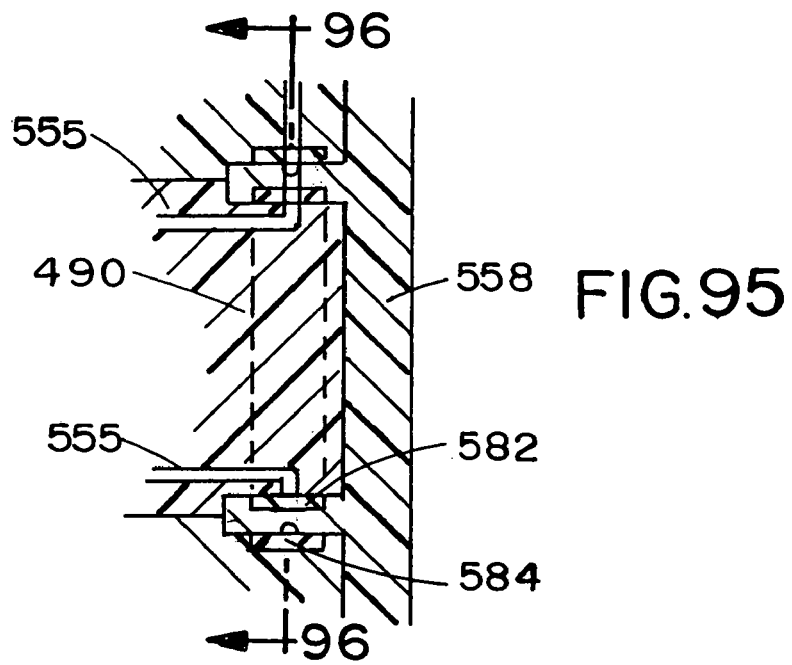
Figure 95B:
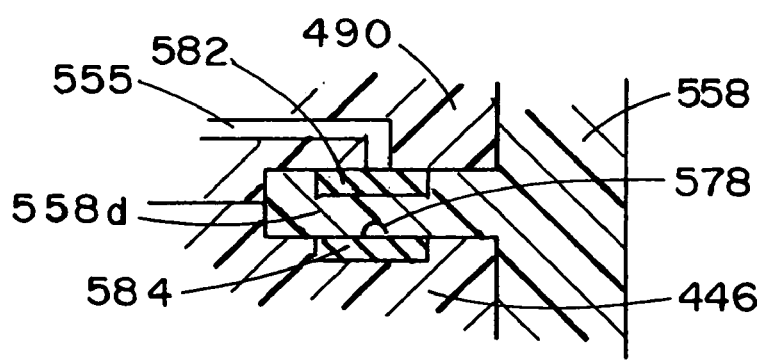
Figure 96:
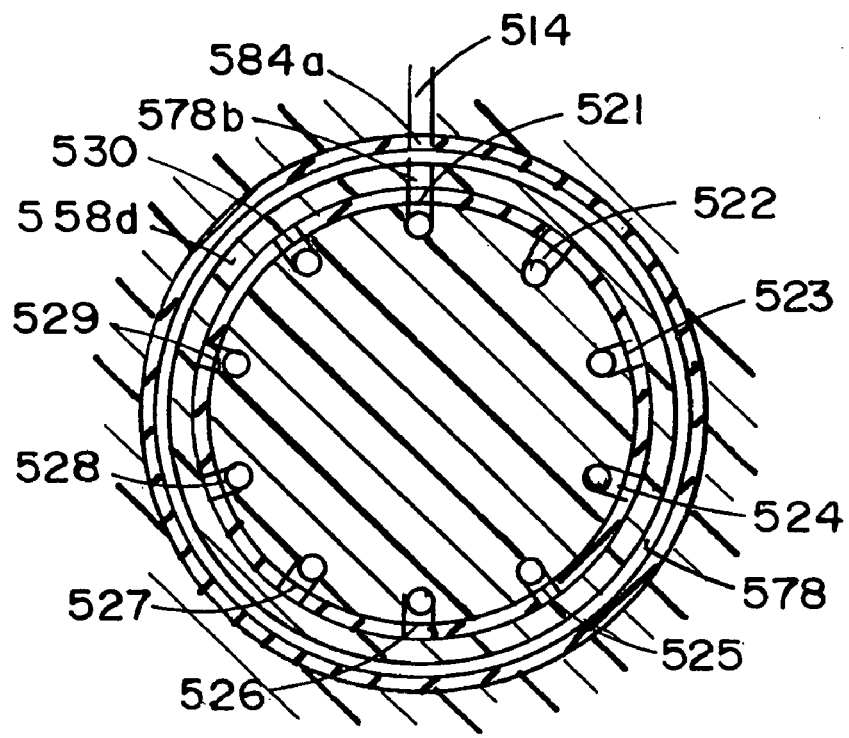
Figure 97:
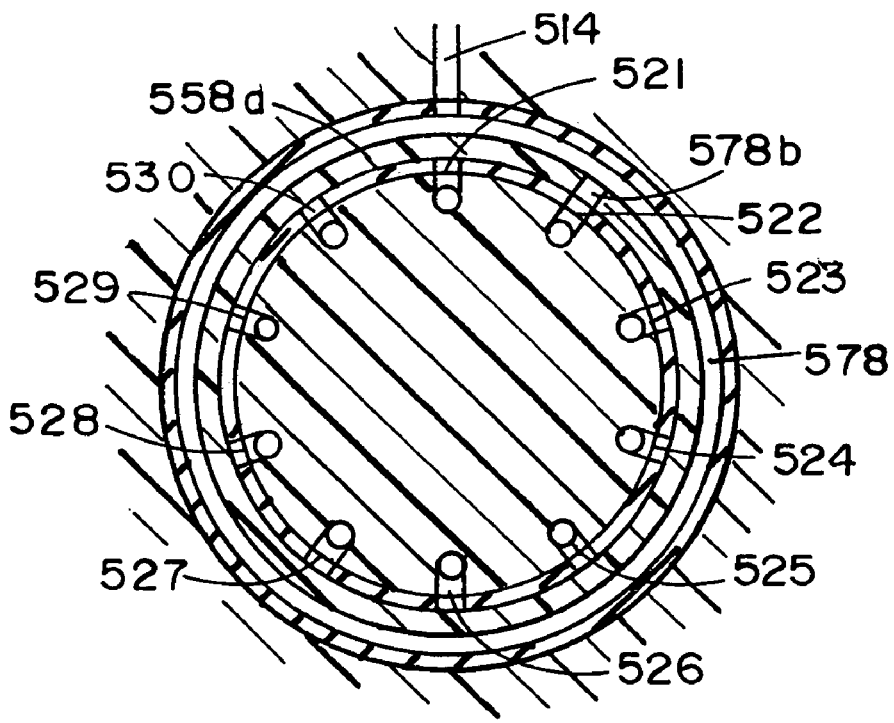

Referring particularly to FIG. 95, selector knob 558 (see also FIGS. 78 and 81), which comprises a part of the selector means of the invention, is sealably connected to outlet manifold 490 by means of O-Rings "O" and is rotatable with respect thereto. As previously mentioned, this novel selector means of the invention functions to control the flow of fluid from outlet manifold 490 toward the administration set 150. More particularly, as illustrated in FIGS. 95, 95A and 95B, selector knob 558 is provided with a circumferentially extending flow channel 578 which is selectively in communication with passageways 555 of outlet manifold 490 depending upon the position of the selector knob. As illustrated in FIGS. 95A and 95B, the rearwardly-extending, generally-cylindrical, reduced-diameter portion 558d of the control knob, which circumscribes the outlet manifold 490, is provided with a circumferentially extending, elastomeric band 582 which prevents fluid leakage between the outlet manifold and the flange 558d. Outlet manifold 490 is also provided with a similarly configured, circumferentially extending, elastomeric band 584. As indicated in FIG. 95A, elastomeric band 584 has an opening 584a that is in alignment with fluid outlet passageway 514 formed in the first portion 446 of the outer housing (see also FIG. 72). Elastomeric band 582 also has an opening 582a which is aligned with a radially extending flow passageway 578b formed on portion 558d of the control knob, which, in turn, is in communication with circumferentially extending flow channel 578 (FIG. 95A). With this construction, when the control knob 558 is rotated to a position such as that illustrated in FIG. 95A, wherein one of the outlets of the outlet manifold is in alignment with the opening 582a formed in the elastomeric band 582, fluid can flow from that outlet and into circumferentially extending flow channel 578. From flow channel 578, the fluid can flow into radially extending passageway 578b, through opening 584a and into passageway 514. From passageway 514, the fluid can flow onwardly into the dispensing means or administration set 148. The rate at which the fluid flows toward the administration set depends, of course, upon which rate control plate outlet is in communication with radial passageway 578b formed in the control knob. By way of example, with the control knob 558 in the position shown in FIG. 95A, it is to be observed that the fluid flowing toward the administration set is flowing from outlet 492a of rate control plate 492 and will flow at a rate determined by the configuration of rate control micro channel 534. (see FIGS. 82 and 96).

Having now described the invention in detail in accordance with the requirements of the patent statutes, those skilled in this art will have no difficulty in making changes and modifications in the individual parts or their relative assembly in order to meet specific requirements of conditions. Such changes and modifications may be made without departing from the scope and spirit of the invention, as set forth in the following claims.

I claim:

1. A dispensing apparatus for dispensing fluids to a patient comprising:
    (a) an outer housing having a first, second and third portions;
    (b) an inner, expandable housing disposed within said outer housing, said inner expandable housing having a fluid reservoir provided with an inlet for permitting fluid flow into said fluid reservoir;
    (c) stored energy means disposed within said second portion of said outer housing for acting upon said inner expandable housing to cause the fluid contained within said fluid reservoir to controllably flow outwardly toward the patient, said stored energy means comprising a compressively deformable, spring member carried within said second portion of said outer housing, said spring member being expandable to cause fluid flow from said fluid reservoir;
    (d) fill means carried by said outer housing for filling said reservoir with the fluid to be dispensed;
    (e) flow control means connected to said first portion of said outer housing for controlling fluid flow from said reservoir, said flow control means comprising a flow control assembly including:
        (i) an ullage defining member having a first portion disposed within said inner, expandable housing and a second portion having a fluid passageway in communication with said outlet of said fluid reservoir;
        (ii) a flow control member rotatably mounted within said first portion of said ullage defining member, said flow control member having a plurality of elongated flow control channels, each of said plurality of elongated flow control channels having an inlet and an outlet; and
        (iii) selector means rotatably connected to said second portion of said ullage defining member for rotating said flow control member to selectively align an outlet of one of said elongated flow control channels with said with fluid passageway in said second portion of said ullage defining member; and
        (iv) dispensing means for dispensing fluid to the patient, said dispensing means being connected to said second portion of said ullage defining member, and being in communication with said fluid passageway of said second portion of said ullage defining member.

2. The apparatus as defined in claim 1 in which said flow control assembly further comprises:
(a) an outer casing circumscribing said flow control member; and
(b) distribution means formed in said flow control member for distributing fluid from said fluid reservoir to each of said plurality of elongated flow control channels.

3. The apparatus as defined in claim 2, in which said flow control member is provided with an inlet passageway in communication with said fluid reservoir and in which said flow control assembly further includes filter means carried by said flow control member for filtering fluid flowing toward said distribution means.

4. The apparatus as defined in claim 3 in which said distribution means comprises a plurality of radially extending flow passageways formed in said flow control member.

5. The apparatus as defined in claim 3 in which said selector means comprises a selector knob connected to said flow control member, said selector knob having finger gripping means for imparting rotation to said selector knob to align said outlet of a selected one of said elongated flow control channels with said outlet of said fluid passageway in said second portion of said ullage defining member.

6. The apparatus as defined in claim 3, further including volume indicator means carried by said outer housing for indicating the volume of fluid remaining in said fluid reservoir.

7. The apparatus as defined in claim 3 further including disabling means carried by said outer housing for preventing fluid flow toward said dispensing means.

8. The apparatus as defined in claim 3 in which said outer housing includes a cavity in communication with said inlet of said fluid reservoir and in which said fill means comprises a pierceable septum disposed within said cavity.

9. The apparatus as defined in claim 8 in which said fill means comprises a first fill vial receivable within said third portion of said outer housing.

10. The apparatus as defined in claim 9 in which said fill means comprises a second fill vial receivable within said third portion of said outer housing.

11. The apparatus as defined in claim 10 in which said third portion of said outer housing includes:
(a) a fluid passageway in communication with said inlet of said fluid reservoir;
(b) a first chamber for telescopically receiving said first fill vial;
(c) an elongated support mounted within said first chamber, said elongated support having an elongated hollow needle, said hollow needle defining a flow passageway in communication with said fluid passageway;
(d) a second chamber for telescopically receiving said second fill vial; and
(e) an elongated support mounted within said second chamber, said elongated support having an elongated hollow needle, said hollow needle defining a flow passageway in communication with said fluid passageway.

12. The apparatus as defined in claim 11 in which each of said first and second fill vials has a first open end, a closed second end and each includes;

(a) a fluid reservoir disposed between said first and second ends; and
(b) a pierceable plunger disposed within said fluid reservoir for movement between first and second positions.

13. A dispensing apparatus for dispensing fluids to a patient comprising:
(a) an outer housing having a first, second and third portions;
(b) an inner, expandable housing disposed within said outer housing, said inner expandable housing having a fluid reservoir provided with an inlet for permitting fluid flow into said fluid reservoir;
(c) stored energy means disposed within said second portion of said outer housing for acting upon said inner expandable housing to cause the fluid contained within said fluid reservoir to controllably flow outwardly toward the patient, said stored energy means comprising a yieldably deformable spring carried within said second portion of said outer housing, said yieldably deformable spring being expandable to cause fluid flow from said fluid reservoir;
(d) fill means carried by said outer housing for filling said reservoir with the fluid to be dispensed;
(e) flow control means connected to said first portion of said outer housing for controlling fluid flow from said reservoir, said flow control means comprising a flow control assembly including:
(i) an ullage defining member having a first portion disposed within said inner, expandable housing and a second portion having a fluid passageway in communication with said outlet of said fluid reservoir;
(ii) a flow control member rotatably mounted within said first portion of said ullage defining member, said flow control member having a plurality of elongated flow control channels, each of said plurality of elongated flow control channels having an inlet and an outlet;
(iii) an outer casing circumscribing said flow control member;
(iv) distribution means formed in said flow control member for distributing fluid from said fluid reservoir to each of said plurality of elongated flow control channels, said distribution means comprising a plurality of radially extending flow passageways formed in said flow control member;
(v) selector means rotatably connected to said second portion of said ullage defining member for rotating said flow control member to selective align an outlet of one of said elongated flow control channels with said fluid passageway of said second portion of said ullage defining member said selector means comprising a selector knob connected to said flow control member, said selector knob having
(vi) finger gripping means for imparting rotation to said selector knob to align said outlet of a selected one of said elongated flow control channels with said outlet of said fluid passageway in said second portion of said ullage defining member; and
(vii) dispensing means for dispensing fluid to the patient, said dispensing means being connected to said second portion of said ullage defining member, and being in communication with said fluid passageway of said second portion of said ullage defining member; and
(f) volume indicator means for indicating the volume of fluid remaining in said fluid reservoir.

14. The apparatus as defined in claim 13 further including disabling means carried by said outer housing for preventing fluid flow toward said dispensing means.

15. The apparatus as defined in claim 13 in which said outer housing includes a cavity in communication with said inlet of said fluid reservoir and in which said fill means comprises a pierceable septum disposed within said cavity.

16. The apparatus as defined in claim 13 further including locking means carried by said outer housing for blocking rotation of said selector knob.

17. The apparatus as defined in claim 13 in which said fill means comprises a fill vial receivable within said third portion of said outer housing.

* * * * *